(12) United States Patent
Jones et al.

(10) Patent No.: US 11,270,876 B2
(45) Date of Patent: Mar. 8, 2022

(54) IONISATION OF GASEOUS SAMPLES

(71) Applicant: Micromass UK Limited, Wilmslow (GB)

(72) Inventors: Emrys Jones, Manchester (GB); Tamas Karancsi, Budapest (HU); Steven Derek Pringle, Darwen (GB); Julia Balog, Solymar (HU); Daniel Simon, Morichida (HU); Lajos Godorhazy, Erd (HU); Daniel Szalay, Budapest (HU); Zoltan Takats, Cambridge (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/555,758

(22) PCT Filed: Mar. 7, 2016

(86) PCT No.: PCT/GB2016/050612
§ 371 (c)(1),
(2) Date: Sep. 5, 2017

(87) PCT Pub. No.: WO2016/142683
PCT Pub. Date: Sep. 15, 2016

(65) Prior Publication Data
US 2018/0053644 A1    Feb. 22, 2018

(30) Foreign Application Priority Data

Mar. 6, 2015 (GB) ..................................... 1503863
Mar. 6, 2015 (GB) ..................................... 1503864
(Continued)

(51) Int. Cl.
*H01J 49/00* (2006.01)
*H01J 49/04* (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
CPC .... H01J 49/0036; H01J 49/0422; H01J 49/14; A61B 18/1815; A61B 10/00;
(Continued)

(56) References Cited

U.S. PATENT DOCUMENTS 3,479,545 A   11/1969 Wilson et al.
3,770,954 A   11/1973 Davis
(Continued)

FOREIGN PATENT DOCUMENTS

CA   2527886 A1   12/2004
CA   2876731 A1   12/2013
(Continued)

OTHER PUBLICATIONS

Guenther, et al ("Electrospray Post-Ionization Mass Spectrometry of Electrosurgical Aerosols" Am. Soc. Mass Spectrom. (2011) 22:2082-2089) (Year: 2011).*
(Continued)

*Primary Examiner* — Michael Maskell
(74) *Attorney, Agent, or Firm* — Kacvinsky Daisak Bluni PLLC

(57) ABSTRACT

A method of mass spectrometry or ion mobility spectrometry is disclosed comprising: providing an analyte; supplying a matrix compound to said analyte such that said analyte dissolves in said matrix; forming first droplets of the dissolved analyte; and colliding said first droplets with a collision surface. The use of matrix improves the analyte ion signal.

20 Claims, 48 Drawing Sheets

(30) Foreign Application Priority Data

| Mar. 6, 2015 | (GB) | 1503867 |
|---|---|---|
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| *A61B 90/13* | (2016.01) |
|---|---|
| *A61B 1/04* | (2006.01) |
| *A61B 1/273* | (2006.01) |
| *A61B 5/00* | (2006.01) |
| *A61B 5/01* | (2006.01) |
| *A61B 5/0507* | (2021.01) |
| *A61B 5/055* | (2006.01) |
| *A61B 6/03* | (2006.01) |
| *A61B 8/13* | (2006.01) |
| *A61B 10/00* | (2006.01) |
| *A61B 10/02* | (2006.01) |
| *A61B 17/00* | (2006.01) |
| *A61B 17/32* | (2006.01) |
| *A61B 18/00* | (2006.01) |
| *A61B 18/04* | (2006.01) |
| *A61B 18/14* | (2006.01) |
| *A61B 18/18* | (2006.01) |
| *A61B 18/20* | (2006.01) |
| *A61F 13/38* | (2006.01) |
| *C12Q 1/02* | (2006.01) |
| *C12Q 1/04* | (2006.01) |
| *C12Q 1/18* | (2006.01) |
| *C12Q 1/24* | (2006.01) |
| *G01N 1/22* | (2006.01) |
| *G01N 3/00* | (2006.01) |
| *G01N 9/00* | (2006.01) |
| *G01N 27/622* | (2021.01) |
| *G01N 27/624* | (2021.01) |
| *G01N 30/72* | (2006.01) |
| *G01N 33/487* | (2006.01) |
| *G01N 33/68* | (2006.01) |
| *G01N 33/92* | (2006.01) |
| *H01J 49/02* | (2006.01) |
| *H01J 49/06* | (2006.01) |
| *H01J 49/10* | (2006.01) |
| *H01J 49/14* | (2006.01) |
| *H01J 49/16* | (2006.01) |
| *H01J 49/24* | (2006.01) |
| *H01J 49/26* | (2006.01) |
| *G16H 10/40* | (2018.01) |
| *G16H 15/00* | (2018.01) |
| *G16H 50/20* | (2018.01) |
| *G16B 20/00* | (2019.01) |
| *A61B 1/00* | (2006.01) |
| *A61B 1/31* | (2006.01) |
| *A61B 5/145* | (2006.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/0404* (2013.01); *H01J 49/044* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(58) Field of Classification Search
CPC .................. A61B 18/042; A61B 18/20; A61B 2010/0083; A61B 2218/008; A61B 2017/320069; A61B 2018/00577; G16H 50/20; G06F 19/324; G06F 19/3481; G06F 19/18; G06F 19/345
USPC ........................................ 250/281, 282, 288
See application file for complete search history.

(56) References Cited

U.S. PATENT DOCUMENTS

| 4,408,125 | A | 10/1983 | Meuzelaar |
|---|---|---|---|
| H414 | H | 1/1988 | Young et al. |
| 4,835,383 | A | 5/1989 | Mahoney et al. |
| 4,845,367 | A | 7/1989 | Amirav et al. |
| 4,883,958 | A | 11/1989 | Vestal |
| 4,935,624 | A | 6/1990 | Henion et al. |
| 5,033,541 | A | 7/1991 | D'Silva |
| 5,053,343 | A | 10/1991 | Vora et al. |
| 5,257,991 | A | 11/1993 | Fletcher et al. |
| 5,308,977 | A | 5/1994 | Oishi et al. |
| 5,374,755 | A | 12/1994 | Neue et al. |
| 5,454,274 | A | 10/1995 | Zhu |
| 5,509,916 | A | 4/1996 | Taylor |
| 5,559,326 | A | 9/1996 | Goodley et al. |
| 5,663,561 | A | 9/1997 | Franzen et al. |
| 5,696,352 | A | 12/1997 | Kourimsky |

(56) References Cited

U.S. PATENT DOCUMENTS

| | | |
|---|---|---|
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage et al. |
| 6,333,632 B1 | 12/2001 | Yang et al. |
| 6,348,688 B1 | 2/2002 | Vestal |
| 6,825,464 B2 | 11/2004 | De La Mora |
| 6,998,622 B1 | 2/2006 | Wang et al. |
| 7,238,936 B2 * | 7/2007 | Okamura ............ H01J 49/025 250/284 |
| 7,247,845 B1 | 7/2007 | Gebhardt et al. |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Sartor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 9,046,448 B2 | 6/2015 | Takats |
| 9,053,914 B2 | 6/2015 | Pringle et al. |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 * | 3/2016 | Takats ................ G01N 30/7253 |
| 9,287,100 B2 | 3/2016 | Szalay et al. |
| 9,709,529 B2 | 7/2017 | Takats |
| 9,731,219 B2 | 8/2017 | Wang et al. |
| 9,947,524 B2 | 4/2018 | Pringle et al. |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund, Jr. et al. |
| 2003/0001084 A1 | 1/2003 | Bateman et al. |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1 | 11/2004 | Bai et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 | 6/2005 | Brounstein et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0179366 A1 | 8/2005 | Rose et al. |
| 2005/0230634 A1 | 10/2005 | Bajic et al. |
| 2005/0230635 A1 | 10/2005 | Takats et al. |
| 2005/0258358 A1 | 11/2005 | Thakur |
| 2005/0269518 A1 | 12/2005 | Bajic et al. |
| 2005/0274885 A1 | 12/2005 | Brown et al. |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahem et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114388 A1 | 5/2007 | Ogawa et al. |
| 2007/0114394 A1 | 5/2007 | Combs et al. |
| 2007/0114437 A1 | 5/2007 | Kovtoun |
| 2007/0176092 A1 | 8/2007 | Miller et al. |
| 2007/0176113 A1 | 8/2007 | Shiea et al. |
| 2007/0181802 A1 * | 8/2007 | Yamada ............ H01J 49/0422 250/288 |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0132890 A1 | 6/2008 | Woloszko et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0088772 A1 | 4/2009 | Blumenkranz |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0294660 A1 | 12/2009 | Whitehouse et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 * | 7/2010 | Vidal-De-Miguel ........ H01J 49/145 250/282 |
| 2010/0186524 A1 | 7/2010 | Ariessohn et al. |
| 2010/0229263 A1 | 9/2010 | Vertes et al. |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0066147 A1 | 3/2011 | He et al. |
| 2011/0087308 A1 | 4/2011 | Morgan |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0043460 A1 | 2/2012 | Wouters et al. |
| 2012/0048264 A1 | 3/2012 | Finlay et al. |
| 2012/0074306 A1 | 3/2012 | Jesse et al. |
| 2012/0079894 A1 | 4/2012 | Berkel et al. |
| 2012/0080592 A1 | 4/2012 | Wiseman et al. |
| 2012/0085649 A1 | 4/2012 | Sano et al. |
| 2012/0119079 A1 | 5/2012 | Ouyang et al. |
| 2012/0149009 A1 | 6/2012 | Levis et al. |
| 2012/0156712 A1 * | 6/2012 | Takats ................. G01N 1/02 435/29 |

(56) References Cited

U.S. PATENT DOCUMENTS

| | | |
|---|---|---|
| 2012/0295276 A1 | 11/2012 | Cooks et al. |
| 2013/0123919 A1 | 5/2013 | Goldstein et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2014/0039480 A1 | 2/2014 | Van Wyk |
| 2014/0151547 A1* | 6/2014 | Bajic ............... H01J 49/0445 250/282 |
| 2014/0268134 A1 | 9/2014 | O'Connor |
| 2014/0276775 A1 | 9/2014 | Funk et al. |
| 2014/0291506 A1 | 10/2014 | Tikhonski |
| 2014/0297201 A1* | 10/2014 | Knorr ............... H01J 49/0036 702/28 |
| 2014/0299577 A1 | 10/2014 | Chung |
| 2014/0303449 A1 | 10/2014 | Balog |
| 2014/0326865 A1 | 11/2014 | Pringle et al. |
| 2014/0336456 A1 | 11/2014 | Demers et al. |
| 2014/0350534 A1 | 11/2014 | Kircher et al. |
| 2014/0353488 A1* | 12/2014 | Takats ............... G01N 30/7253 250/282 |
| 2014/0353489 A1* | 12/2014 | Szalay ............... H01J 49/16 250/282 |
| 2015/0021469 A1 | 1/2015 | Bajic |
| 2015/0048255 A1* | 2/2015 | Jarrell ............... H01J 49/0454 250/424 |
| 2015/0087003 A1 | 3/2015 | Charles et al. |
| 2015/0144782 A1 | 5/2015 | Fogwill et al. |
| 2015/0192590 A1 | 7/2015 | Sodeoka et al. |
| 2015/0201913 A1 | 7/2015 | Takats |
| 2015/0340215 A1 | 11/2015 | Pringle et al. |
| 2016/0002696 A1 | 1/2016 | Galiano |
| 2016/0133450 A1* | 5/2016 | Green ............... H01J 49/0031 250/282 |
| 2016/0215322 A1 | 7/2016 | Goodlett et al. |
| 2016/0247668 A1 | 8/2016 | Szalay et al. |
| 2016/0341712 A1 | 11/2016 | Agar |
| 2016/0372313 A1 | 12/2016 | Brown et al. |
| 2017/0103880 A1 | 4/2017 | Syage |
| 2018/0047551 A1 | 2/2018 | Jones et al. |
| 2018/0047555 A1 | 2/2018 | Pringle et al. |
| 2018/0053644 A1 | 2/2018 | Jones et al. |
| 2018/0136091 A1 | 5/2018 | Ryan et al. |
| 2018/0254177 A1 | 9/2018 | Gao et al. |
| 2018/0256239 A1 | 9/2018 | Johnson et al. |

FOREIGN PATENT DOCUMENTS

| | | | |
|---|---|---|---|
| CA | 2882003 A1 | 2/2014 | |
| CN | 1672238 A | 9/2005 | |
| CN | 101073137 A | 11/2007 | |
| CN | 101170043 A | 4/2008 | |
| CN | 101178381 A | 5/2008 | |
| CN | 101223625 A | 7/2008 | |
| CN | 101288146 A | 10/2008 | |
| CN | 101372502 A | 2/2009 | |
| CN | 101413905 A | 4/2009 | |
| CN | 101490524 A | 7/2009 | |
| CN | 201266145 Y | 7/2009 | |
| CN | 101657158 A | 2/2010 | |
| CN | 101819179 A | 9/2010 | |
| CN | 101871914 A | 10/2010 | |
| CN | 102026709 A | 4/2011 | |
| CN | 102121921 A | 7/2011 | |
| CN | 102137618 A | 7/2011 | |
| CN | 102164675 A | 8/2011 | |
| CN | 102169791 A | 8/2011 | |
| CN | 102264404 A | 11/2011 | |
| CN | 102367424 A | 3/2012 | |
| CN | 102445544 A | 5/2012 | |
| CN | 102483369 A | 5/2012 | |
| CN | 102768236 A | 11/2012 | |
| CN | 102800553 A | 11/2012 | |
| CN | 102879453 A | 1/2013 | |
| CN | 102924993 A | 2/2013 | |
| CN | 102928610 A | 2/2013 | |
| CN | 103295873 A | 9/2013 | |
| CN | 103335984 A | 10/2013 | |
| CN | 103426712 A | 12/2013 | |
| CN | 103597574 A | 2/2014 | |
| CN | 103748233 A | 4/2014 | |
| CN | 103776812 A | 4/2014 | |
| CN | 104062348 A | 9/2014 | |
| CN | 104254772 A | 12/2014 | |
| CN | 104254901 A | 12/2014 | |
| CN | 10428984 A | 1/2015 | |
| CN | 104582616 A | 4/2015 | |
| EP | 0169469 A2 | 1/1986 | |
| EP | 0437358 A2 | 7/1991 | |
| EP | 1855306 A1 | 5/2006 | |
| EP | 1730519 B1 | 7/2010 | |
| EP | 3265817 A1 | 1/2018 | |
| EP | 3266035 A1 | 1/2018 | |
| EP | 3265818 B1 | 2/2020 | |
| GB | 2425178 A | 10/2006 | |
| GB | 2420008 B | 9/2010 | |
| GB | 2491486 A | 12/2012 | |
| JP | S63243864 A | 10/1988 | |
| JP | 03001435 A | 1/1994 | |
| JP | H0785834 A | 3/1995 | |
| JP | H07130325 A | 5/1995 | |
| JP | H10247472 A | 9/1998 | |
| JP | H1164283 A | 3/1999 | |
| JP | 2000097913 A | 4/2000 | |
| JP | 10302710 A | 5/2000 | |
| JP | 2000180413 A | 6/2000 | |
| JP | 2001183345 A | 7/2001 | |
| JP | 2002170518 A | 6/2002 | |
| JP | 2004264043 A | 9/2004 | |
| JP | 2005205181 A | 8/2005 | |
| JP | 2006329710 A | 12/2006 | |
| JP | 2007-51934 A | 3/2007 | |
| JP | 2007170870 A | 7/2007 | |
| JP | 2007218916 A | 8/2007 | |
| JP | 2010169454 A | 8/2010 | |
| JP | 2014515831 A | 7/2014 | |
| JP | 2015503109 A | 1/2015 | |
| JP | 2015504160 A | 2/2015 | |
| KR | 20020013544 A | 4/2007 | |
| WO | 9734534 A1 | 9/1997 | |
| WO | 0160265 A1 | 8/2001 | |
| WO | 2008148557 A2 | 12/2008 | |
| WO | 2010075265 A2 | 7/2010 | |
| WO | 2010136887 A1 | 12/2010 | |
| WO | 2011114902 A1 | 9/2011 | |
| WO | 2012143737 A1 | 10/2012 | |
| WO | 2012164312 A2 | 12/2012 | |
| WO | 2012174437 A1 | 12/2012 | |
| WO | 2013098642 A2 | 7/2013 | |
| WO | 2013102670 A1 | 7/2013 | |
| WO | WO-2013098645 A2 * | 7/2013 | ......... G01N 30/7253 |
| WO | 2013/148162 | 10/2013 | |
| WO | 2014/106165 A1 | 7/2014 | |
| WO | 2014128629 A1 | 8/2014 | |
| WO | 2014139018 A1 | 9/2014 | |
| WO | 2014140601 A1 | 9/2014 | |
| WO | 2014142926 A1 | 9/2014 | |
| WO | 2014202828 A1 | 12/2014 | |
| WO | WO-2015004457 A1 * | 1/2015 | ......... H01J 49/0031 |
| WO | 2015132579 A1 | 9/2015 | |
| WO | 2016046748 A1 | 3/2016 | |
| WO | 2016142674 A1 | 9/2016 | |
| WO | 2016156615 A1 | 10/2016 | |
| WO | 2018142091 A2 | 8/2018 | |

OTHER PUBLICATIONS

Balog, et al ("Identification of Biological Tissues by Rapid Evaporative Ionization Mass Spectrometry" Anal. Chem. 2010, 82, 7343-7350). (Year: 2010).*

Agar, Nathalie et al., "*Development of Stereotactic Mass Spectrometry for Brain Tumor Surgery*", Biosis, Neurosurgery Online, vol. 68, No. 2, (2011).

(56) References Cited

OTHER PUBLICATIONS

Ahlf, Dorothy R. et al., "Correlated Mass Spectrometry Imaging and Confocal Raman Microscopy for Studies of Three-Dimensional Cell Culture Sections", Analyst, vol. 139, No. 18, pp. 4578 (2014).
Azimzadeh, Omid et al., "Formalin-Fixed Paraffin-Embedded (FFPE) Proteome Analysis Using Gel-Free and Gel-Based Proteomics", Journal of Proteome Research, vol. 9, No. 9, pp. 4710-4720 (2010).
Balgley, Brian M. et al., "Evaluation of Archival Time on Shotgun Proteomics of Formalin-Fixed and Paraffin-Embedded Tissues", Journal of Proteome Research, vol. 8, No. 2, pp. 917-925 (2009).
Balog, Julia et al., "Identification of Biological Tissues by Rapid Evaporative Ionization Mass Spectrometry", Analytical Chemistry, vol. 82, No. 17, pp. 7343-7350 (2010).
Balog, Julia et al., "Supporting Information for Identification of Biological Tissues by Rapid Evaporative Ionization Mass Spectrometry", pp. S1-S9, http://pubs.acs.org/doi/suppl/10.1021/ac101, (2013).
Balog, J. et al., "Intraoperative Tissue Identification Using Rapid Evaporative Ionization Mass Spectrometry", Science Translational Medicine, vol. 5, No. 194, pp. 194ra93 (2013).
Balog, J. et al., "Supplementary Materials: Intraoperative Tissue Identification Using Rapid Evaporative Ionization Mass Spectrometry", Science Translational Medicine, vol. 5, No. 194, pp. 194ra93 (2013).
Bean, Heather D. et al., "Bacterial Volatile Discovery Using Solid Phase Microextraction and Comprehensive Two-Dimensional Gas Chromatographytime-of-Flight Mass Spectrometry", Journal of Chromatography B, vol. 901, pp. 41-46 (2012).
Bellet, V. et al., "Proteomic Analysis of RCL2 Paraffin-Embedded Tissues", Journal of Cellular and Molecular Medicine, vol. 12, No. 5B, pp. 2027-2036 (2008).
Bocklitz, T.W. et al., "Deeper Understanding of Biological Tissue: Quantitative Correlation of MALDI-TOF and Raman Imaging", Analytical Chemistry, vol. 85, No. 22, pp. 10829-10834 (2013).
Cole, Laura M. et al., "Mass Spectrometry Imaging for the Proteomic Study of Clinical Tissue", Proteomics-Clinical Applications, vol. 9, No. 3-4, pp. 335-341 (2015).
Crawshaw, Benjamin et al., "Gastrointestinal Surgery: Real-Time Tissue Identification During Surgery", Nature Review/Gastroenterology & Hepatology Nature, vol. 10, No. 11. pp. 624-625.
Cselik, Z. et al., "Impact of Infrared Laser Light-Induced Ablation at Different Wavelengths on Bovine Intervertebral Disc Ex Vivo: Evaluation with Magnetic Resonance Imaging and Histology", Lasers in Surgery and Medicine, vol. 44, No. 5, pp. 406-412 (2012).
Davies, T.J. et al., "Volatile Products from Acetylcholine as Markers in the Rapid Urine Test Using Head-Space Gas-Liquid Chromatography B: Biomedical Sciences and Applications", Journal of Chromatography, vol. 307, pp. 11-21 (1984).
European Commission, "ISD Report Summary", http://cordis.europa.eu/result/rcn/163435_e, (2016).
Fahy, Eoin, et al., "Lipid Classification, Structures and Tools", Biochimica at Biophysica Acta (BBA)—Molecular and Cell Biology of Lipids, vol. 1811, No. 11, pp. 637-647 (2011).
Gerbig, Stefanie et al., "Analysis of Colorectal Adenocarcinoma Tissue by Desorption Electrospray Ionization Mass Spectrometric Imaging", Analytical and Bioanalytical Chemistry, vol. 403, No. 8, pp. 2315-2325 (2012).
Golf, Ottmar et al., "Rapid Evaporative Ionization Mass Spectrometry Imaging Platform for Direct Mapping from Bulk Tissue and Bacterial Growth Media", Analytical Chemistry, vol. 87, No. 5, pp. 2527-2534 (2015).
Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).
Guenther, Sabine et al., "Electrospray Post-Ionization Mass Spectrometry of Electrosurgical Aerosols", Journal of The American Society for Mass Spectrometry, vol. 22, No. 11, pp. 2082-2089 (2011).

Gustafsson, Ove J.R. et al., "Proteomic Developments in the Analysis of Formalin-Fixed Tissue", Biochimica et Biophysica Acta, vol. 1854, No. 6, pp. 559-580.
Hobbs, S.K. et al., "Magnetic Resonance Image-Guided Proteomics of Human Glioblastoma Multiforme", Journal of Magnetic Resonance Imaging, vol. 18, pp. 530-536 (2003).
Hsu, Cheng-Chih et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).
Jarmusch, Alan K et al., "Detection of Strep Throat Causing Bacterium Directly from Medical Swabs by Touch Spray-Mass Spectrometry", Analyst, vol. 139, No. 19, pp. 4785 (2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959 (2016).
Lazova, Rossitza et al., "Imaging Mass Spectrometry-A New and Promising Method to Differentiate Spitz Nevi From Spitzoid Malignant Melanomas", American Journal of Dermatopathology, vol. 34, No. 1, pp. 82-90 (2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).
Lieuwe, D.J. et al., "Volatile Metabolites of Pathogens: A Systematic Review", PLoS Pathogens, vol. 9, No. 5, pp. 1003311.
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).
Mccullough, Bryan J. et al., "On-Line Reaction Monitoring by Extractive Electrospray Ionisation", Rapid Communications in Mass Spectrometry, vol. 25, No. 10, pp. 1445-1451 (2011).
Murray, Patrick R, "What Is New In Clinical Microbiology-Microbial Identification by MALDI-TOF Mass Spectrometry", Journal of Molecular Diagnostics, vol. 14, No. 5, pp. 419-423 (2012).
Nicholson, Jeremy K. et al., "Metabolic Phenotyping in Clinical and Surgical Environments", Nature, vol. 491, No. 7424 pp. 384-392 (2012).
Pirro, Valentina et al., "Direct Drug Analysis from Oral Fluid Using Medical Swab Touch Spray Mass Spectrometry", Analytica Chimica Acta, vol. 861, pp. 47-54.
Plata, N. et al., "Aerosols Sampling Using a New Cryogenic Instrument", Journal of Aerosol Science, vol. 37, No. 12, pp. 1871-1875 (2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).
Shane, Ellis R. et al., "Surface Analysis of Lipids by Mass Spectrometry: More Than Just Imaging", Progress in Lipid Research Pergamon Press, vol. 52, No. 4, pp. 329-353.
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionisation Mass Spectrometry", Chemical Communications, vol. 49, No. 55, pp. 6188 (2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).

(56) References Cited

OTHER PUBLICATIONS

Strittmatter, N. et al., "*Taxon-Specific Markers for the Qualitative and Quantitative Detection of Bacteria in Human Samples*", http://www.msacl.org/2015_US_Long_Abstract.

Tait, Emma et al., "*Identification of Volatile Organic Compounds Produced by Bacteria Using HS-SPME-GC-MS*", Journal of Chromatographic Sci, pp. 1-11.

Uribe, D.O. et al., "*Piezoelectric Self-Sensing System for Tactile Intraoperative Brain Tumor Delineation in Neurosurgery*", Proceedings of the 31$^{st}$ Annual International Conference of the IEEE Engineering in Medicine and Biology Society: Engineering the Future of BioMedicine, pp. 737-740 (2009).

Vander Wilp, W. et al., "*Lead in Micro-Samples of Whole Blood by Rhenium-Cup in-Torch Vaporization-Inductively Coupled Plasma-Atomic Emission Spectrometry (ITV-ICP-AES)*", Fresenius' Journal of Analytical Chemistry, vol. 368, No. 7, pp. 734-736 (2000).

Vircks, Kyle E. et al., "*Rapid Screening of Synthetic Cathinones as Trace Residues and in Authentic Seizures Using a Portable Mass Spectrometer Equipped with Desorption Electrospray Ionization*", Rapid Communications in Mass Spectrometry, vol. 26, No. 23, pp. 2665-2672 (2012).

Summons to Attend Oral Proceedings Pursuant to Rule 115(1) EPC of EP Application No. 12726643.5, dated Apr. 20, 2018, 7 pages.

Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.

Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.

Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.

Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.

Strittmatter, N.: "Home—Miss Nicole Strittmatter" Retrieved from the Internet URL: http://www.imperial.ac.uk/people/n.strittmatter12 [retrieved on May 19, 2016] the whole document.

Wehofsky, et al "Automated deconvolution and deisotoping of electrospray mass spectra" J. Mass Spectrom. 2002; 37: pp. 223-229.

Al Sahaf et al., "Chemical Composition of Smoke Produced by High-Frequency Electrosurgery", Irish Journal of Medical Science, vol. 176, No. 3, pp. 229-232, 2007.

Barrett et al., "Surgical Smoke: A Review of the Literature", Surgical Endoscopy, vol. 17, No. 6, pp. 979-987, 2003.

Down, "A DESI-Rable Ionization Revolutionizes Mass Spectrometry", Base Peak, 2005.

International Search Report and Written Opinion for International Application. No. PCT/IB2012/003009, dated Aug. 14, 2013, 17 pages.

PCT International Search Report and Written Opinion for International Appln. No. PCT/IB2010/001261, dated Sep. 21, 2010, 5 pages (MDMSS.00INP).

PCT International Search Report and Written Opinion for International Appln. No. PCT/IB2012/002995, dated Sep. 10, 2013, 3 pages (MDMSS.005WO).

Qiao et al., "Electrostatic-Spray Ionization Mass Spectrometry", Analytical Chemistry, vol. 84, No. 17, pp. 7422-7430, 2012.

Na, et al., "Development of a Dielectric Barrier Discharge Ion Source for Ambient Mass Spectrometry", Journal of The American Society for Mass Spectrometry, Elsevier Science Inc, vol. 18, No. 10, pp. 1859-1862, Sep. 20, 2007.

Lee et al., "Thermally Assisted Electrospray Interface for Liquid Chromatography/Mass Spectrometry", Rapid Communications in Mass Spectrometry, vol. 6, pp. 727-733, 1992.

McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.

Sakairi et al., "Characteristics of a Liquid Chromatograph/ Atmospheric Pressure Ionization Mass Spectrometer", Anal. Chem., vol. 60, pp. 774-780, 1988.

Takats et al., "Characterization of DESI-FTICR Mass Spectrometry— From ECD to Accurate Mass Tissue Analysis", Journal of Mass Spectrometry, vol. 43, pp. 196-203, 2008.

Eagles, et al., "Fast Atom Bombardment Mass Spectrometry of Amine Mixtures", John Wiley & Sons, Ltd, 1988.

Slemr et al., Concentration Profiles of Diamines in Fresh and aerobically Stored Park and Beef, American Chemical Society, 1985.

Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).

Van Berkel, "Thin-Layer Chromatography and El3ectrospray Mass Spectrometry Coupled Using a Surface Sampling probe". Anal. Chem. 2002.

Takats et al., "Mass Spectrometry Sampling Under Ambient Conditions with Desorption Electrospray Ionization", Science, vol. 306, 2004.

Tottszer et al., "Laser Heating Versus Resistive Heating in the Field-Desorption Mass Spectrometry of Organic Polymers", J. Phys. D: Appl. Phys., vol. 21, pp. 1713-1720, 1988.

Hsu, et al., "Microscopy ambient ionization top-down mass spectrometry reveals developmental patterning", Proceedings of the National Academy of Sciences, vol. 110, No. 37, pp. 14855-14860, Aug. 22, 2013.

Zhou, X. et al., "Development of miniature mass spectrometry systems for bioanalysis outside the conventional laboratories." Bioanalysis, 6 (11) 1497-1508 (2014).

Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).

McJimpsey, E.L., et al., "Parameters Contributing to Efficient Ion Generation in Aerosol MALDI Mass Spectrometry," American Society for Mass Spectrometry pp. 1044-0305 (2007).

Mutters, N.T., et al., "Performance of Kiestra Total Laboratory Automation Combined with MS in Clinical Microbiology Practice," Annals of Laboratory Medicine 34: 111-117 (2014).

Longuespée, R., et al., Tissue Proteomics for the Next Decade? Towards a Molecular Dimension in Histology, OMICS A Journal of Integrative Biology 28(9): 539-552 (2014).

Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).

Suarez, S. et al., Ribosomal proteins as biomarkers for bacterial identification by mass spectrometry in the clinical microbiology laboratory, Journal of microbiological Methods, 94: 390-396 (2013).

Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).

Cha, S. Laser desorption/ionization mass spectrometry for direct profiling and imaging of small moledcules from raw biological materials, Doctoral Dissertation, Iowa State University (2008).

Asano et al., "Self-aspirating atmospheric pressure chemical ionization source for direct sampling of analytes on Surfaces in liquid solution", Rapid Communications in Mass Spectrometry 2005.

International Search Report and Written Opinion for application No. PCT/GB2017/051050, dated Jun. 27, 2017, 15 pages.

Gerbig, Stefanie et al, "Spatially resolved investigation of systemic and contact pesticides in plant material by desorption electrospray ionization mass spectrometry imagine", Analytical and Bioanalytical Chemistry, 407 (24):7379-7389 (2015).

(56) References Cited

OTHER PUBLICATIONS

Lesiak, A., et al., "Rapid detection by direct analysis in real time-mass spectrometry (DART-MS) of psychoactive plant drugs of abuse: the case of Mitragyna speciosa aka "Kratom"", 242:210-218 (2014).

Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).

Nielen, M et al., "Desorption electrospray ionization mass spectrometry in the analysis of chemical food contaminants in food", Trac Trends in Analytical Chemistry, 30(2):165-180 (2011).

Boughton, B. et al., "Mass spectrometry imaging for plant biology: a review", Phytochemistry Reviews, 15(3):445-488 (2015).

Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.

International Search Report and Written Opinion for International Application No. PCT/GB2016/052956, dated Jan. 26, 2017, 16 pages.

Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.

Jackson, S. N. et al. On-line laser desorption/ionization mass spectrometry of matrix-coated aerosols, Rapid Communications in Mass Spectrometry, vol. 18, pp. 2041-2045 (Year 2004).

Dong, Y., et al., "Sample Preparation for Mass Spectrometry Imaging of Plant Tissues: A Review", Frontiers in Plant Science 7(60): 1-16 (2016).

Communication pursuant to Article 94(3) EPC, for application No. 16710788.7, dated Jun. 13, 2019, 9 pages.

Examination Report under Section 18(3), for application No. GB1714122.7, dated May 9, 2019, 6 pages.

Bagley, B.M., et al., "Evaluation of archival time on shotgun proteomics of formalin-fixed and paraffin-embedded tissues", Journal of Proteome Research 8(2):917-925, (2009).

Kohler, M. et al. "Characterization of lipid extracts from brain tissue and tumors using Raman spectroscopy and mass spectrometry," Anal Bioana Chem, 393:1513-1520, Jan. 20, 2009.

Harry, K. H., et al. "Effect of protein coating of flocked swabs on the collection and release of clinically important bacteria", Indian Journal of Medical Microbiology, 32(3):301-303 (2014).

Blais, B. W., "Swab-Based Enzyme Immunoassay System for Detection of Meat Residues on Food Contact Surfaces as a Hygiene Monitoring Tool", Journal of Food Protection, 62(4):386-389 (1999).

Farhat S. E. et al. "Efficacy of a Swab Transport System in Maintaining Viability of Neisseria gonorrhoeae and *Streptococcus pneumoniae*", Journal of Clinical Microbiology, 39(8):2958-2960 (2001).

Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.

Hachmoeller et al., "Element bioimaging of liver needle biopsy specimens from patients with Wilson's disease by laser ablation-inductively coupled plasma-mass spectrometry", Journal of Trace Elements in Medicine and Biology, 35:97-102, Feb. 10, 2016.

Guenther et al., "Spatially Resolved Metabolic Phenotyping of Breast Cancer by Desorption Electrospray Ionization Mass Spectrometry", Cancer Research, 75:1828-1837, Feb. 17, 2015.

Chipuk J. E. et al., "Transmission Mode Desorption Electrospray Ionization", Journal of the American Society for Mass Spectrometry, 19(11):1612-1620, Nov. 1, 2008.

Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.

Chen, H., et al., "What Can We Learn from Ambient Ionization Techniques?", Journal of The American Society for Mass Spectrometry, 20:1947-1963, (2009).

Sankaranarayanan, G., et al., "Common Uses and Cited Complications of Energy in Surgery", Surg Endosc., 27:3056-3072, (2013).

Rau, H.G., et al., "The use of water-jet dissection in open and laparoscopic liver resection", HPB, 10:275-280, (2008).

Chen, H., et al. "Desorption Electrospray Ionization Mass spectrometry for high-throughput analysis of Pharamaceutical samples in the ambient environment" Anal. Chem 77:6915-6927 (2005).

Vemury, S., and Pratsinis, S.E., "Charging and Coagulation During Flame Synthesis of Silica", Journal Aerosol Science 27(6):951-966 (1996).

Office Action for CN Patent Application No. 201680025801.0 dated Apr. 7, 2020.

Office Action for CN Patent Application No. 201680025801.0 dated Apr. 7, 2020 translation.

Adams, F., et al, "Inorganic Mass Spectrometry", copyright John Wiley & Sons, Inc. pp. 174-180 (1988).

Examination Report under Section 18(3), for application No. GB1715787.6, dated Jun. 1, 2020, 6 pages.

CNOA for application No. 201680026285.3 dated Jun. 12, 2020, 12 pages.

Panpradist, N., et al., "Swab Sample Transfer for Point-of-Care Diagnostics: Characterization of Swab types and Manual Agitation Methods", PLOS ONE 9(9):1-11 (2014).

Extended EP search report for EP Application No. 20172634.6, dated Sep. 14, 2020, 8 pages.

Partial European Search Report for EP20181905.9, dated Aug. 27, 2020, 15 pages.

Roddy, T., el al., "Imaging of Freeze-Fractured Cells with in Situ Fluorescence and Time-of-Flight Secondary Ion Mass Spectrometry", Analytical Chemistry 74(16):4011-4019(2002).

Petrotchenko, E.V., et al., "Combining Fluorescence Detection and Mass Spectrometric Analysis for Comprehensive and Quantitative Analysis of Redox-Sensitive Cysteines in Native Membrane Proteins", Analytical Chemistry 78(23):7959-7965 (2006).

Ablonczy, Z., et al., "The utilization of fluorescence to identify the components of lipofuscin by imaging mass spectrometry", Proteomics 14(7-8):936-944.

Enthaler, B., et al., "Improved sample preparation for MALDI-MSI of endogenous compounds in skin tissue sections and mapping of exogenous active coinpounds subsequent to ex-vivo skin penetration", Anal Bioanal Chem 402:1159-1167 (2012).

CNOA for application No. CN 201680025801.0 dated Oct. 12, 2020 for corresponding app original document and translation.

Adams, F., et al., "Inorganic Mass Spectrometry", (1993) Abstract.

Dong, Y.M.B.A., "Polymer Analysis Handbook", China Petrochemical Press (2004) 8 pages.

Waters DESI System Operators Guide 715004701/Revision A, Waters Corporation, [online] Jan. 2015.

Shin, Y-S., et al., "Desorption Electrospray Ionization-Mass Spectrometry of Protetins" Analytical Chemistry 79:3514-3518 (2007).

Search and Examination Report under Sections 17 and 18(3) for GB1715767.8, dated Nov. 26, 2020, 6 pages.

Chen, X., ed., "Liquid Chromatography-Mass Spectrometry—Chapter 8", in Principle and Application of Chromatographic Analysis Technology, Chinese Peoples Public Security University Press, (Jan. 2014) 6 pages.

Song, Y., et al., "Rapid ambient mass spectrometric profiling of intact, untreated bacteria using desorption electrospray ionization" ChemComm pp. 61-63 (20007).

Wiseman, J.M. and Li, J.B., "Elution, Partial Seperation, and Identification of Lipids Directly from Tissue Slices on Planar Chromatography Media by Desorption Electrospray Ionization Mass Spectrormetry", Anal Chem 82:8866-8874 (2010).

Examination Report under Section 18(3) for Application No. GB 201515580.0, dated Jan. 21, 2021, 4 pages.

Krousktotp, T., Ultrasonic Imaging, vol. 20, 1998, "Elastic moduli of breast and prostate tissues under compression" Ultrasonic Imaging 20:260-274 (1998).

(56) References Cited

OTHER PUBLICATIONS

Aberg, P., "Skin Cancer Identification Using Multifrequency Electrical Impedance—A Potential Screening Tool", IEEE Transactions on Biomedical Engineering, 51(12): 2097-2102 (2004).
Extended European Search Report for Application No. 20210062.4, dated Mar. 9, 2021, 13 pages.
Rath, C.M., et al., "Molecular Analysis of Model Gut Microbiotas by Imaging Mass Spectrometry and Nanodesorption Electrospray Ionization Reveals Dietary Metaboite Transformations" Analytical Chemistry 84(21):9259-9267 (2012).
Fenselau, C.C., "Rapid Characterization of Microorganisms by Mass Spectrometry—What Can Be Learned and How?" Journal of the American Society for Mass Spectrometry 24(8):1161-1166 (2013).
Uetrecht, C. et al., "Modern Biomolecular Mass Spectrometry and its Role in Studying Virus Structure, Dynamics and Assembly" Angewandte Chemie International Edition 50(36):8248-8262 (2011).
Forbes, T.P. et al., "Chemical imaging of artificial Fingerprints by desorption electro-flow focusing ionization mass spectrometry" Analyst 139(12):2982-2985 (2014).
Examination Report for GB Application No. 201515580.0, dated Mar. 12, 2021, 4 pages.
Cornett, D. S., et al, "A Novel Hisology-directed Strategy for MALDI-MS Tissue Profiling That Improves Throughput and Cellular Specificity in Human Breast Cancer", American Society for Biochemistry and Molecular Biology, p. 1975-19983, Jul. 18, 2006.
Examination Report under Section 18(3) for Application No. GB1714165.6, dated Mar. 22, 2021, 6 pages.
Examination Report under Section 18(3) for Application No. GB1715750.4, dated Mar. 22, 2021, 5 pages.
Hillenkamp, F., et al., "Matrix-Assisted Laser Desorption/Ionization Mass Spectrometry of Biopolymers", Anal Chem 63(24): 1193A-1203A (1991).
Hrabak, J., et al., "Matrix-Assisted Laser Desorption Ionization—Time of Flight (MALDITOF) Mass Spectrometry for Detection of Antibiotic Resistance Mechanisms: from Research to Routine Diagnosis", CMR Journal 26(1): 103-114 (2013).
CNOA for Application No. 201680026939.2, dated Apr. 27, 2021, original 10 pp.
Combined Search and Examination Report under Sections 17 and 18(3), for Application No. GB2110454.2, dated Aug. 19, 2021, 9 pages.
Office Action for Chinese application No. 20191104563.7, dated Oct. 11, 2021, original document 14 pages.
Examination Report under Section 18(3) for Application No. GB1715750.4, dated Oct. 11, 2021, 5 pages.
Chen Liru, "Ambient Mass Spectrometry for Fast Identification of Lung Cancer", Chinese Doctoral Dissertations Masters Theses Full-text Database (Master) Medicine and Health Sciences—Nanchang University Jun. 7, 2014, original document and translation.
Chinese office action for application No. 201910350273.1, dated Dec. 3, 2021, original document 19 pages.
Chinese office action for application No. CN202010611251.9, dated Dec. 10, 2021, original document 8 pages.

* cited by examiner

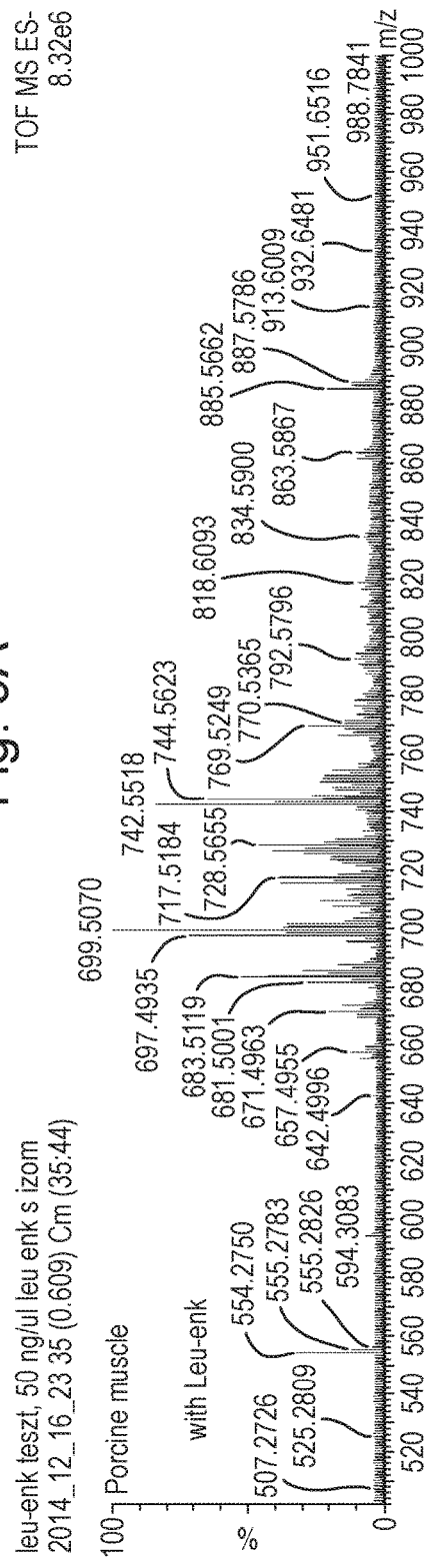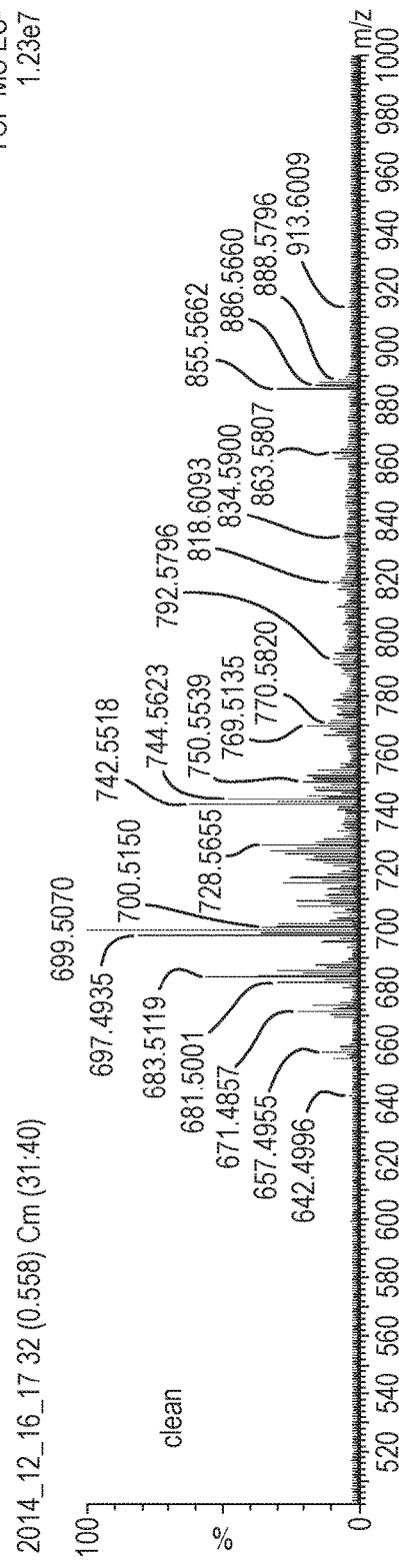

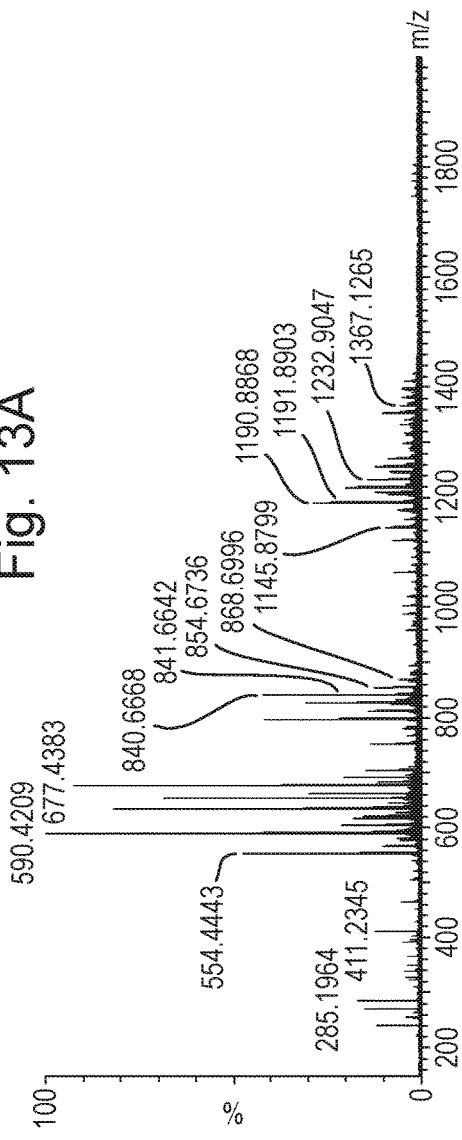
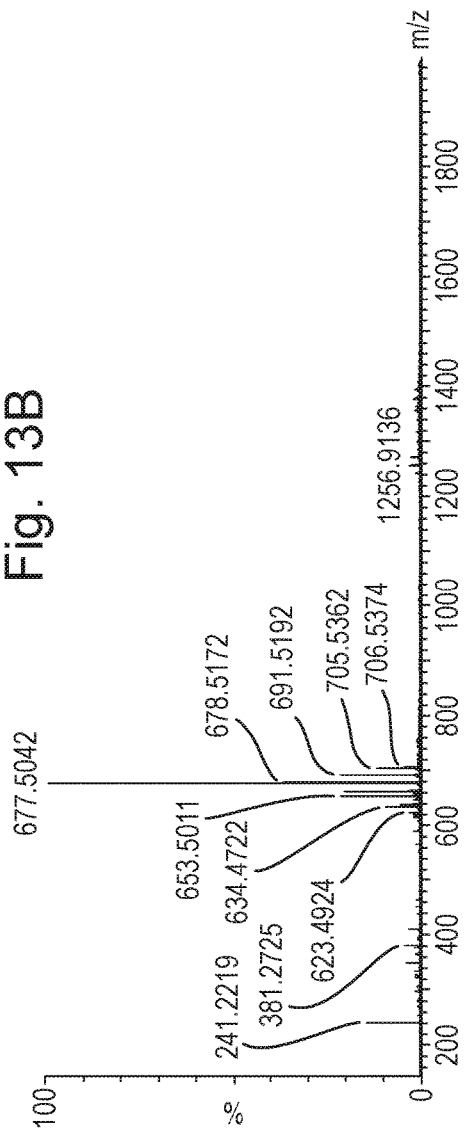

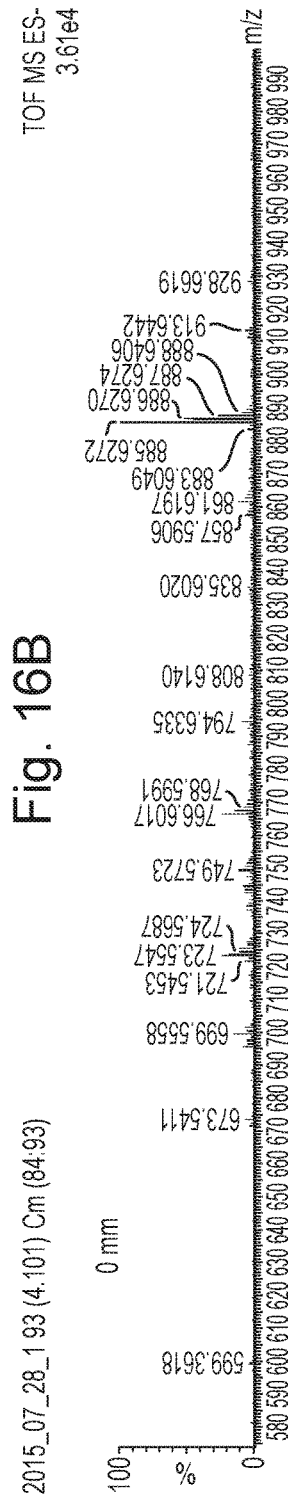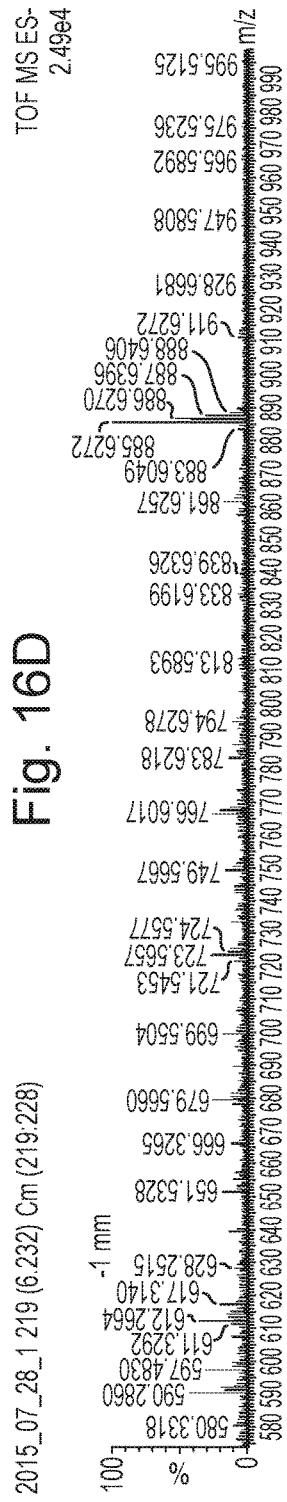

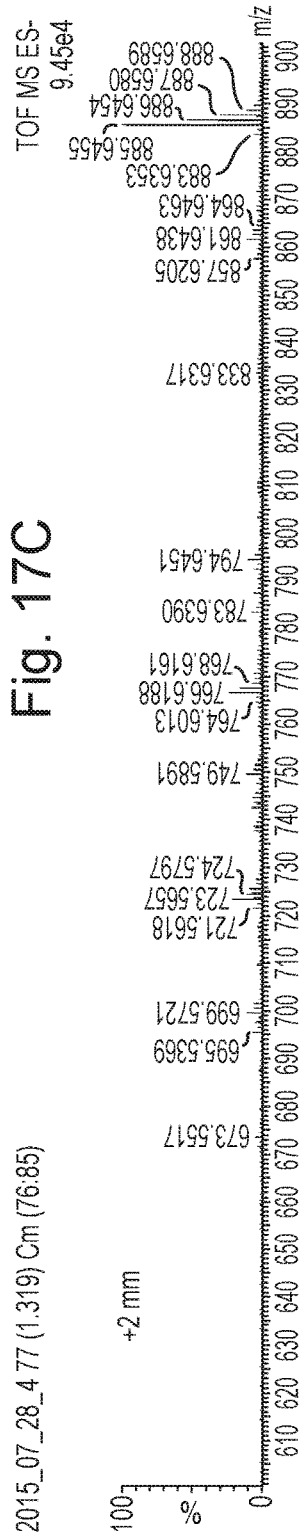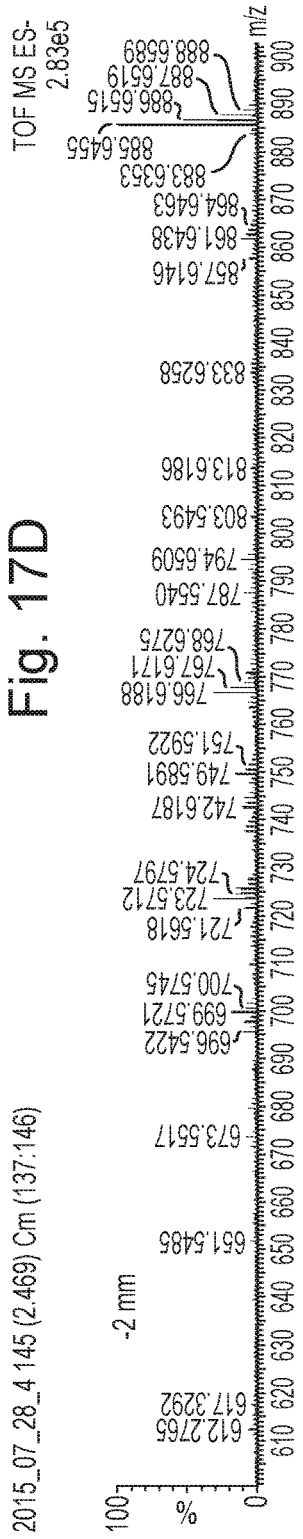

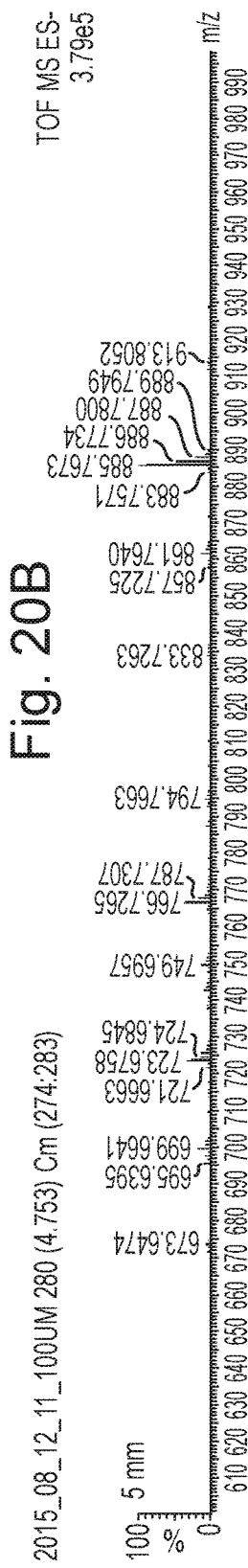
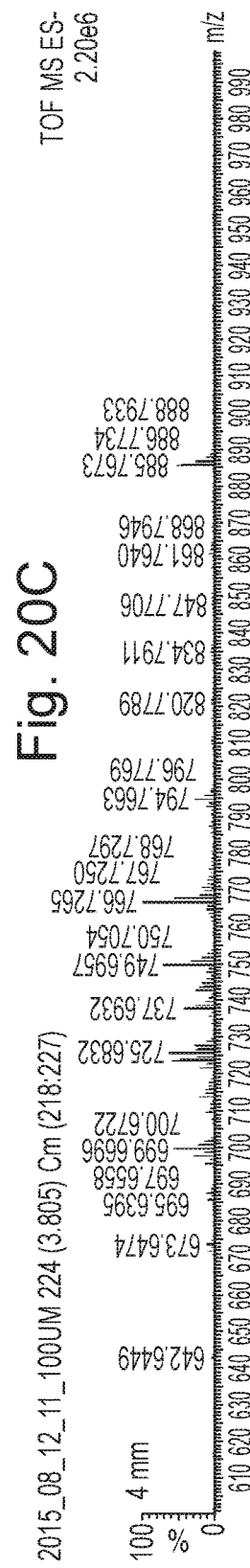
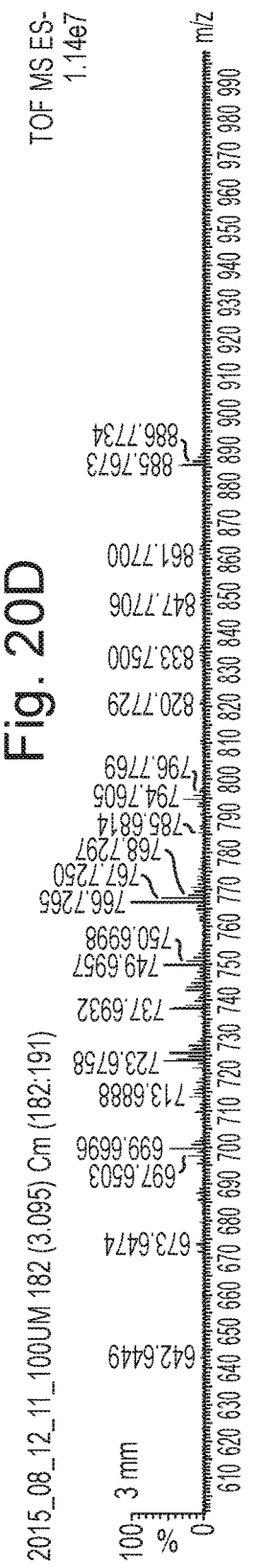
Fig. 20B
Fig. 20C
Fig. 20D

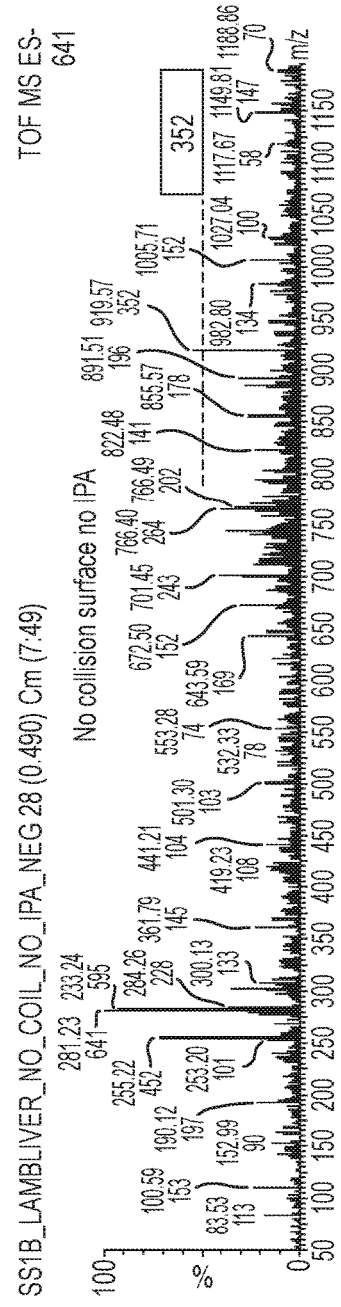
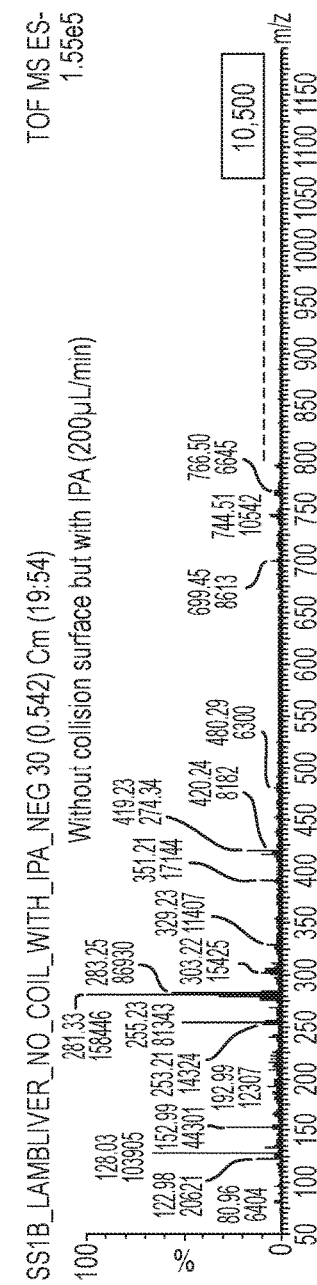
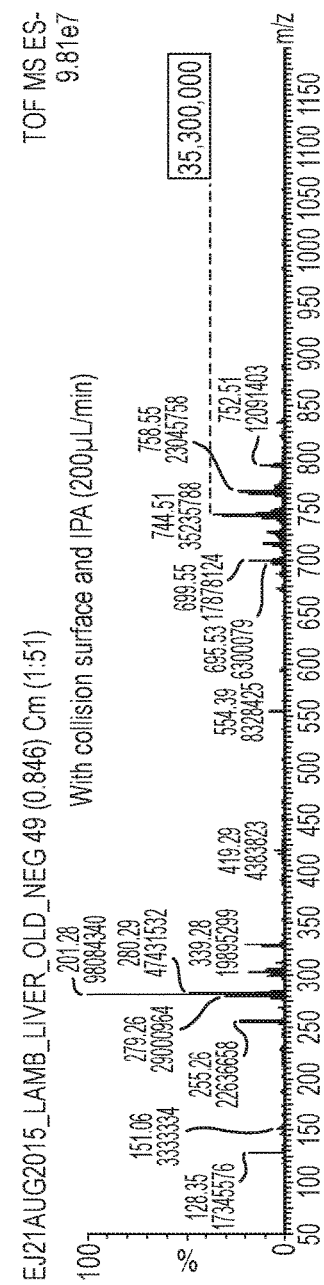

Fig. 24A  Fibrous tissue

Fig. 24B  Breast tissue with optimum IPA settings / Breast tissue no IPA

IONISATION OF GASEOUS SAMPLES

CROSS-REFERENCE TO RELATED APPLICATION

This application represents the U.S. National Phase of International Application number PCT/GB2016/050612 entitled "Improved Ionisation of Gaseous Samples" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention generally relates to mass spectrometry, and in particular, to apparatus for improving the ionisation of a sample. Embodiments relate to rapid evaporative ionisation mass spectrometry, mass spectrometers, ion mobility spectrometers, hybrid ion mobility mass spectrometers, methods of rapid evaporative ionisation mass spectrometry ("REIMS"), methods of mass spectrometry, methods of ion mobility, methods of hybrid ion mobility mass spectrometry, methods of electrosurgery and electrosurgical devices.

BACKGROUND

Rapid evaporative ionization mass spectrometry ("REIMS") is a technology which has recently been developed for the real-time identification of substrates, for example for the identification of biological tissues during surgical interventions. REIMS analysis of biological tissues has been shown to yield phospholipid profiles having high histological and histopathological specificity, similar to Matrix Assisted Laser Desorption Ionisation ("MALDI"), Secondary Ion Mass Spectrometry ("SIMS") and Desorption Electrospray Ionisation ("DESI") imaging.

Coupling of REIMS technology with handheld sampling devices has resulted in iKnife sampling technology, which can provide intra-operative tissue identification. This technology allows surgeons to resect target tissues more efficiently, such as tumours, intra-operatively by providing information that can assist a surgeon in minimizing the amount of healthy tissue removed whilst helping to resect the target tissue. iKnife sampling technology can also be used by non-surgical operators in non-surgical procedures to isolate target matter from an in vitro substrate.

In a known iKnife sampling system, a mass spectrometric signal is obtained by subjecting a substrate to alternating electric current at radiofrequency which causes localized Joule-heating and the disruption of cells along with desorption of charged and neutral particles. The resulting aerosol (e.g., "surgical smoke") is directly introduced into an atmospheric interface of an atmospheric pressure ionisation mass spectrometer for on-line mass spectrometric analysis. The aerosol contains a sufficient number of ionised molecules to allow the direct mass spectrometric fingerprinting of the biological tissues.

Post-evaporative ionisation of neutrals molecules in the sample may be used to enhance the ion yield. In this regard, electrospray and corona discharge post-ionisation methods were tested. Secondary electrospray ionisation, fused droplet electrospray ionisation and extractive electrospray ionisation have been used to increase the ion yield. These three techniques are similar in the sense that electrically charged solvent droplets are fused with aerosol particles in the gas phase and the resulting fused droplets undergo an electrospray-like ionisation process. However, these techniques suffer from the delicateness of electrospray setup, the sample carryover effects caused by DESI-like phenomena, electrospray-related restrictions on solvent type and flow rates, and patient safety considerations in human interventional environments due to the high voltages involved in these techniques.

It is also possible to enhance ionisation by facilitating the collision of the aerosol particles with a collision surface in the vacuum region of the mass spectrometer. A collisional ion generator method was developed and is disclosed in WO 2013/098642 (Medimass) in which the aerosol particles enter the analyser at the atmospheric interface and are accelerated into the vacuum region of the analyser in the free jet regime. The aerosol particles accelerated by the free jet are then directed onto a collision surface, causing the ion yield of the REIMS method to be enhanced.

However, despite this enhancement, a number of problems still remain. For example, the ionisation yield for this technique remains relatively low. Also, there may be a lack of ionisation or suppression of analyte ion formation when electrosurgical diathermy is used in a coagulation mode. Also, there may be a lack of ionisation when tissue having a high neutral lipid content, such as triglycerides or diglycerides, is being dissected (e.g., adipose tissue or breast tissue).

It is therefore desired to provide an improved method and apparatus.

SUMMARY

According to a first aspect there is provided a method mass spectrometry and/or ion mobility spectrometry comprising:

providing an analyte;

supplying a matrix compound to said analyte such that said analyte is diluted or dissolved in, or forms first clusters with said matrix; and colliding said first clusters or first droplets of said diluted or dissolved matrix with a collision surface.

WO 2013/098642 describes a method of generating and analysing an aerosol sample. The aerosol sample generated comprises droplets that are covered with polar lipids. During analysis, the droplets are accelerated by free jet expansion in the atmospheric inlet of a mass spectrometer such that the droplets attain a high velocity and then impact onto a collision surface. This results in the production of gaseous ions of the polar lipid molecules. However, the ionisation yield of this technique is relatively low.

It has been recognised that the ion yield in this method is relatively low due to the poor conversion rate of the droplets into individual molecular species, mostly caused by the strong intermolecular bonds between the analyte molecules.

According to embodiments of the present invention, the analyte is diluted by the matrix or dissolved into the matrix.

For example, the analyte may be in provided in the form of droplets, aerosol or liquid and may be fused or coalesced with the matrix, or dissolved into the matrix. The matrix may be in the form of droplets, solids, aerosol or liquid when in contact with the analyte. Diluting, or dissolving the analyte in the matrix, may substantially eliminate or reduce intermolecular bonding between the analyte molecules. As such, when the diluted or dissolved analyte droplet is subsequently collided with the collision surface it fragments into smaller droplets, wherein any given smaller droplet is likely to contain fewer analyte molecules than it would if the matrix were not present. This leads to the more efficient generation of analyte ions.

It is thought that ionisation of the analyte predominantly occurs due to ionic dissociation of the analyte in the solution phase, due to interactions with counter ions present in the sample being analysed. Diluting or dissolving the analyte in the matrix reduces the concentration of the analyte in each droplet and facilitates ionic dissociation in the solution phase, thus ultimately resulting in a greater proportion of the analyte being ionised. Accordingly, any matrix that dissolves or dilutes the analyte may be used.

According to the various embodiments described herein, the step of colliding said first clusters or droplets with the collision surface may fragment the first clusters or droplets into a plurality of second smaller clusters or droplets. However, other embodiments are contemplated wherein other forms of droplet dissociation or disintegration are used such as, for example, laser irradiation, ultrasonic energy, glow discharge or photoionization etc.

The step of providing the analyte may comprise providing the analyte in the form of a gas-phase analyte, aerosol, vapour, smoke or liquid; and/or said matrix may be supplied to said analyte whilst said analyte is in the form of a gas-phase analyte, aerosol, vapour, smoke, solid or liquid.

The method may form the first droplets by supplying the matrix to the analyte whilst the analyte is in the form of an aerosol, vapour or smoke and whilst the matrix is in the form of an aerosol, vapour or solid.

The step of supplying the matrix to the analyte may comprise supplying matrix molecules to, and intermixing said matrix molecules with, said analyte whilst said matrix is in a gas phase or in the form of an aerosol, vapour or solid.

The mixture of said analyte and said matrix may be transferred from a high pressure region to a low pressure region such that said gas phase matrix cools and condenses to a liquid and said analyte dissolves in, or is diluted by, said liquid matrix so as to form said first droplets.

Alternatively, the matrix may be supplied to, and intermixed with, the analyte as a liquid.

If the analyte and/or matrix is in liquid form then the analyte and/or matrix may be converted into droplets or vapour, e.g., by spraying or nebulising. For example, if the analyte and matrix are mixed as liquids then the mixture may subsequently be converted into the first analyte droplets, e.g., by spraying or nebulising.

The matrix may initially be supplied as a solid (e.g., a powder) and sublimated or melted and evaporated so as to form matrix in vapour or gas-phase that is intermixed with the analyte. For example, a solid matrix may be mixed with the analyte. If the analyte is mixed in liquid form, the mixture may be allowed to dry, e.g., to form crystals. The mixture may then be heated to sublimate and/or evaporate the matrix and/or analyte. Examples of suitable matrices include MALDI matrices and other matrices, such as: coumarin; 9-aminoacridine; 2,5-dihydroxybenzoic acid; THAP; CHCA; and quecertin.

The matrix may be selected from the group consisting of: (i) a solvent for said analyte; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; and (xxiii) propanol.

By way of example, for analytes comprising polar lipids, low molecular weight alcohols may be used as the matrix (e.g., methanol, ethanol, isopropanol) or ketones (e.g., acetone). These matrices have been shown to enhance the ionisation of species otherwise detected in the absence of the matrix vapours at lower intensity.

A protic matrix solvent may be used, e.g., for the analysis of lipids or triglycerides. Alternatively, a non-protic or aprotic matrix solvent may be used, e.g., for the analysis of proteins.

The mixture of analyte and matrix may be a homogeneous or heterogeneous mixture.

The matrix and/or analyte may be doped with one or more additives for enhancing the solvation of the analyte in the matrix or for enhancing the ionisation of the analyte.

The matrix or analyte may be doped with an acidic or basic additive. For example, the matrix may be doped with formic acid, diethylamine.

The matrix may cause derivatisation of the analyte. For example, the matrix may cause the derivatisation of cholesterol or steroids in the analyte. This may render the analyte more easily ionised.

The method may comprise adding a calibrant to the matrix and/or analyte, or selecting a compound in the matrix and/or analyte as a calibrant, and using the calibrant to calibrate the method of mass spectrometry and/or ion mobility spectrometry. This is particularly useful in ambient ionisation techniques such as REIMS techniques, in which it may be difficult to introduce calibrants according to conventional techniques.

The method may comprise analysing a lock mass species, e.g. by adding the lockmass species to the matrix and/or analyte. The lockmass may then be used to correct the mass(es) of analyte(s). Alternatively, or additionally, the method may comprise analysing a lock mobility species, e.g. by adding the lock mobility species to the matrix and/or analyte. The lock mobility species may then be used to correct the mobilities or drift time(s) of analyte(s).

The step of colliding said first clusters or first droplets with said collision surface may comprise accelerating said first clusters or first droplets onto said collision surface.

The step of accelerating said first clusters or first droplets onto said collision surface may comprise using a pressure differential to accelerate said first clusters or first droplets onto said collision surface.

A vacuum pump may be used to create a pressure differential between a first region and a second region for accelerating the first clusters or first droplets between the two regions and onto the collision surface. The apparatus may comprise a mass spectrometer and/or ion mobility spectrometer having an atmospheric interface arranged between the first and second regions, wherein the second region may comprise a vacuum chamber that is connected to the vacuum pump and which houses the collision surface.

The combination of gas flow between the first and second regions (e.g., into the spectrometer) and matrix flow may nebulise the matrix, producing droplets of the appropriate diameter/volume. The nebulising gas flow may produce a shear force on the matrix, producing droplets that enter the sample transfer tube.

The method may comprise evaporating the matrix from the analyte in the second clusters or droplets, resulting in free analyte ions that are separate from said matrix.

The step of colliding the first clusters or first droplets with the collision surface may evaporate the matrix from the analyte by converting kinetic energy of the analyte and matrix into heat.

The step of colliding the first clusters or first droplets causes the second smaller clusters or droplets to be generated, at least some of which may have only a single analyte molecule therein. This enhances the ionisation process.

The dielectric constant of the matrix may be sufficiently high such that the solvation of the analyte in the matrix involves ionic dissociation resulting in solvated ions of the analyte present in the condensed phase. In these cases, the impact on the collision surface is more likely to produce solvated ions in the gas phase, which may eventually yield ions formed by deprotonation (in a negative ion mode, i.e. [M−H]$^-$), ions formed by protonation (in a positive ion mode, i.e. [M+H]$^+$), and/or molecular ions. Alternatively, or additionally, ions may be formed by any one of: dehydration, deamidation or alkaline metal adducts.

The method may comprising subjecting said analyte or analyte ions to ionisation downstream of said collision surface. Optionally, the ionisation is performed by an ionisation source selected from the group consisting of: a corona discharge ionisation source; a reagent ion Ionisation source; a Photo Ionisation source; a Chemical Ionisation source; an Electron Impact ("EI") ionisation source; a Field Ionisation ("FI") source; a Field Desorption ("FD") Ionisation source; an Inductively Coupled Plasma ("ICP") Ionisation source; a Fast Atom Bombardment ("FAB") Ionisation source; a Liquid Secondary Ion Mass Spectrometry ("LSIMS") Ionisation source; a Desorption Electrospray Ionisation ("DESI") Ionisation source; a Nickel-63 radioactive Ionisation source; a Thermospray Ionisation source; an Atmospheric Sampling Glow Discharge Ionisation ("ASGDI") Ionisation source; a Glow Discharge ("GD") Ionisation source; an Impactor Ionisation source; a Direct Analysis in Real Time ("DART") Ionisation source; a Laserspray Ionisation ("LSI") source; a Sonicspray Ionisation ("SSI") source; a Matrix Assisted Inlet Ionisation ("MAII") source; a Solvent Assisted Inlet Ionisation ("SAII") source; a Desorption Electrospray Ionisation ("DESI") source; a desorption electroflow focusing ionisation ("DEFFI") source; a Laser Ablation Electrospray Ionisation ("LAESI") source; and a Surface Assisted Laser Desorption Ionisation ("SALDI") source.

The method may comprise trapping the analyte ions in an ion trap and/or guiding the analyte ions using an ion guide.

The method may comprise heating said collision surface.

The method may comprise heating said collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may comprise supplying said matrix to said analyte via a matrix introduction conduit, and analysing ions of the analyte using an ion analyser arranged downstream of an outlet of said matrix introduction conduit.

The distance x between said outlet of said matrix introduction conduit and an inlet of said ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about ≤6 mm; (xiv) about ≤5.5 mm; (xv) about ≤5 mm; (xvi) about ≤4.5 mm; (xvii) about ≤4 mm; (xviii) about ≤3.5 mm; and (xix) about ≤3 mm.

It is contemplated that the distance x may be selected from the group consisting of: about 6.0-6.5 mm; about 6.5-7.0 mm; about 7.0-7.5 mm; about 7.5-8.0 mm; about 8.0-8.5 mm; about 8.5-9.0 mm; about 9.0-9.5 mm; about 9.5-10.0 mm; about 0.1-10 mm; about 0.1-7.5 mm; about 0.1-5.1 mm; about 0.5-5.1 mm; and about 0.5-5.0 mm.

The ion analyser may comprise a vacuum chamber into which the inlet opens. The inlet of the ion analyser may be determined to be a region that is at the pressure of the vacuum chamber. For example, if the inlet is provided by an elongated tube then the distance x may be determined from the position in the tube that is at the pressure of the vacuum chamber. Alternatively, or additionally, the inlet may be determined to be the entrance and/or exit of an inlet tube or orifice.

The matrix introduction conduit may have an exit opening substantially facing or opposite the inlet of said ion analyser; and/or the exit opening of the matrix introduction conduit may be substantially coaxial with the inlet of said ion analyser.

The outlet of the matrix introduction conduit and the inlet of said ion analyser may be spaced apart and not connected by a completely enclosed conduit.

The exit of the matrix introduction conduit and the inlet of the ion analyser may be interconnected by a sampling tube having an opening in its circumference for receiving the analyte through the opening.

The method may comprise delivering the analyte through a sample transfer conduit, wherein the analyte is arranged to impact on an upstream side of the sampling tube and then flow around the outside of the sampling tube and into said opening in a downstream side of the sampling tube.

The outlet of the sample transfer conduit may be spaced apart from the outlet of the matrix introduction conduit and/or the inlet of said ion analyser and/or the sampling tube; and not connected to these elements by an enclosed conduit.

A longitudinal axis of the sample transfer conduit may be substantially orthogonal to a longitudinal axis through the outlet of the matrix introduction conduit and/or a longitudinal axis through the inlet of said ion analyser and/or a longitudinal axis of the sampling tube.

The matrix may be introduced to the analyte at a distance y upstream of the inlet of said ion analyser, or a distance y upstream of a vacuum chamber in which the collision surface is arranged, wherein y is selected from the group consisting of: (i) 1.5-2.0 mm; (ii) about 2.0-2.5 mm; (iii) about 2.5-3.0 mm; (iv) about 3.0-3.5 mm; (v) about 3.5-4.0 mm; (vi) about 4.0-4.5 mm; (vii) about 4.5-5.0 mm; (viii) about 5.0-5.5 mm; (ix) about 5.5-6.0 mm; (x) about ≥6 mm; (xi) about ≥7 mm; (xii) about ≥8 mm; (xiii) about ≥9 mm; (xiv) about ≥10 mm; (xv) about ≥12 mm; (xvi) about ≥14 mm; (xvii) about ≥16 mm; (xviii) about ≥18 mm; (xix) about ≥20 mm; (xx) about ≥25 mm; (xxi) about ≥30 mm.

The analyte may be supplied through a sample transfer conduit and the matrix may be supplied directly into the sample transfer conduit; or the matrix may be supplied through a matrix introduction conduit and the analyte may be supplied directly into the matrix introduction conduit.

The sample transfer conduit and/or matrix introduction conduit may be directly connected to the inlet of an ion analyser or vacuum chamber in which the collision surface is arranged.

Alternatively, the analyte may be supplied through a sample transfer conduit and the matrix is supplied to the analyte downstream of an exit of the sample transfer tube.

For example, a sample transfer conduit may be provided that performs the step of providing the analyte and the outlet of the matrix introduction conduit may be provided at a location about the circumference of sample transfer conduit. A gas flow may be arranged so as to sweep the matrix from the outlet, into the analyte, and to the inlet of an ion analyser that analyses the ions.

The matrix may be supplied through a matrix introduction conduit having an inner diameter selected from the group consisting of: (i) about ≤900 µm; (ii) about ≤800 µm; (iii) about ≤700 µm; (iv) about ≤600 µm; and (v) about ≤500 µm.

Alternatively, the matrix may be supplied through a matrix introduction conduit having an inner diameter selected from the group consisting of: (i) about ≤450 µm; (ii) about ≤400 µm; (iii) about ≤350 µm; (iv) about ≤300 µm; (v) about ≤250 µm; (vi) about ≤200 µm; (vii) about ≤150 µm; (viii) about ≤100 µm; (ix) about ≤50 µm; and (x) about ≤25 µm.

Matrix introduction conduits having smaller internal diameters tend to produce better and less noisy the spectra. However, it is contemplated that the matrix introduction conduit having an inner diameter ≥450 µm, ≥500 µm, or ≥1 mm.

The matrix may be supplied through a matrix introduction conduit and the exit end of the matrix introduction conduit may be tapered so as to narrow in a downstream direction.

The matrix may be supplied to said analyte by a matrix introduction conduit and at a flow rate selected from the group consisting of: 5-50 µl/min; (i) about 50-100 µl/min; (ii) about 100-150 µl/min; (iii) about 150-200 µl/min; (iv) about 200-250 µl/min; (v) about 250-300 µl/min; (vi) about 300-350 µl/min; (vii) about 350-400 µl/min; (viii) about 400-450 µl/min; (ix) about 450-500 µl/min; (x) about 500-550 µl/min; (xi) about 550-600 µl/min; (xii) about 600-650 µl/min; (xiii) about 650-700 µl/min; (xiv) about 700-750 µl/min; (xv) about 750-800 µl/min; (xvi) about 800-850 µl/min; (xvii) about 850-900 µl/min; (xviii) about 900-950 µl/min; (xix) about 950-1000 µl/min; (xx) about 50 µl/min to 1 ml/min; (xxi) about 100-800 µl/min; (xxii) about 150-600 µl/min; and (xxiii) about 200-400 µl/min.

Relatively low matrix flow rates may be used such that the matrix is non-toxic and/or does not contaminate the instrument.

The method may generate analyte ions and comprise analysing said analyte ions.

The step of analysing said analyte ions may comprise: (i) mass analysing said analyte ions; (ii) analysing the ion mobility or differential ion mobility of said analyte ions; (iii) analysing the ionic cross-sections or collision cross sections of said analyte ions; (iv) separating said analyte ions according to their ion mobility or differential ion mobility; (v) separating said analyte ions according to their ion mobility or differential ion mobility prior to mass analysing said analyte ions; or (vi) excluding or discarding analyte ions based upon their ion mobility or differential ion mobility.

The method may comprise analysing the analyte ions with an ion analyser to obtain analyte ion data, analysing lockmass, lock mobility or calibration ions, and calibrating said ion analyser or adjusting the analyte ion data based upon the data obtained from analysing said lockmass, lock mobility or calibration ions.

A lockmass, lock mobility or calibration compound may be in the matrix for generating the lockmass, lock mobility or calibration ions.

The lockmass, lock mobility or calibration compound/ions may be introduced into the matrix introduction conduit, the analyte introduction conduit or may be supplied in a separate conduit.

The method may comprise using a first device to provide said analyte; wherein said first device may comprise or forms part of an ambient ion or ionisation source; or wherein said first device may generate said aerosol, smoke or vapour from a target to be analysed and which contains ions and/or is subsequently ionised by an ambient ion or ionisation source or other ionisation source.

The target may comprise native or unmodified target material.

The native or unmodified target may be unmodified (i.e. not modified) by the addition of a matrix or reagent.

The first device may be arranged and adapted to generate aerosol, smoke or vapour from one or more regions of said target without said target requiring prior preparation.

The first device may comprise or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

The step of using said first device to generate aerosol, smoke or vapour from one or more regions of said target further may comprise contacting said target with one or more electrodes.

The one or more electrodes may comprise either: (i) a monopolar device, wherein said method optionally further comprises providing a separate return electrode; (ii) a bipolar device; or (iii) a multi-phase RF device, wherein said method optionally further comprises providing a separate return electrode or electrodes.

The one or more electrodes may comprise or form part of a rapid evaporation ionization mass spectrometry ("REIMS") device.

The method may comprise applying an AC or RF voltage to said one or more electrodes in order to generate said aerosol, smoke or vapour.

The step of applying said AC or RF voltage to said one or more electrodes may comprises applying one or more pulses of said AC or RF voltage to said one or more electrodes.

The step of applying said AC or RF voltage to said one or more electrodes may cause heat to be dissipated into said target.

The step of using said first device to generate aerosol, smoke or vapour from one or more regions of said target may comprise irradiating said target with a laser.

The first device may be arranged and adapted to generate aerosol from one or more regions of said target by direct evaporation or vaporisation of target material from said target by Joule heating or diathermy.

The diathermy may be produced by one of three techniques: ultrasound (ultrasonic diathermy); radio frequency diathermy (e.g. shortwave radio frequencies in the range of, for example, 1-100 MHz); or microwave diathermy (e.g., in the 915 MHz or 2.45 GHz bands). The methods of diathermy differ mainly in their penetration capability.

The step of using said first device to generate aerosol, smoke or vapour from one or more regions of said target may comprises directing ultrasonic energy into said target.

The aerosol may comprise uncharged aqueous droplets, optionally comprising cellular material.

At least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", d32) of said aerosol is in a range: (i) <5 μm; (ii) 5-10 μm; (iii) 10-15 μm; (iv) 15-20 μm; (v) 20-25 μm; or (vi) >25 μm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating said aerosol, said aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating said aerosol, said aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating said aerosol, said aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue, such as healthy or diseased tissue.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, soft tissue, connective tissue, peritoneal tissue, blood vessel tissue, fat tissue, ureter tissue, urethra tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

The first device may comprise a point of care ("POC"), diagnostic or surgical device.

The method may comprise ionising at least some of said aerosol, smoke or vapour so as to generate analyte ions.

The method may comprise directing or aspirating at least some of said aerosol, smoke or vapour into a vacuum chamber of a mass and/or ion mobility spectrometer.

The method may comprise ionising at least some said aerosol, smoke or vapour within a or said vacuum chamber of said mass and/or ion mobility spectrometer so as to generate a plurality of analyte ions.

The method may comprise causing said aerosol, smoke or vapour to impact upon the collision surface, optionally located within a vacuum chamber of said mass and/or ion mobility spectrometer, so as to generate the plurality of analyte ions.

The method may comprise mass and/or ion mobility analysing said analyte ions or ions derived from said aerosol, smoke or vapour in order to obtain mass and/or ion mobility spectrometric data.

The method may comprise analysing said spectrometric data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in said target; (vi) to confirm the identity or authenticity of said target; (vii) to determine whether or not one or more impurities, illegal substances or undesired substances are present in said target; (viii) to determine whether a human or animal patient is at an increased risk of suffering an adverse outcome; (ix) to make or assist in the making a diagnosis or prognosis; and (x) to inform a surgeon, nurse, medic or robot of a medical, surgical or diagnostic outcome.

The method may either be part of a surgical method or a non-surgical method. For example, the method may be a surgical method in which the sample may be human or animal tissue containing the analyte. The sample may be subjected to electrosurgical diathermic evaporation, or other forms of rapid evaporation, in order to form the gas phase analyte, vapour analyte or aerosol. By way of example only, the device and method may be used for the identification of human tissues in breast cancer surgery. By analysing the analyte ions it is possible to determine whether or not the tissues are cancerous.

Alternatively, the method may comprise a non-surgical method. For example, human or animal tissue that is not part of the human or animal body (i.e. previously excised, deposited or removed) may be analysed, or samples or biological tissues other than human or animal tissues may be analysed. Again, by analysing the analyte ions it is possible to determine the properties or constituents of the sample, such as whether or not they contain cancerous tissues.

The method may be used in other non-surgical methods, such as country of origin identification, pharmaceutical testing, food safety testing (e.g., dairy), cosmetics testing, military applications, air pollution testing, post-mortem analysis, microbe identification (e.g., bacteria), and automated sampling.

The method may be used to analyse non-biological samples and compounds. The analyte that is formed from the sample may be partially charged and/or may have a relatively high organic content.

The step of analysing the spectrometric data may comprise analysing one or more sample spectra so as to classify an aerosol, smoke or vapour sample.

Analysing the one or more sample spectra so as to classify the aerosol, smoke or vapour sample may comprise unsupervised analysis of the one or more sample spectra (e.g., for dimensionality reduction) and/or supervised analysis of the one or more sample spectra (e.g., for classification).

Analysing the one or more sample spectra may comprise unsupervised analysis (e.g., for dimensionality reduction) followed by supervised analysis (e.g., for classification).

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) (e.g., for classification) after performing principal component analysis (PCA) (e.g., for dimensionality reduction).

Analysing the one or more sample spectra so as to classify the aerosol, smoke or vapour sample may comprise performing a maximum margin criteria (MMC) process (e.g., for classification) after performing principal component analysis (PCA) (e.g., for dimensionality reduction).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may each be defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

The mass and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, and/or dopants may be added to the drift gas to induce a change in drift time of one or more species. This data may then be combined or concatenated.

The first aspect of the present invention also provides apparatus for performing mass and/or ion mobility spectrometry comprising:

an analyte inlet for receiving analyte;
a matrix inlet for receiving a matrix compound;
a mixing region for mixing said analyte with said matrix compound such that, in use, said analyte is diluted by, dissolves in, or forms first clusters with said matrix;
a collision surface; and
a device arranged and adapted to cause said first clusters or first droplets of the diluted or dissolved analyte to collide with said collision surface.

The device may be arranged and adapted to cause the first clusters or first droplets to collide with the collision surface and fragments into a plurality of second smaller clusters or droplets.

The apparatus may be configured to provide the analyte in the form of a gas-phase analyte, aerosol, vapour, smoke or liquid; and/or to supply the matrix to said analyte whilst said analyte is in the form of a gas-phase analyte, aerosol, vapour, smoke or liquid.

The apparatus may be configured to supply the matrix to the analyte whilst the analyte is in the form of an aerosol, vapour or smoke and whilst the matrix is in the form of an aerosol, vapour, or solid particles.

The apparatus may be configured to supply matrix molecules to, and intermix said matrix molecules with, said analyte whilst said matrix is in a gas phase or in the form of an aerosol, vapour or solid particles.

The apparatus may comprise a high pressure region and a low pressure region and may be configured to transfer the mixture of said analyte and said matrix from the high pressure region to the low pressure region such that, in use, said gas phase matrix cools and condenses to a liquid and said analyte dissolves in said liquid matrix so as to form said first droplets.

Alternatively, the apparatus may be configured to supply the matrix to, and intermixed with, the analyte as a liquid.

If the analyte and/or matrix is in liquid form then the apparatus may be configured to convert the analyte and/or matrix into droplets or vapour, e.g., by spraying or nebulising. For example, if the analyte and matrix are mixed as liquids then the mixture may subsequently be converted into the first analyte droplets, e.g., by spraying or nebulising.

The matrix may initially be supplied as a solid (e.g., a powder) and sublimated or melted and evaporated so as to form matrix in vapour or gas-phase that is intermixed with the analyte to form clusters of analyte and matrix.

The matrix may be selected from the group consisting of: (i) a solvent for said analyte; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; and (xxiii) propanol.

By way of example, for analytes comprising polar lipids, low molecular weight alcohols may be used as the matrix (e.g., methanol, ethanol, isopropanol) or ketones (e.g., acetone). These matrices have been shown to enhance the ionisation of species otherwise detected in the absence of the matrix vapours at lower intensity.

A protic matrix solvent may be used, e.g., for the analysis of lipids or triglycerides. Alternatively, a non-protic or aprotic matrix solvent may be used, e.g., for the analysis of proteins.

The mixture of analyte and matrix may be a homogeneous or heterogeneous mixture.

The matrix and/or analyte may be doped with one or more additives for enhancing the solvation of the analyte in the matrix or for enhancing the ionisation of the analyte.

The matrix or analyte is doped with an acidic or basic additive. For example, the matrix may be doped with formic acid, diethylamine.

The matrix may cause derivatisation of the analyte. For example, the matrix may cause the derivatisation of cholesterol or steroids in the analyte. This may render the analyte more easily ionised.

A calibrant may be added to the matrix and/or analyte, or a compound in the matrix and/or analyte may be selected as a calibrant, and used to calibrate the method of mass spectrometry and/or ion mobility spectrometry. This is particularly useful in ambient ionisation techniques such as REIMS techniques, in which it may be difficult to introduce calibrants according to conventional techniques.

The apparatus may be configured to accelerate said first clusters or first droplets onto said collision surface.

The apparatus may be configured to accelerate said first clusters or first droplets onto said collision surface using a pressure differential.

The apparatus may be configured to create a pressure differential between a first region and a second region for accelerating the first clusters or first droplets between the two regions and onto the collision surface.

The apparatus may comprise a mass and/or ion mobility spectrometer having an atmospheric interface arranged between the first and second regions, wherein the second region may comprise a vacuum chamber that is connected to the vacuum pump and which houses the collision surface.

The apparatus may be configured to evaporate the matrix from the analyte in the second droplets so as to provide analyte ions that are separate from said matrix.

The step of colliding the first clusters or first droplets with the collision surface may evaporate the matrix from the analyte by converting kinetic energy of the analyte and matrix into heat.

The step of colliding the first clusters or first droplets causes the second smaller clusters or droplets to be generated, at least some of which may have only a single analyte molecule therein. This enhances the ionisation process.

The step of evaporating said matrix from said analyte may result in charge transfer to or from said analyte so as to ionise said analyte to form analyte ions.

The apparatus may comprise ion trap for trapping analyte ions and/or an ion guide for guiding analyte ions.

The apparatus may comprise a heater for heating said collision surface.

The heater may be configured to heat said collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The apparatus may comprise a matrix introduction conduit for supplying said matrix to said analyte, and an ion analyser arranged downstream of an outlet of said matrix introduction conduit for analysing ions of the analyte.

The distance x between said outlet of said matrix introduction conduit and an inlet of said ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm;

(vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about ≤6 mm; (xiv) about ≤5.5 mm; (xv) about ≤5 mm; (xvi) about ≤4.5 mm; (xvii) about ≤4 mm; (xviii) about ≤3.5 mm; and (xix) about ≤3 mm.

The ion analyser may comprise a vacuum chamber into which the inlet opens. The inlet of the ion analyser may be determined to be a region that is at the pressure of the vacuum chamber. For example, if the inlet is provided by an elongated tube then the distance x may be determined from the position in the tube that is at the pressure of the vacuum chamber. Alternatively, or additionally, the inlet may be determined to be the entrance and/or exit of an inlet tube or orifice.

The matrix introduction conduit may have an exit opening substantially facing or opposite the inlet of said ion analyser; and/or wherein the exit opening of the matrix introduction conduit is substantially coaxial with the inlet of said ion analyser.

The outlet of the matrix introduction conduit and the inlet of said ion analyser may be spaced apart and not connected by a completely enclosed conduit.

The exit of the matrix introduction conduit and the inlet of the ion analyser may be interconnected by a sampling tube having an opening in its circumference for receiving the analyte through the opening.

The apparatus may comprise a sample transfer conduit for delivering the analyte, wherein the sample transfer conduit may be arranged such that, in use, the analyte impacts on an upstream side of the sampling tube, flows around the outside of the sampling tube and into said opening in a downstream side of the sampling tube.

The outlet of the sample transfer conduit may be spaced apart from the outlet of the matrix introduction conduit and/or the inlet of said ion analyser and/or the sampling tube; and not connected to these elements by an enclosed conduit.

A longitudinal axis of the sample transfer conduit may be substantially orthogonal to a longitudinal axis through the outlet of the matrix introduction conduit and/or a longitudinal axis through the inlet of said ion analyser and/or a longitudinal axis of the sampling tube.

The matrix may be introduced to the analyte at a distance y upstream of the inlet of said ion analyser, or a distance y upstream of a vacuum chamber in which the collision surface is arranged, wherein y is selected from the group consisting of: (i) 1.5-2.0 mm; (ii) about 2.0-2.5 mm; (iii) about 2.5-3.0 mm; (iv) about 3.0-3.5 mm; (v) about 3.5-4.0 mm; (vi) about 4.0-4.5 mm; (vii) about 4.5-5.0 mm; (viii) about 5.0-5.5 mm; (ix) about 5.5-6.0 mm; (x) about ≥6 mm; (xi) about ≥7 mm; (xii) about ≥8 mm; (xiii) about ≥9 mm; (xiv) about≥10 mm; (xv) about ≥12 mm; (xvi) about ≥14 mm; (xvii) about ≥16 mm; (xviii) about ≥18 mm; (xix) about ≥20 mm; (xx) about ≥25 mm; (xxi) about ≥30 mm.

The apparatus may comprise a sample transfer conduit for supplying the analyte and matrix introduction conduit for supplying the matrix directly into the sample transfer conduit; or may comprise a matrix introduction conduit for supplying the matrix and a sample transfer conduit for supplying the analyte directly into the matrix introduction conduit.

The sample transfer conduit and/or matrix introduction conduit may be directly connected to the inlet of an ion analyser or vacuum chamber in which the collision surface is arranged.

Alternatively, the analyte may be supplied through a sample transfer conduit and the matrix is supplied to the analyte downstream of an exit of the sample transfer tube. For example, a sample transfer conduit may be provided that performs the step of providing the analyte and the outlet of the matrix introduction conduit may be provided at a location about the circumference of sample transfer conduit. A gas flow may be arranged so as to sweep the matrix from the outlet, into the analyte, and to the inlet of an ion analyser that analyses the ions.

The apparatus may comprise a matrix introduction conduit for supplying the matrix, wherein the matrix introduction conduit has an inner diameter selected from the group consisting of: (i) about ≤450 µm; (ii) about ≤400 µm; (iii) about ≤350 µm; (iv) about ≤300 µm; (v) about ≤250 µm; (vi) about ≤200 µm; (vii) about ≤150 µm; (viii) about ≤100 µm; (ix) about ≤50 µm; and (x) about ≤25 µm.

Matrix introduction conduits having smaller internal diameters tend to produce better and less noisy the spectra.

The apparatus may comprise a matrix introduction conduit for supplying the matrix, wherein the exit end of the matrix introduction conduit is tapered so as to narrow in a downstream direction.

The apparatus may comprise a pump configured to supply said matrix to the analyte through a matrix introduction conduit at a flow rate selected from the group consisting of: 5-50 µl/min; (i) about 50-100 µl/min; (ii) about 100-150 µl/min; (iii) about 150-200 µl/min; (iv) about 200-250 µl/min; (v) about 250-300 µl/min; (vi) about 300-350 µl/min; (vii) about 350-400 µl/min; (viii) about 400-450 µl/min; (ix) about 450-500 µl/min; (x) about 500-550 µl/min; (xi) about 550-600 µl/min; (xii) about 600-650 µl/min; (xiii) about 650-700 µl/min; (xiv) about 700-750 µl/min; (xv) about 750-800 µl/min; (xvi) about 800-850 µl/min; (xvii) about 850-900 µl/min; (xviii) about 900-950 µl/min; (xix) about 950-1000 µl/min; (xx) about 50 µl/min to 1 ml/min; (xxi) about 100-800 µl/min; (xxii) about 150-600 µl/min; and (xxiii) about 200-400 µl/min.

Relatively low matrix flow rates may be used such that the matrix is non-toxic and/or does not contaminate the instrument.

The apparatus may comprise a mass and/or ion mobility analyser for analysing analyte ions.

The apparatus may comprise a first device for providing said analyte; wherein said first device comprises or forms part of an ambient ion or ionisation source; or wherein said first device is configured to generate a or said aerosol, smoke or vapour from a target to be analysed and which contains ions and/or is subsequently ionised by an ambient ion or ionisation source or other ionisation source.

The target may comprise native or unmodified target material.

The native or unmodified target material is unmodified by the addition of a matrix or reagent.

The first device or apparatus is arranged and adapted to generate aerosol, smoke or vapour from one or more regions of said target without said target requiring prior preparation.

The first device or apparatus may comprise or form part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

The first device or apparatus may comprise one or more electrodes and may be arranged and adapted to generate aerosol, smoke or vapour from one or more regions of said target by contacting said target with said one or more electrodes.

The one or more electrodes may comprise either: (i) a monopolar device, wherein optionally a separate return electrode is provided; (ii) a bipolar device; or (iii) a multi-phase RF device, wherein optionally at least one separate return electrode is provided.

The one or more electrodes may comprise a rapid evaporation ionization mass spectrometry ("REIMS") device.

The apparatus may comprise a device arranged and adapted to apply an AC or RF voltage to said one or more electrodes in order to generate said aerosol, smoke or vapour.

The device for applying said AC or RF voltage to said one or more electrodes may be arranged to apply one or more pulses of said AC or RF voltage to said one or more electrodes.

The application of said AC or RF voltage to said one or more electrodes may cause heat to be dissipated into said target.

The first device or apparatus may comprise a laser for irradiating said target.

The first device or apparatus may be arranged and adapted to generate aerosol from one or more regions of said target by direct evaporation or vaporisation of target material from said target by Joule heating or diathermy.

The first device or apparatus may be arranged and adapted to direct ultrasonic energy into said target.

The aerosol may comprise uncharged aqueous droplets, optionally comprising cellular material.

At least 50%, 55%, 60%, 65%, 70%, 75%, 80%, 85%, 90% or 95% of the mass or matter generated by said first device or apparatus and which forms said aerosol may be in the form of droplets.

The first device may be arranged and adapted to generate aerosol wherein the Sauter mean diameter ("SMD", d32) of said aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating said aerosol, said aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xi) >1000.

Substantially at the point of generating said aerosol, said aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating said aerosol, said aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise biological tissue.

The biological tissue may comprise human tissue or non-human animal tissue.

The biological tissue may comprise in vivo biological tissue.

The biological tissue may comprise ex vivo biological tissue.

The biological tissue may comprise in vitro biological tissue.

The biological tissue may comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, soft tissue, connective tissue, peritoneal tissue, blood vessel tissue, fat tissue, ureter tissue, urethra tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

The first device or apparatus may comprise a point of care ("POC"), diagnostic or surgical device.

The collision surface may be substantially spherical, coil-shaped, helical, spiral-shaped, cylindrical, tubular, rod-shaped, hemispherical, teardrop-shaped, plate-shaped, concave, dish-shaped or conical; or wherein the collision surface is the inner surface of a hollow collision assembly.

The present invention provides a mass and/or ion mobility spectrometer comprising apparatus as described herein.

The spectrometer may comprise a spectrometer main housing or assembly and the source housing may be connected, in use, to said spectrometer main housing.

The spectrometer may comprise an ion trap and/or an ion guide; optionally wherein the ion guide is configured to apply an electric field that separates ions from neutral species.

The spectrometer may comprise an analyser for analysing analyte ions.

The analyser may comprise: (i) a mass analyser for mass analysing said analyte ions; (ii) an ion mobility or differential ion mobility analyser; (iii) an analyser for analysing the ionic cross-sections or collision cross sections of said analyte ions; (iv) a separator for separating said analyte ions according to their ion mobility or differential ion mobility; (v) a separator for separating said analyte ions according to their ion mobility or differential ion mobility prior to mass analysing said analyte ions; or (vi) a device arranged and adapted to exclude or discard analyte ions based upon their ion mobility or differential ion mobility.

The apparatus and spectrometer may be arranged and configured to perform any one of the methods described herein.

The present invention also provides a method of surgery or electrosurgery comprising any of the method steps described herein, wherein the method comprises:

contacting biological tissue with a surgical or electrosurgical tool and activating said tool so as to generate smoke, fumes, liquid, gas, surgical smoke, aerosol or vapour containing said analyte;

aspirating said smoke, fumes, liquid, gas, surgical smoke, aerosol or vapour;

mixing said matrix with said aspirated smoke, fumes, liquid, gas, surgical smoke, aerosol or vapour;

causing said aspirated smoke, fumes, liquid, gas, surgical smoke, aerosol or vapour in combination with said matrix to impact upon said collision surface located within a vacuum chamber of a mass and/or ion mobility spectrometer in order to form analyte ions; and mass and/or ion mobility analysing said analyte ions.

The present invention also provides a surgical or electrosurgical apparatus comprising:

a surgical or electrosurgical tool comprising one or more electrodes;

a device arranged and adapted to activate said tool when said tool is in contact, in use, with biological tissue so as to generate analyte, smoke, fumes, liquid, gas, surgical smoke, aerosol or vapour;

a device arranged and adapted to aspirate said analyte, smoke, fumes, liquid, gas, surgical smoke, aerosol or vapour;

a device arranged and adapted to mix a matrix with said aspirated analyte, smoke, fumes, liquid, gas, surgical smoke, aerosol or vapour; and a mass and/or ion mobility spectrometer comprising: (i) a collision surface located within a vacuum chamber of said spectrometer wherein, in use, analyte, smoke, fumes, liquid, gas, surgical smoke, aerosol or vapour is arranged to impact upon said collision surface so as to form analyte ions; and (ii) a mass and/or ion mobility analyser for mass and/or ion mobility analysing said analyte ions.

The surgical or electrosurgical apparatus may be configured to perform any of the method described herein.

Although the mixture of the matrix and analyte have been described above as impacting on the collision surface, it has been found that there may be improvements in ionisation of the analyte without impacting the mixture on the collision surface. For example, techniques other than colliding the mixture with a collision surface may be used to atomise the mixture. Accordingly, the step of colliding the first clusters or first droplets of the diluted or dissolved matrix with the collision surface is not an essential feature of the invention.

Therefore, from a second aspect the present invention also provides a method mass and/or ion mobility spectrometry comprising:

providing an analyte;

supplying a matrix compound to said analyte such that said analyte is diluted by, dissolved in, or forms first clusters with said matrix; and fragmenting or disintegrating said first clusters or first droplets of said diluted or dissolved matrix into a plurality of second smaller clusters or droplets.

The first clusters or first droplets may be fragmented or disintegrated by applying laser irradiation, by applying ultrasonic energy, by a glow discharge technique or by photoionization.

The method of the second aspect may comprise any of the features described in relation to the first aspect of the invention, except wherein the mixture is not collided on the collision surface.

For example, the method may comprise subjecting analyte in, or derived from, said second smaller clusters or droplets to ionisation. Optionally, said ionisation is performed by an ionisation source selected from the group consisting of: a corona discharge ionisation source; a reagent ion Ionisation source; a Photo Ionisation source; a Chemical Ionisation source; an Electron Impact ("EI") ionisation source; a Field Ionisation ("FI") source; a Field Desorption ("FD") Ionisation source; an Inductively Coupled Plasma ("ICP") Ionisation source; a Fast Atom Bombardment ("FAB") Ionisation source; a Liquid Secondary Ion Mass Spectrometry ("LSIMS") Ionisation source; a Desorption Electrospray Ionisation ("DESI") Ionisation source; a Nickel-63 radioactive Ionisation source; a Thermospray Ionisation source; an Atmospheric Sampling Glow Discharge Ionisation ("ASGDI") Ionisation source; a Glow Discharge ("GD") Ionisation source; an Impactor Ionisation source; a Direct Analysis in Real Time ("DART") Ionisation source; a Laserspray Ionisation ("LSI") source; a Sonicspray Ionisation ("SSI") source; a Matrix Assisted Inlet Ionisation ("MAII") source; a Solvent Assisted Inlet Ionisation ("SAII") source; a Desorption Electrospray Ionisation ("DESI") source; a desorption electroflow focusing ionisation ("DEFFI") source; a Laser Ablation Electrospray Ionisation ("LAESI") source; and a Surface Assisted Laser Desorption Ionisation ("SALDI") source.

The second aspect of the invention also provides, an apparatus for performing mass and/or ion mobility spectrometry comprising:

a mixing region for mixing analyte with a matrix compound such that, in use, said analyte is diluted by, dissolved in, or forms first clusters with said matrix; and a device arranged and adapted to fragment or disintegrate said first clusters or first droplets of said diluted or dissolved matrix into a plurality of second smaller clusters or droplets.

The apparatus may comprise an analyte inlet for receiving analyte and/or a matrix inlet for receiving a matrix compound.

The apparatus according to the second aspect may comprise any of the features described in relation to the first aspect, except wherein the apparatus need not comprise the collision surface or the device arranged and adapted to cause said first clusters or first droplets of the diluted or dissolved analyte to collide with the collision surface.

The invention also provides a mass and/or ion mobility spectrometer comprising such an apparatus.

The invention also provides a method of surgery or electrosurgery comprising the method of the second aspect, wherein the method comprises:

contacting biological tissue with a surgical or electrosurgical tool and activating said tool so as to generate smoke, fumes, liquid, gas, surgical smoke, aerosol or vapour containing said analyte;

aspirating said smoke, fumes, liquid, gas, surgical smoke, aerosol or vapour;

mixing said matrix with said aspirated smoke, fumes, liquid, gas, surgical smoke, aerosol or vapour;

fragmenting or disintegrating first clusters or droplets of the mixture to form a plurality of second smaller clusters or droplets;

forming analyte ions from the second clusters or droplets; and mass and/or ion mobility analysing said analyte ions.

The invention also provides a surgical or electrosurgical apparatus comprising the apparatus of the second aspect, wherein the surgical or electrosurgical apparatus comprises:

a surgical or electrosurgical tool comprising one or more electrodes;

a device arranged and adapted to activate said tool when said tool is in contact, in use, with biological tissue so as to generate smoke, fumes, liquid, gas, surgical smoke, aerosol or vapour containing the analyte;

a device arranged and adapted to aspirate said analyte, smoke, fumes, liquid, gas, surgical smoke, aerosol or vapour;

a device arranged and adapted to mix a matrix with said aspirated analyte, smoke, fumes, liquid, gas, surgical smoke, aerosol or vapour; and a device arranged and adapted to fragment or disintegrate first clusters or droplets of the mixture to form a plurality of second smaller clusters or droplets;

a device arranged and adapted to ionise the analyte to form analyte ions from the second clusters or droplets; and a mass and/or ion mobility analyser for analysing said analyte ions.

According to an aspect there is provided a method of Rapid Evaporative Ionisation Mass Spectrometry ("REIMS"). The method includes providing an analyte; supplying a matrix compound to the analyte such that the analyte dissolves in the matrix and forms first dissolved analyte droplets; and colliding the first dissolved analyte droplets with a collision surface or a gas such that the first dissolved analyte droplets fragment into a plurality of second smaller dissolved analyte droplets.

The collisional ion generator REIMS technique described in the background section involves generating a sample of aerosol droplets that are comprised of aqueous droplets covered with polar lipids. The aqueous droplets are accelerated by the free jet expansion in the atmospheric inlet of a mass spectrometer such that the high velocity droplets impact onto a collision surface or other gaseous particles, producing gaseous ions of the polar lipid molecules. However, the ionisation yield of this technique is relatively low.

It has been recognised that the ion yield in the conventional method is relatively low due to the poor conversion rate of the droplets into individual molecular species mostly caused by the strong intermolecular bonds between the analyte molecules.

An embodiment involves dissolving the analyte in a matrix thereby substantially eliminating the intermolecular bonding between the analyte molecules. As such, when the dissolved analyte is subsequently collided with the collision surface or a gas so as to fragment into droplets, any given droplet is likely to contain fewer analyte molecules than it would if the matrix were not present.

The approach according to an embodiment therefore leads to the more efficient generation of ions when the matrix in each droplet is evaporated.

The step of colliding the first dissolved analyte droplets with the collision surface or gas causes the step of evaporating the matrix from the analyte by converting kinetic energy of the analyte and matrix into heat.

The step of colliding the first dissolved analyte droplets may cause the smaller dissolved analyte droplets to be generated, at least some of which may have only a single analyte molecule therein. This enhances the ionisation process.

The analyte may, for example, comprise a polar lipid and the vapour or aerosol may comprise aqueous droplets covered with the polar lipids.

The analyte may comprise triglycerides.

The analyte to which the matrix is supplied may comprise ionised analyte molecules.

The method may further comprise the step of generating the gas phase analyte, vapour analyte, aerosol, or liquid from a sample to be analysed.

The gas phase analyte, vapour analyte or aerosol may be generated by heating the sample containing the analyte, may by diathermic evaporation of the sample.

The method may either be part of a surgical method or a non-surgical method. For example, the method may be a surgical method in which the sample may be human or animal tissue containing the analyte. The sample may be subjected to electrosurgical diathermic evaporation, or other forms of rapid evaporation, in order to form the gas phase analyte, vapour analyte or aerosol. By way of example only, the device and method may be used for the identification of human tissues in breast cancer surgery. By analysing the analyte ions it is possible to determine whether or not the tissues are cancerous.

Alternatively, the method may comprise a non-surgical method. For example, human or animal tissue that is not part of the human or animal body (i.e. previously excised, deposited or removed) may be analysed, or samples or biological tissues other than human or animal tissues may be analysed. Again, by analysing the analyte ions it is possible to determine the properties or constituents of the sample, such as whether or not they contain cancerous tissues.

The embodiment may be used in other non-surgical methods, such as country of origin identification, pharmaceutical testing, food safety testing (e.g. dairy), cosmetics testing, military applications, air pollution testing, post-mortem analysis, microbe identification (e.g. bacteria), and automated sampling.

The method may be used to analyse non-biological samples and compounds.

The analyte that is formed from the sample may be partially charged and/or may have a relatively high organic content.

The method may further comprise evaporating the matrix from the analyte in the second smaller dissolved analyte droplets so as to provide analyte ions that are substantially separate from the matrix.

The step of evaporating the matrix from the analyte may result in separation of the ionically dissociated analyte ions from the matrix so as to form gas phase analyte ions.

After the step of evaporating the matrix from the analyte, the method may further comprise trapping analyte ions in an ion trap and/or guiding analyte ions using an ion guide.

The method may further comprise analysing the analyte ions.

The step of analysing the analyte ions may further comprises: (i) mass analysing the analyte ions; (ii) analysing the ion mobility or differential ion mobility of the analyte ions; (iii) analysing the ionic cross-sections or collision cross sections of the analyte ions; (iv) separating the analyte ions according to their ion mobility or differential ion mobility; (v) separating the analyte ions according to their ion mobility or differential ion mobility prior to mass analysing the analyte ions; or (vi) excluding or discarding analyte ions based upon their ion mobility or differential ion mobility.

The matrix may be supplied to the analyte whilst the analyte is in gas phase, vapour form, aerosol form or in liquid phase.

The step of supplying a matrix compound to the analyte may comprise supplying matrix molecules to, and intermixing the matrix molecules with, the analyte whilst the matrix is in a gas phase.

The mixture of the analyte and the matrix may be transferred from a high pressure region to a low pressure region such that the gas phase matrix cools and condenses to a liquid and the analyte dissolves in the liquid matrix so as to form the first dissolved analyte droplets.

The matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The step of colliding the first dissolved analyte droplets with the collision surface or the gas further may comprise accelerating the first dissolved analyte droplets onto the collision surface or into the gas.

The step of accelerating the first dissolved analyte droplets into the collision surface or the gas may comprise using a pressure differential to accelerate the first dissolved analyte droplets onto the collision surface or into the gas.

The method may further comprise analysing the analyte ions using a mass spectrometer comprising an atmospheric interface adjacent a vacuum chamber, wherein the first dissolved analyte droplets are accelerated into the collision surface or gas by a pressure difference across the atmospheric interface.

The method may further comprise heating the collision surface (or alternatively a collision gas).

The method may further comprise heating the collision surface (or alternatively a collision gas) to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The matrix may be supplied to the analyte by a matrix introduction conduit.

The method may further comprise analysing analyte ions using an ion analyser arranged downstream of an outlet of the matrix introduction conduit.

The distance x between the outlet of the matrix introduction conduit and an inlet of the ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) 0.5-5.0 mm.

The matrix may be supplied to the analyte by a matrix introduction conduit at a flow rate selected from the group consisting of: (i) about 50-100 µl/min; (ii) about 100-150 µl/min; (iii) about 150-200 µl/min; (iv) about 200-250 µl/min; (v) about 250-300 µl/min; (vi) about 300-350 µl/min; (vii) about 350-400 µl/min; (viii) about 400-450 µl/min; (ix) about 450-500 µl/min; (x) about 500-550 µl/min; (xi) about 550-600 µl/min; (xii) about 600-650 µl/min; (xiii) about 650-700 µl/min; (xiv) about 700-750 µl/min; (xv) about 750-800 µl/min; (xvi) about 800-850 µl/min; (xvii) about 850-900 µl/min; (xviii) about 900-950 µl/min; (xix) about 950-1000 µl/min; (xx) about 50 µl/min to 1 ml/min; (xxi) about 100-800 µl/min; (xxii) about 150-600 µl/min; and (xxiii) about 200-400 µl/min.

An outlet of the matrix introduction conduit may be opposite or coaxial with an inlet of an ion analyser.

The method may further comprise mass and/or ion mobility analysing analyte ions with an ion analyser to obtain analyte ion data, and wherein the method further comprises analysing lockmass, lock mobility or calibration ions, and may calibrating the ion analyser or adjusting analyte ion data based upon the data obtained from analysing the lockmass, lock mobility or calibration ions.

According to another aspect there is provided a method of mass and/or ion mobility spectrometry, comprising a method as described above.

According to another aspect there is provided apparatus for performing rapid evaporative ionisation mass spectrometry ("REIMS") comprising:

an analyte inlet for receiving analyte;

a mixing region for mixing the analyte with a matrix compound such that the analyte dissolves, in use, in the matrix and forms first dissolved analyte droplets;

a collision surface or a gas; and a device arranged and adapted to cause the first dissolved analyte droplets to collide with the collision surface or the gas such that the first dissolved analyte droplets fragment into a plurality of second smaller dissolved analyte droplets.

The apparatus may further comprise a device arranged and adapted to evaporate the matrix from the analyte in the second smaller dissolved analyte droplets so as to provide analyte ions that are separate from the matrix.

The apparatus may further comprise a device arranged and adapted to evaporate the matrix from the analyte so as to cause charge transfer to or from the analyte so as to ionise the analyte to form analyte ions.

The apparatus may further comprise an ion trap and/or an ion guide.

The apparatus may further comprise a device which is arranged and adapted after the matrix has been evaporated, in use, from the analyte, to trap analyte ions in the ion trap and/or to guide analyte ions using the ion guide.

The apparatus may further comprise an analyser for analysing the analyte ions.

The analyser may comprise: (i) a mass analyser for mass analysing the analyte ions; (ii) an ion mobility or differential ion mobility analyser; (iii) an analyser for analysing the ionic cross-sections or collision cross sections of the analyte ions; (iv) a separator for separating the analyte ions according to their ion mobility or differential ion mobility; (v) a separator for separating the analyte ions according to their ion mobility or differential ion mobility prior to mass analysing the analyte ions; or (vi) a device arranged and adapted to exclude or discard analyte ions based upon their ion mobility or differential ion mobility.

The matrix may be supplied, in use, to the analyte whilst the analyte is in gas phase, vapour form, aerosol form or in liquid phase.

The apparatus may further comprise a device arranged and adapted to supply matrix molecules to, and to intermix the matrix molecules with, the analyte whilst the matrix is in a gas phase.

The apparatus may further comprise a device which is arranged and adapted to transfer the mixture of the analyte and the matrix from a high pressure region to a low pressure region such that the gas phase matrix cools and condenses to a liquid and the analyte dissolves in the liquid matrix so as to form the first dissolved analyte droplets.

The matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

According to another aspect there is provided a mass and/or ion mobility spectrometer comprising apparatus as described above.

The spectrometer may further comprise a device which is arranged and adapted to accelerate the first dissolved analyte droplets into the collision surface or the gas.

The spectrometer may further comprise a device arranged and adapted to maintain a pressure differential to accelerate the first dissolved analyte droplets into the collision surface or the gas.

The spectrometer may further comprise an analyser which is arranged to analyse the analyte ions, wherein the spectrometer further comprises an atmospheric interface adjacent a vacuum chamber, wherein the first dissolved analyte droplets are accelerated into the collision surface or the gas by a pressure difference across the atmospheric interface.

The spectrometer may further comprise a heater for heating the collision surface (or alternatively a collision gas).

The heater may be arranged to heat the collision surface (or alternatively a collision gas) to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The spectrometer may further comprise a matrix introduction conduit for supplying the matrix to the analyte.

The spectrometer may further comprise an ion analyser for analysing the analyte ions, wherein the ion analyser is arranged downstream of an outlet of the matrix introduction conduit.

The distance x between the outlet of the matrix introduction conduit and an inlet of the ion analyser may be selected from the group consisting of: (i) about 0.1 to 0.5 mm; (ii) about 0.5-1.0 mm; (iii) about 1.0-1.5 mm; (iv) about 1.5-2.0 mm; (v) about 2.0-2.5 mm; (vi) about 2.5-3.0 mm; (vii) about 3.0-3.5 mm; (viii) about 3.5-4.0 mm; (ix) about 4.0-4.5 mm; (x) about 4.5-5.0 mm; (xi) about 5.0-5.5 mm; (xii) about 5.5-6.0 mm; (xiii) about 6.0-6.5 mm; (xiv) about 6.5-7.0 mm; (xv) about 7.0-7.5 mm; (xvi) about 7.5-8.0 mm; (xvii) about 8.0-8.5 mm; (xviii) about 8.5-9.0 mm; (xix) about 9.0-9.5 mm; (xx) about 9.5-10.0 mm; (xxi) about 0.1-10 mm; (xxii) about 0.1-7.5 mm; (xxiii) about 0.1-5.1 mm; (xxiv) about 0.5-5.1 mm; and (xxv) about 0.5-5.0 mm.

The spectrometer may further comprise a pump for supplying the matrix to the analyte via a matrix introduction conduit at a flow rate selected from the group consisting of: (i) about 50-100 µl/min; (ii) about 100-150 µl/min; (iii) about 150-200 µl/min; (iv) about 200-250 µl/min; (v) about 250-300 µl/min; (vi) about 300-350 µl/min; (vii) about 350-400 µl/min; (viii) about 400-450 µl/min; (ix) about 450-500 µl/min; (x) about 500-550 µl/min; (xi) about 550-600 µl/min; (xii) about 600-650 µl/min; (xiii) about 650-700 µl/min; (xiv) about 700-750 µl/min; (xv) about 750-800 µl/min; (xvi) about 800-850 µl/min; (xvii) about 850-900 µl/min; (xviii) about 900-950 µl/min; (xix) about 950-1000 µl/min; (xx) about 50 µl/min to 1 µl/min; (xxi) about 100-800 µl/min; (xxii) about 150-600 µl/min; and (xxiii) about 200-400 µl/min.

An outlet of the matrix introduction conduit may be opposite or coaxial with an inlet of an ion analyser.

The mass spectrometer may further comprise a mass analyser for analysing the analyte ions to obtain analyte ion data, and wherein the mass analyser may be further arranged to analyse lockmass, lock mobility or calibration ions, and to calibrate the ion analyser or adjust analyte ion data based upon the data obtained from analysing the lockmass, lock mobility or calibration ions.

According to another aspect there is provided a method of electrosurgery comprising:

contacting biological tissue with an electrosurgical tool and activating the electrosurgical tool so as to generate analyte, smoke, fumes, liquid, gas, surgical smoke, aerosol or vapour;

aspirating the analyte, smoke, fumes, liquid, gas, surgical smoke, aerosol or vapour;

mixing a matrix with the aspirated analyte, smoke, fumes, liquid, gas, surgical smoke, aerosol or vapour;

causing the aspirated analyte, smoke, fumes, liquid, gas, surgical smoke, aerosol or vapour in combination with the matrix to impact upon a collision surface (or alternatively a collision gas) may located within a vacuum chamber of a mass spectrometer in order to form analyte ions; and mass and/or ion mobility analysing the analyte ions.

According to another aspect there is provided an Electrosurgical apparatus comprising:

a rapid evaporative ionisation mass spectrometry ("REIMS") electrosurgical tool comprising one or more electrodes;

a device arranged and adapted to activate the electrosurgical tool when the electrosurgical tool is in contact, in use, with biological tissue so as to generate analyte, smoke, fumes, liquid, gas, surgical smoke, aerosol or vapour;

a device arranged and adapted to aspirate the analyte, smoke, fumes, liquid, gas, surgical smoke, aerosol or vapour;

a device arranged and adapted to mix a matrix with the aspirated analyte, smoke, fumes, liquid, gas, surgical smoke, aerosol or vapour; and a mass and/or ion mobility spectrometer comprising: (i) a collision surface (or alternatively a collision gas) may located within a vacuum chamber of the mass spectrometer wherein, in use, analyte, smoke, fumes, liquid, gas, surgical smoke, aerosol or vapour is arranged to impact upon the collision surface (or alternatively a collision gas) so as to form analyte ions; and (ii) a mass analyser for mass analysing the analyte ions.

According to an embodiment the matrix may initially be supplied as a solid e.g. powder and sublimated or melted and evaporated so as to form matrix in vapour or gas-phase that is intermixed with the analyte.

Alternatively, the matrix may be supplied to, and intermixed with, the analyte as a liquid, aerosol or vapour. If the analyte and/or matrix is in liquid form then the mixture of analyte and matrix may need to be subsequently converted into the first dissolved analyte droplets e.g. by spraying.

The dielectric constant of the matrix may be sufficiently high such that the solvation of the analyte involves ionic dissociation resulting in solvated ions of the analyte present in the condensed phase. In these cases, the impact on the collision surface (or alternatively a collision gas) is more likely to produce solvated ions in the gas phase, which may eventually yield ions formed by deprotonation (in a negative ion mode, i.e. $[M-H]^-$), ions formed by protonation (in a positive ion mode, i.e. $[M+H]^+$), and/or molecular ions.

Isopropanol is a particularly advantageous matrix to use, e.g., for lipid species.

By way of example, for analytes comprising polar lipids, the matrix may be or may comprise, low molecular weight alcohols (e.g. methanol, ethanol, isopropanol) or ketones (e.g. acetone). These matrices have been shown to enhance the ionisation of all or certain species otherwise detected in the absence of the matrix vapours at lower intensity.

The mixture of analyte and matrix may be a homogeneous or heterogeneous mixture.

Voltages may be applied to the ion trap or ion guide so as to trap or guide the ions respectively. The ions may then be delivered from the ion trap or ion guide to an ion analyser for analysing the mass and/or ion mobility of the ions.

The ions may be separated according to ion mobility prior to being mass analysed. Ions may then be excluded or discarded based upon their ion mobility.

Any one of the above mentioned ranges may be combined with any one of the ranges in the list of ranges for distance x.

The inlet of the ion analyser may be an aperture or orifice that separates a vacuum chamber of the ion analyser from a higher pressure region upstream of the ion analyser. For example, the inlet may be an atmospheric pressure interface.

According to an alternative embodiment the matrix introduction conduit may deliver matrix directly into a sample transfer conduit that performs the step of providing the analyte.

Alternatively, a sample transfer conduit may be provided that performs the step of providing the analyte, and the outlet of the matrix introduction conduit may be provided at a location about the circumference of sample transfer conduit. A gas flow may be arranged so as to sweep the matrix from the outlet to the inlet of the ion analyser that analyses the ions.

The device for evaporating the sample may comprise an electrosurgical tool such as a diathermic device.

The device may have an end, point or region for inserting onto a sample to evaporate the sample and wherein the analyte inlet is adjacent the end, point or region.

The apparatus may comprise a source of the matrix compound for supplying the matrix compound to the conduit.

The accelerating means may comprise a vacuum pump for creating a pressure differential between a first region and a second region for accelerating the first dissolved analyte droplets between the two regions and onto the collision surface (or alternatively a collision gas).

The apparatus may comprise a mass spectrometer having an atmospheric interface arranged between the first and second regions, wherein the second region may comprise a vacuum chamber that is connected to a vacuum pump and which houses the collision surface (or alternatively a collision gas).

The apparatus may comprise an ion trap or ion guide for trapping or guiding the analyte ions.

The ion analyser may comprise a mass and/or ion mobility analyser or spectrometer.

The apparatus may be arranged and configured to perform any one of the methods described herein.

The mixing region may be provided upstream of the inlet to the ion analyser, or the mixing region may be provided at least in part downstream of the ion analyser.

The inlet of the ion analyser may be an aperture or orifice that separates a vacuum chamber of the ion analyser from a higher pressure region upstream of the ion analyser. For example, the inlet may comprise an atmospheric pressure interface.

The matrix introduction conduit may deliver matrix directly into a sample transfer conduit that performs the step of providing the analyte.

Alternatively, a sample transfer conduit may be provided that performs the step of providing the analyte and the outlet of the matrix introduction conduit may be provided at a location about the circumference of sample transfer conduit. A gas flow may be arranged so as to sweep the matrix from the outlet to the inlet of the ion analyser that analyses the ions.

The apparatus may comprise a source of the lockmass, lock mobility or calibration compound or ions.

The lockmass, lock mobility or calibration compound/ions may be introduced into the matrix introduction conduit, the analyte introduction conduit or may be supplied in a separate conduit.

According to the embodiments, aerosol particles containing the analyte (or gas phase analyte molecules) may be introduced into a mass spectrometer together with a volatile matrix compound, which may be an organic solvent. The volatile matrix compound may be introduced to the analyte as a solid (e.g., powder), liquid, aerosol or vapour. The mixture of analyte and matrix may be drawn into the mass spectrometer by a pressure differential across the inlet to the spectrometer. The lower pressure inside the mass spectrometer results in the gas that entrains the analyte and matrix expanding, causing a temperature drop in the free jet region. This causes gaseous or vapourised analyte and/or matrix to condense such that the analyte dissolves in the matrix. The role of the matrix compound may be to produce aerosol particles containing the matrix in excess of the analyte molecules and incorporating the analyte molecules in solvated form. The solvation substantially eliminates the intermolecular secondary binding forces between the analyte molecules, since each dissolved analyte molecule is fully surrounded by the matrix molecules. The separation of analyte molecules in condensed phase increases the probability that when the aerosol particles impact upon the collision surface they will form clusters that each contain only a single analyte molecule. The matrix molecule may have a high dielectric constant and/or a high vapour pressure.

BRIEF DESCRIPTION OF THE DRAWINGS

Various embodiments will now be described, by way of example only, and with reference to the accompanying drawings in which:

FIG. 9A shows a mass spectrum obtained using a lockmass compound and FIG. 9B shows a mass spectrum obtained without using a lockmass compound;

FIG. 13A shows a mass spectrum obtained using a collision surface that is not heated and FIG. 13B shows a mass spectrum obtained using a heated collision surface;

FIGS. 16B-16I show the mass spectra obtained at the different distances of FIG. 16A;

FIGS. 17B-17I show the mass spectra obtained at the different distances of FIG. 15A;

FIGS. 20B-20G show the mass spectra obtained at the different distances of FIG. 20A;

FIG. 22A shows a mass spectrum obtained in negative ion mode without the introduction of a matrix into the analyte stream and without the use of a collision surface, FIG. 22B shows a mass spectrum obtained with the introduction of a matrix into the analyte stream and without the use of a collision surface, and FIG. 22C shows a mass spectrum obtained with the introduction of a matrix into the analyte stream and with the use of a collision surface;

FIG. 22B shows a mass spectrum obtained with the introduction of a matrix into the analyte stream and without the use of a collision surface, and FIG. 22C shows a mass spectrum obtained with the introduction of a matrix into the analyte stream and with the use of a collision surface;

FIG. 24A shows a mass spectrum obtained from the analysis of normal breast tissue without the use of a matrix, and FIG. 24B shows a mass spectrum obtained from the analysis of normal breast tissue with the use of a matrix;

DETAILED DESCRIPTION

Figure 1:
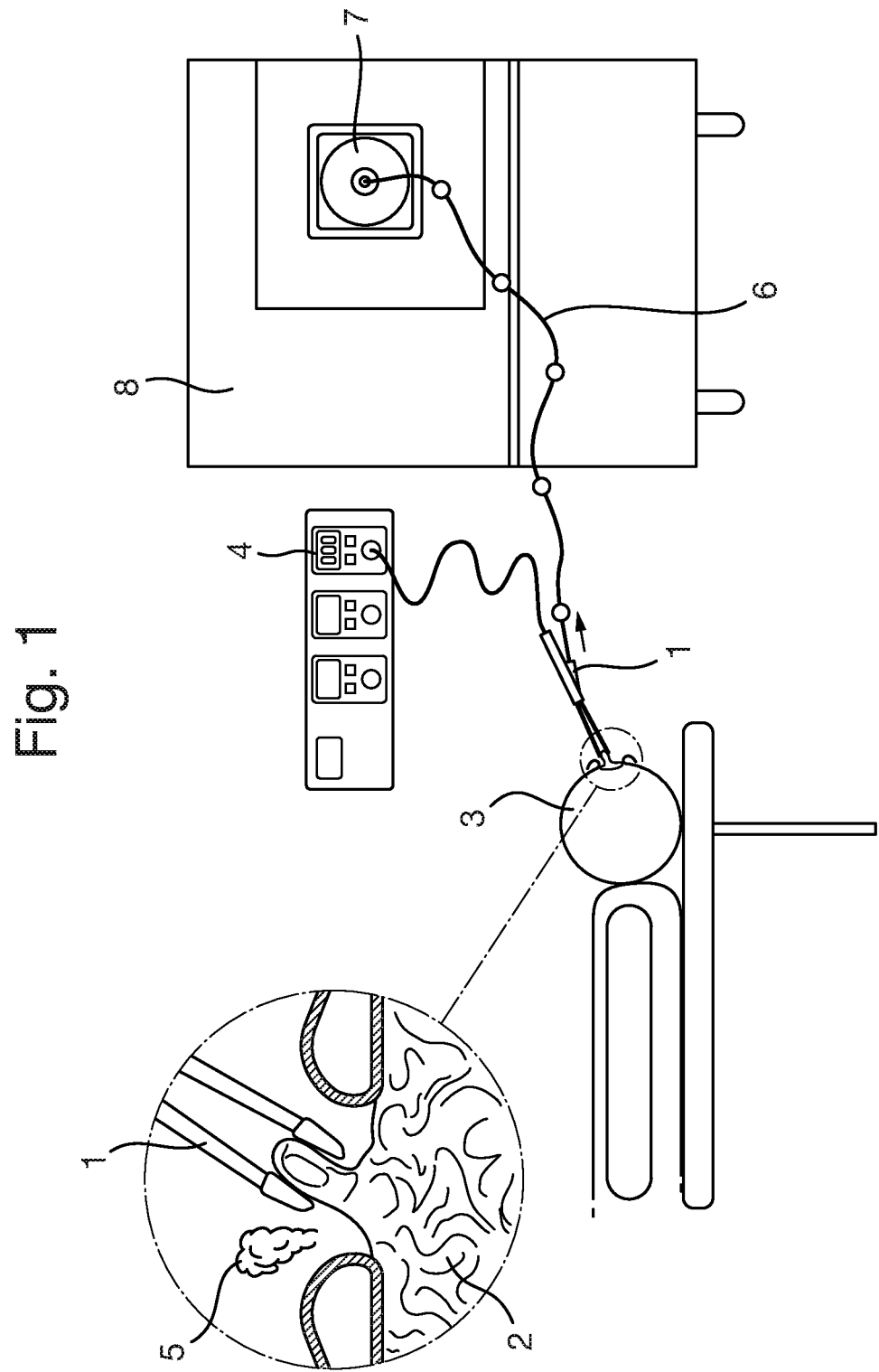
FIG. 1 illustrates a method of rapid evaporative ionisation mass spectrometry ("REIMS") wherein an RF voltage is applied to bipolar forceps resulting in the generation of an aerosol or surgical plume which is captured through an irrigation port of the bipolar forceps and is then transferred to a mass spectrometer for ionisation and mass analysis.

Various embodiments will now be described in more detail below which in general relate to generating an aerosol, surgical smoke or vapour from one or more regions of a target (e.g., in vivo tissue) using an ambient ionisation ion source.

The aerosol, surgical smoke or vapour is then mixed with a matrix and aspirated into a vacuum chamber of a mass spectrometer. The mixture is caused to impact upon a collision surface causing the aerosol, smoke or vapour to be ionised by impact ionisation which results in the generation of analyte ions.

The resulting analyte ions (or fragment or product ions derived from the analyte ions) are then mass and/or ion mobility analysed and the resulting mass and/or ion mobility spectrometric data may then be subjected to multivariate analysis in order to determine one or more properties of the target in real time.

For example, the multivariate analysis may enable a determination to be made as to whether or not a portion of tissue which is currently being resected is cancerous or not.

Ambient Ionisation Ion Sources

According to various embodiments a device is used to generate an aerosol, smoke or vapour from one or more regions of a target (e.g., in vivo tissue). The device may comprise an ambient ionisation ion source which is characterised by the ability to generate analyte aerosol, smoke or vapour, e.g., from a native or unmodified target. The aerosol, smoke or vapour may then be mixed with a matrix and aspirated into a vacuum chamber of a mass and/or ion mobility spectrometer. The mixture may be caused to impact upon a collision surface causing the aerosol, smoke or vapour to be ionised by impact ionisation which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target, e.g., in real time. For example, the multivariate analysis may enable a determination to be made as to whether or not a portion of tissue which is currently being resected is cancerous or not.

It will be apparent that the requirement to add a matrix or a reagent directly to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent to the sample (and hence are suitable for the analysis of in vivo tissue) and since secondly they enable a rapid simple analysis of target material to be performed. For example, other types of ionisation ion sources such as Matrix Assisted Laser Desorption Ionisation ("MALDI") ion sources require a matrix or reagent to be added to the sample prior to ionisation.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |

-continued

| Acronym | Ionisation technique |
| --- | --- |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 μm which corresponds with the peak in the water absorption spectrum. According to various embodiments the ambient ionisation ion source may comprise a laser ablation ion source having a wavelength close to 2.94 μm on the basis of the high absorption coefficient of water at 2.94 μm. According to an embodiment the laser ablation ion source may comprise a Er:YAG laser which emits radiation at 2.94 μm.

Other embodiments are contemplated wherein a mid-infrared optical parametric oscillator ("OPO") may be used to produce a laser ablation ion source having a longer wavelength than 2.94 μm. For example, an Er:YAG pumped ZGP-OPO may be used to produce laser radiation having a wavelength of e.g. 6.1 μm, 6.45 μm or 6.73 μm. In some situations it may be advantageous to use a laser ablation ion source having a shorter or longer wavelength than 2.94 μm since only the surface layers will be ablated and less thermal damage may result. According to an embodiment a Co:MgF2 laser may be used as a laser ablation ion source wherein the laser may be tuned from 1.75-2.5 μm. According to another embodiment an optical parametric oscillator ("OPO") system pumped by a Nd:YAG laser may be used to produce a laser ablation ion source having a wavelength between 2.9-3.1 μm. According to another embodiment a CO2 laser having a wavelength of 10.6 μm may be used to generate the aerosol, smoke or vapour.

According to other embodiments the ambient ionisation ion source may comprise an ultrasonic ablation ion source, or a hybrid electrosurgical-ultrasonic ablation source that generates a liquid sample which is then aspirated as an aerosol. The ultrasonic ablation ion source may comprise a focused or unfocussed ultrasound.

According to an embodiment the first device for generating aerosol, smoke or vapour from one or more regions of a target may comprise an tool which utilises an RF voltage, such as continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

According to an embodiment the first device comprises a surgical water/saline jet device such as a resection device, a hybrid of such device with any of the other devices herein, an electrosurgery argon plasma coagulation device, a hybrid argon plasma coagulation and water/saline jet device.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimeters.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices. As the non-contact device may not make physical contact with the tissue, the procedure may be seen as relatively safe and can be used to treat delicate tissue having low intracellular bonds, such as skin or fat.

Rapid Evaporative Ionisation Mass Spectrometry ("REIMS")

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated. The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of a mass spectrometer 8.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the mass spectrometer 8. According to one embodiment the collision surface may be heated. The aerosol is caused to ionise upon impacting the collision surface resulting in the generation of analyte ions. The ionisation efficiency of generating the analyte ions may be improved by the addition of the organic solvent (i.e. the matrix).

Analyte ions which are generated by causing the aerosol, smoke or vapour 5 to impact upon the collision surface are then passed through subsequent stages of the mass and or ion mobility spectrometer and are subjected to mass and/or ion mobility analysis in a mass and/or ion mobility analyser. The mass analyser may, for example, comprise a quadrupole mass analyser or a Time of Flight mass analyser.

Figure 2:
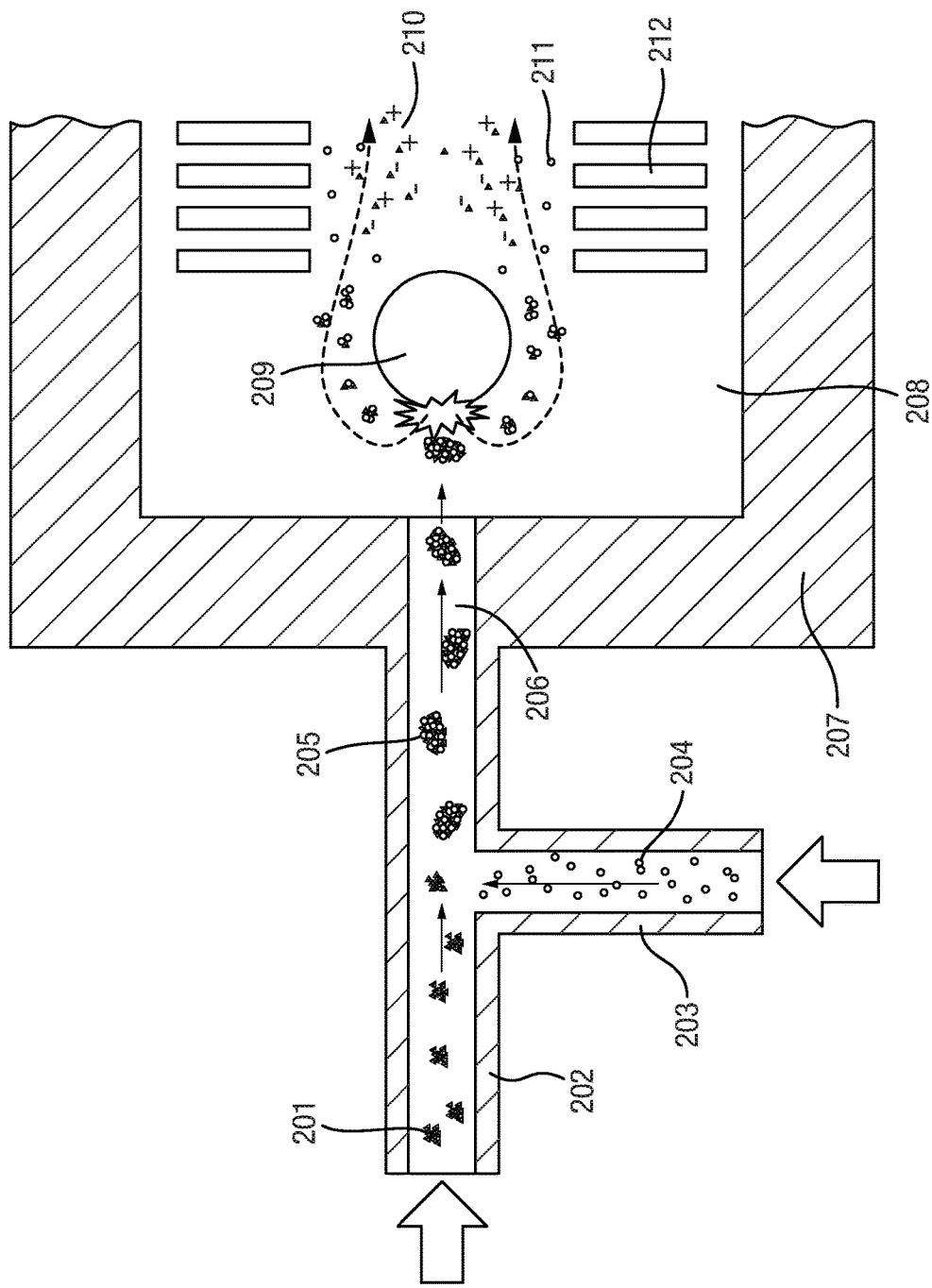
FIG. 2 shows an embodiment in which the analyte and matrix may be provided in the gas or vapour phase.

FIG. 2 shows a schematic of an embodiment. The device may comprise an ion analyser 207 having an inlet 206, a vacuum region 208, a collision surface 209 and ion optics 212 such as a Stepwave® ion guide arranged within the vacuum region 208. The device also may comprise a sample transfer tube 202 and a matrix introduction conduit 203. The sample transfer tube 202 has an inlet for receiving aerosol sample 201 (which may correspond to the aerosol or surgical plume 5 described in relation to FIG. 1) from a sample being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202. A T-junction component may be provided at the junction between tubes 202, 203 and 206. The tubes 202, 203 and 206 may be removably inserted into the T-junction.

A method of operating the device of FIG. 2 will now be described. A sample, such as a biological sample, may be subjected to the REIMS technique. For example, a diathermic device may be used to evaporate biological tissue from the sample so as to form an aerosol, e.g., as described above in relation to FIG. 1. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on the collision surface 209, where the impact event fragments the particles 205, leading to the eventual formation of gas phase ions 210 of the molecular constituents of the aerosol sample 201 and the formation of matrix molecules 211. The collision surface 209 may be controlled and maintained at a temperature that is substantially higher than the ambient temperature.

The matrix 204 may include a solvent for the analyte 201, such that the analyte 201 may dissolve in the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include an organic solvent and/or a volatile compound. The matrix may include polar molecules, water, one or more alcohols, methanol, ethanol, isopropanol, acetone or acetonitrile. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212. The ions are then analysed by the ion analyser, which may comprise a mass spectrometer 102 or an ion mobility spectrometer, or a combination of the two. As a result of the analysis, chemical information about the sample 201 may be obtained.

Figure 3:
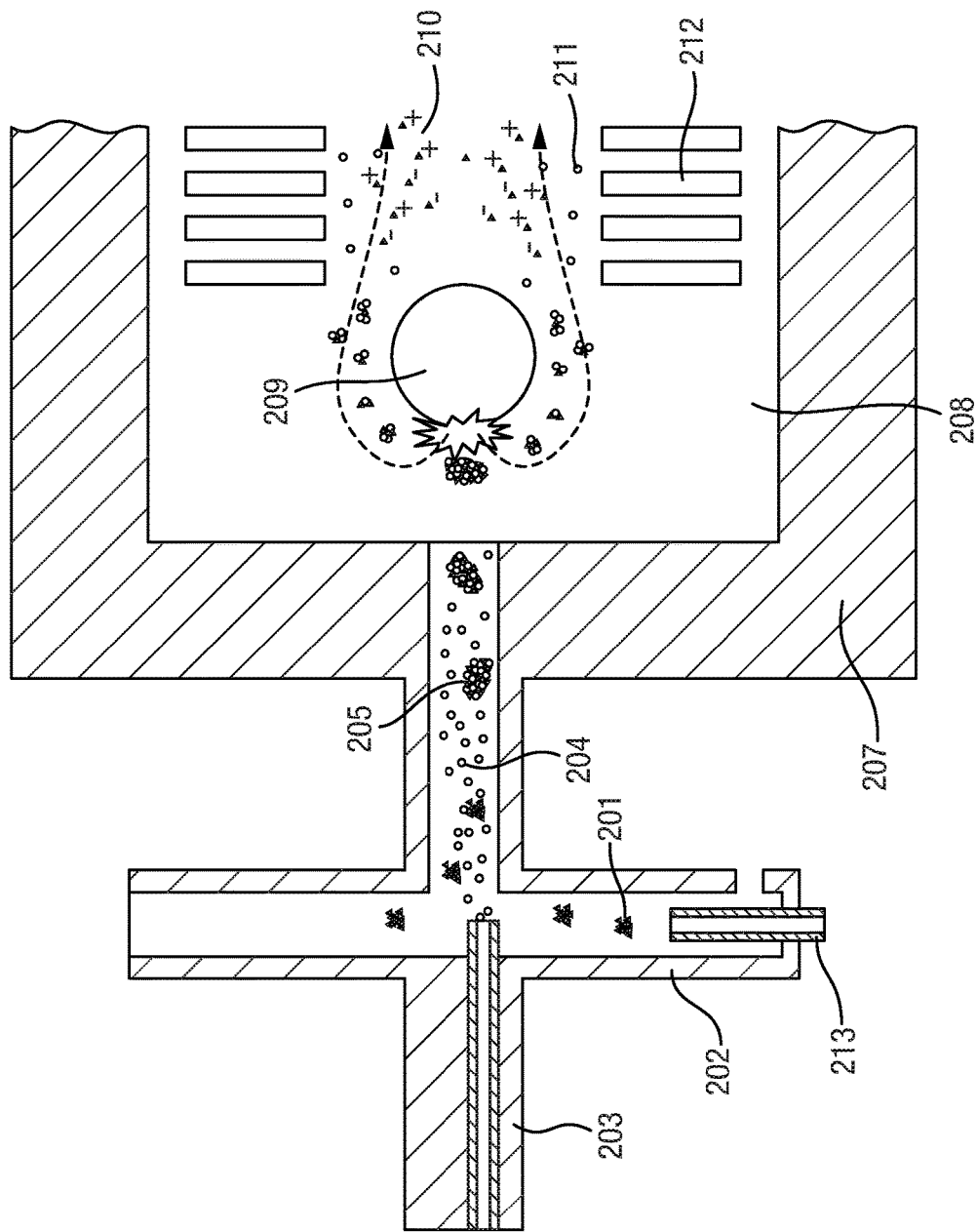
FIG. 3 shows another embodiment in which the analyte and matrix may be provided in the liquid phase.
Figure 4A:
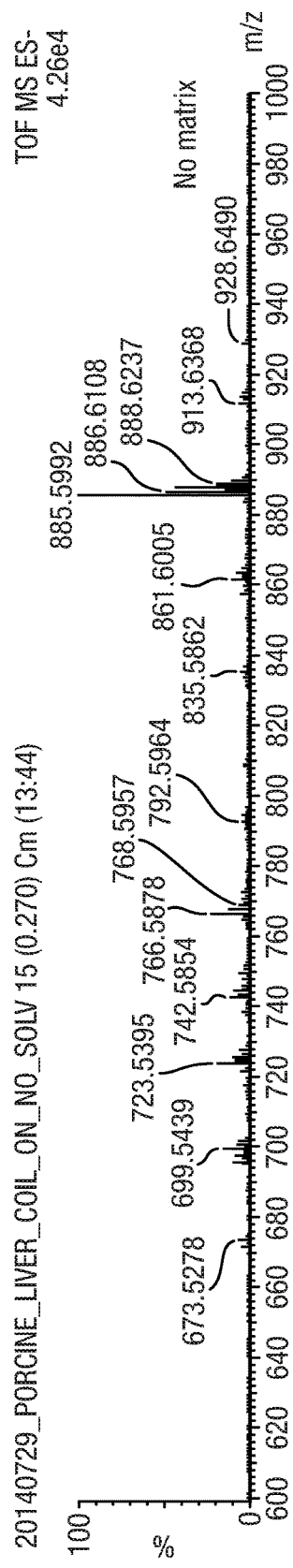
FIG. 4A shows a mass spectrum obtained without the use of a matrix and FIG. 4B shows a mass spectrum obtained using a matrix.
Figure 4B:
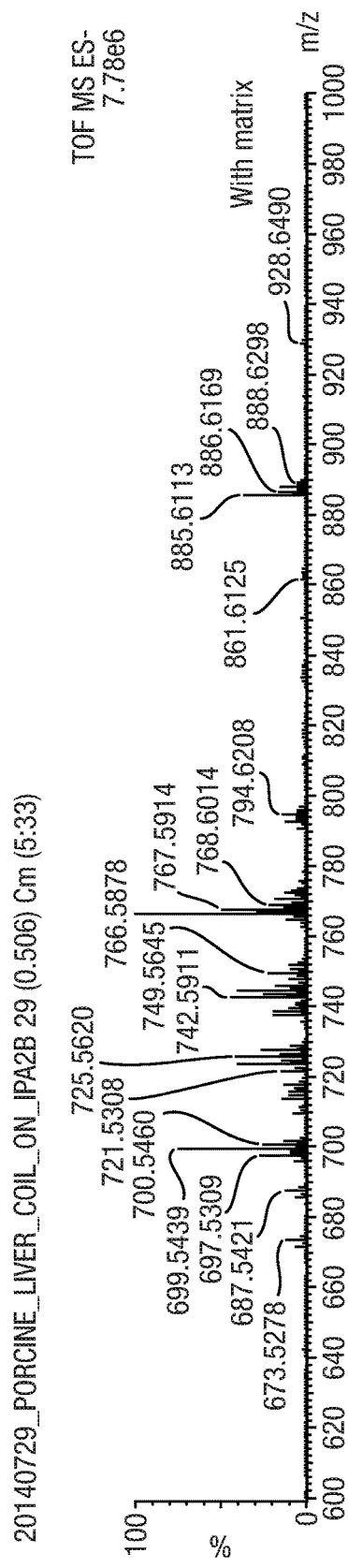

FIG. 3 shows a schematic of an embodiment that is substantially similar to that shown and described in relation to FIG. 2, except that the sample 201 is delivered by a fluid/liquid transfer pump or a Venturi pump 240 and the matrix 204 may be delivered in liquid form. This allows the matrix compound 204 to be mixed into the aerosol 201 as a vapour, or as a liquid, prior to introduction into the ion analyser 207.

The Venturi pump 240 may comprise an inlet tube 242 that may be connected to a device or probe (e.g., a REIMS device or probe as described herein) and may be configured to transport aerosol particles or liquid from a sample (e.g., biologic tissue) to the Venturi pump 240.

The Venturi pump may comprise a gas inlet 244 that may be arranged and adapted to introduce a gas (e.g., nitrogen or standard medical air) into the flow path of the aerosol particles 201 or liquid being transported into the Venturi pump 240 by the inlet tube 242. The Venturi pump 240 may therefore facilitate the aspiration of aerosol particles 201 or other gaseous sample containing the analyte. The Venturi pump also comprises an exhaust 246 for exhausting the Venturi gas from the system such that it is not directed into the vacuum chamber 208 of the mass spectrometer 207.

The Venturi pump 240 may comprise a sample transfer portion or capillary 202 that may be arranged and adapted to direct the sample and gas mixture produced by the Venturi pump 240 towards a junction 248. A matrix introduction conduit 203 is arranged and adapted to introduce matrix or a matrix compound 204 into the junction 248 and direct the flow of the matrix compound 204 towards an inlet tube 206.

The aerosol particles 201 and the matrix 204 may intermix at the junction 248 and the resulting aerosol particles 205 may be carried into the inlet tube 206 by the suction from the vacuum chamber 208. The larger aerosol particles 201 may be too heavy to be carried into the inlet tube 206 and may travel past the junction 248 and leave the apparatus via the exhaust 246.

Whilst shown as contiguous in FIG. 3, the sample transfer portion 202 may be a separate component from the junction 248 and inlet tube 206. The junction 248 may comprise a connector or connecting portion (not shown) for connecting to a separate sample transfer portion 202. The connection between the junction 248 and the sample transfer portion 206 may be fluidly sealed and/or may comprise a ring clamp.

As described hereinabove, an important feature is the formation of molecular clusters 205 containing the original analyte aerosol constituents 201 and the matrix compound 204, followed by the surface-induced dissociation of these clusters 205. The benefit of using a matrix 204 in accordance with an embodiment can be seen from FIG. 4A and FIG. 4B.

FIG. 4A shows a mass spectrum obtained by subjecting a sample to a REIMS technique in which an aerosol was generated from a target, the aerosol was collided with a heated collision surface and the resulting ions generated therefrom were mass analysed. The mass spectrum in FIG. 4B was obtained by subjecting the same sample to the same analysis technique except that the aerosol was mixed with a matrix (isopropanol) before being collided with the collision surface and then mass analysed. It can be seen from the two mass spectra in FIGS. 4A and 4B that the use of a matrix substantially increases the intensity of ions detected.

It is thought that there are several mechanisms by which the addition of the matrix may improve ionisation of the analyte. For example, mechanisms that result in protonation or deprotonation of the analyte may occur. Alternatively, or additionally, reactions that involve the removal of water and/or ammonia from the analyte may occur. Alternatively, or additionally, the adducting of metal ions such as sodium may play a role in the mechanism. The most probable mechanisms of protonation or deprotonation are analogous to MALDI methods.

It is thought that the dominant mechanism by which the addition of the matrix improves ionisation of the analyte is by diluting or dissolving the analyte so as to facilitate the formation of analyte ions in solution phase by ionic dissociation. The sample being analysed may contain counter ions, such as $Na^+$, $K^+$, $H_3O^+$ etc, which interact with the analyte so as to facilitate the formation of the solution phase analyte ions. The resulting analyte ions may then be separated from the matrix in the gas phase (e.g., after collision with the collision surface and/or evaporation) on collision with the surface, via desolvation, or via the so called MALDI lucky survivor mechanism.

It is thought that, dependent upon the matrix characteristics, a possible mechanism of matrix enhancement of ionisation in ambient ionisation techniques, such as REIMS, involves the formation of matrix (M) ions and analyte (A) ions in solution, as follows.

$$A + M \underset{Solution}{\Longleftrightarrow} [A-H]^- + [M+H]^+$$

$$A + M \underset{Solution}{\Longleftrightarrow} [A+H]^+ + [M-H]^-$$

Alternatively, the ionisation of the analyte may occur in the gas phase, e.g., as described in Biochimica et Biophysica Acta 1458 (2000) 6-27. However, this mechanism is thought to be energetically less favourable. The formation of matrix (M) ions and analyte (A) ions in the gas phase may proceed as follows:

$$A + M \underset{Gas\ Phase}{\Longleftrightarrow} [A-H]^- + [M+H]^+$$

$$A + M \underset{Gas\ Phase}{\Longleftrightarrow} [A+H]^+ + [M-H]^-$$

The ionisation may occur in the gas phase or in the liquid phase. As the droplets containing the matrix and analyte molecules rapidly desolvate on contact with the collision surface, this brings them into the gas phase in close proximity and high concentration.

The proton exchange may occur via two different types of transition. As there is a potential barrier to the transfer, the proton exchange may occur via an over barrier transition or an under barrier (tunnelling) transition. The probability of the under barrier transition depends on the form of the barrier and on the energy (E) of the particle which is to tunnel. The energy dependence is very strong and is approximately an exponential of the form exp(E/ΔE), where ΔE is the energy characteristic for a given barrier. Accounting for the probability of the proton to be at the energy level E, the 'pure' tunnelling probability is required to be multiplied by the Boltzmann factor exp(−E/kT). Accordingly, the total contribution of the level E is proportional to exp(E/ΔE−E/kT).

Therefore, there are two limiting cases. If ΔE>>kT, then the probability tends to exp(−E/kT), and the most probable mechanism is quantum behaviour by tunnelling from the ground state. Alternatively, if ΔE<<kT, then the proton is most likely to be at the highest possible level of E, i.e. at the top of the barrier, and so the most probable mechanism of transfer is an over barrier transition. For the first limiting case, the probability of proton transfer depends strongly on the overlap of its vibrational wave functions, thus the degree of ionisation enhancement observed by the introduction of the matrix will be specific to the given analyte and given matrix M. This is what is observed, for example, with reference to FIGS. 4A-4B in which it is clear that the enhancement in ionisation due to the addition of the matrix for ions of mass 766.6 Da is greater than that for ions of mass 885.6 Da.

Another possible mechanism, which is again analogous to MALDI mechanisms, is a two-step process. The first step is the formation of primary matrix (M) ions in the matrix-analyte solution, as follows:

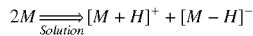

$$2M \xrightleftharpoons[Solution]{} [M+H]^+ + [M-H]^-$$

According to Knockenmuss (Analyst 2006, 131 966-986), this remains the most controversial aspect of the two-step process.

The second step of the process may involve ion-molecule reactions in the plume that forms as the droplets strike the collision surface (which may or may not be heated), as follows:

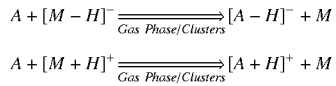

$$A + [M-H]^- \xrightleftharpoons[Gas\ Phase/Clusters]{} [A-H]^- + M$$
$$A + [M+H]^+ \xrightleftharpoons[Gas\ Phase/Clusters]{} [A+H]^+ + M$$

Further desolvation, in the case of cluster formation, may result in separation of the charged molecular ions.

Figure 5A:
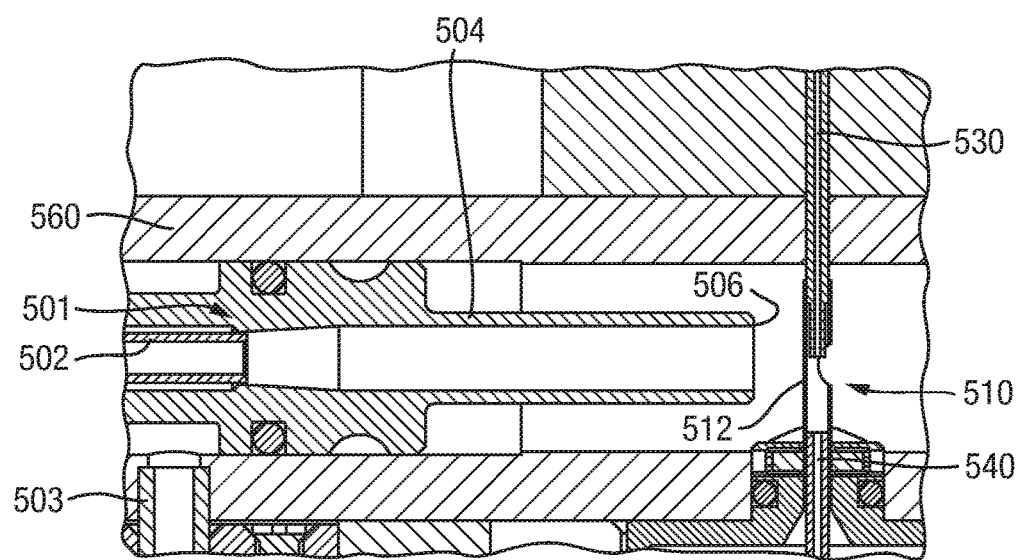
FIG. 5A shows an embodiment of a mass spectrometer interface comprising a Venturi device for introducing analyte aerosol and matrix into a mass spectrometer.

FIG. 5A shows another embodiment of a mass spectrometer interface for introducing the analyte aerosol and matrix into the mass spectrometer. The instrument comprises a Venturi pump 501. The Venturi pump 501 comprises a tube 502 that may be connected to a device or probe (e.g., a REIMS device or probe as described herein) and may be configured to transport aerosol particles from a sample (e.g., biologic tissue) to the Venturi pump 501. The Venturi pump 501 may comprise a gas inlet 503 that may be arranged and adapted to introduce a gas (e.g., a Venturi gas) into the flow path of the aerosol particles being transported into the Venturi pump 501 by the tube 502. The Venturi pump 501 may comprise an elongated sample transfer tube 504 that may be arranged and adapted to transfer the sample and gas mixture from the tube 502 onto a sampling device 510 via an outlet end 506 of the sample transfer tube 504.

The sampling device 510 may broadly comprise a hollow tube or whistle 512, a matrix introduction conduit 530 and an inlet tube 540. The matrix introduction conduit 530 may be arranged and adapted to introduce a matrix in liquid form through a channel 534 (FIG. 5B) within the matrix introduction conduit 530. Matrix leaves the matrix introduction conduit 530 through an end 534 disposed or located within the whistle 512 and it may be nebulised by a gas that is being drawn into the inlet tube 540. The quality of nebulisation of the matrix may be controlled and affected by the dimensions and/or relative distances between the various parts of the sampling device 510, as described in more detail below.

The inlet tube 540 leads to an inlet of a ion analyser or mass spectrometer and may be arranged and adapted such that a mixture of sample, gas and matrix passes through an end 542 of the inlet tube 540 disposed or located within the whistle 512 and through a passage 544 to be transferred into a ion analyser or mass spectrometer. In these arrangement the collision surface 209 is arranged downstream of the inlet tube 540.

Figure 5B:
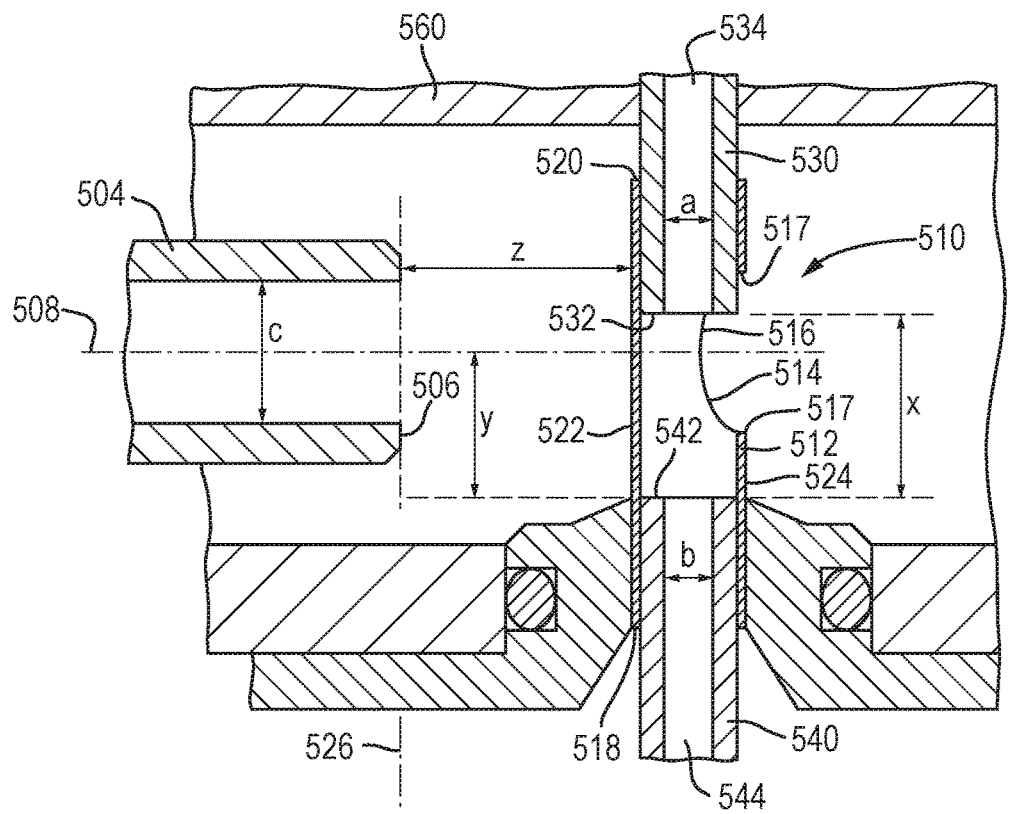
FIG. 5B shows an expanded view of FIG. 5B.
Figure 5C:
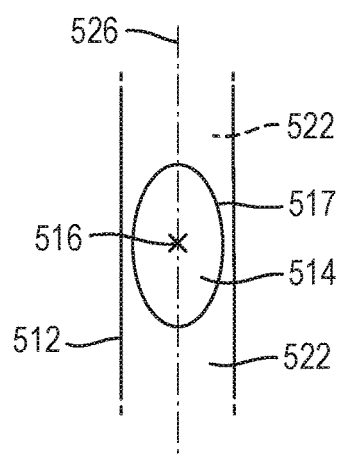
FIG. 5C shows a close up of the sampling device in the interface.
Figure 6:
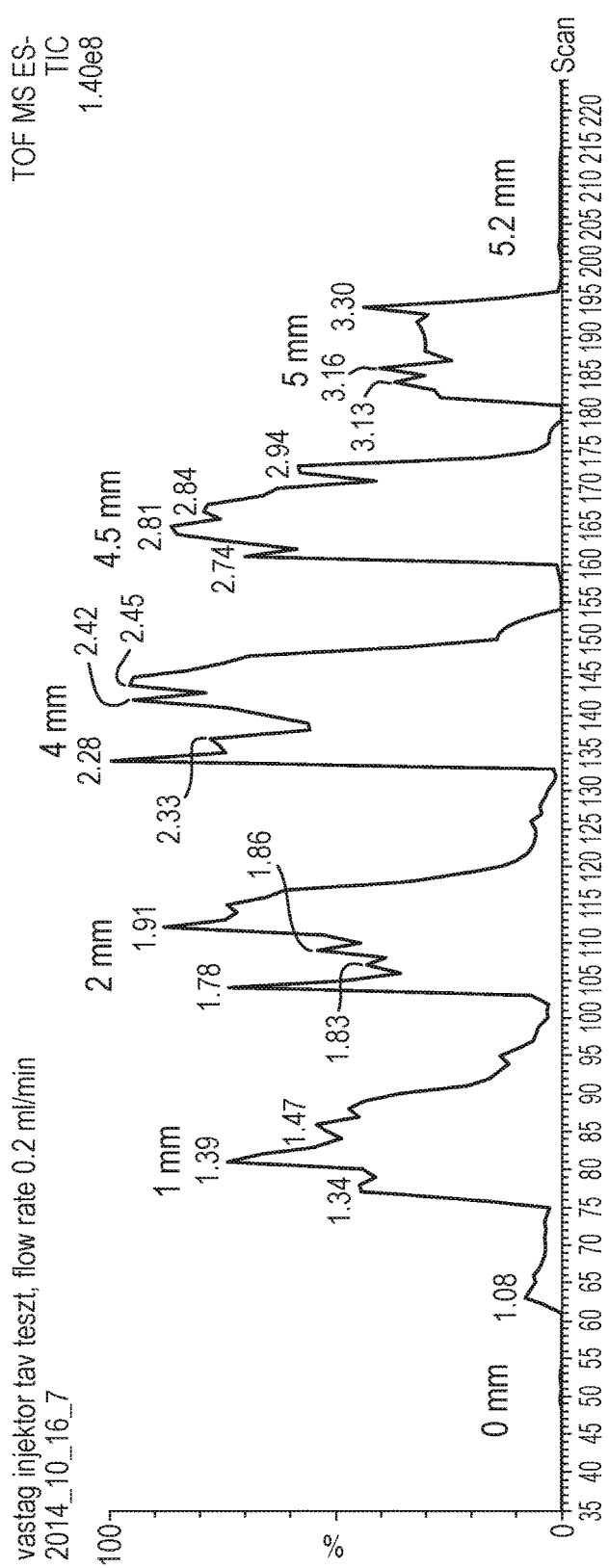
FIG. 6 shows how the ion signal detected using the embodiment of FIG. 5 varies depending on the distance between the outlet of the matrix conduit and the inlet of the ion analyser.
Figure 7:
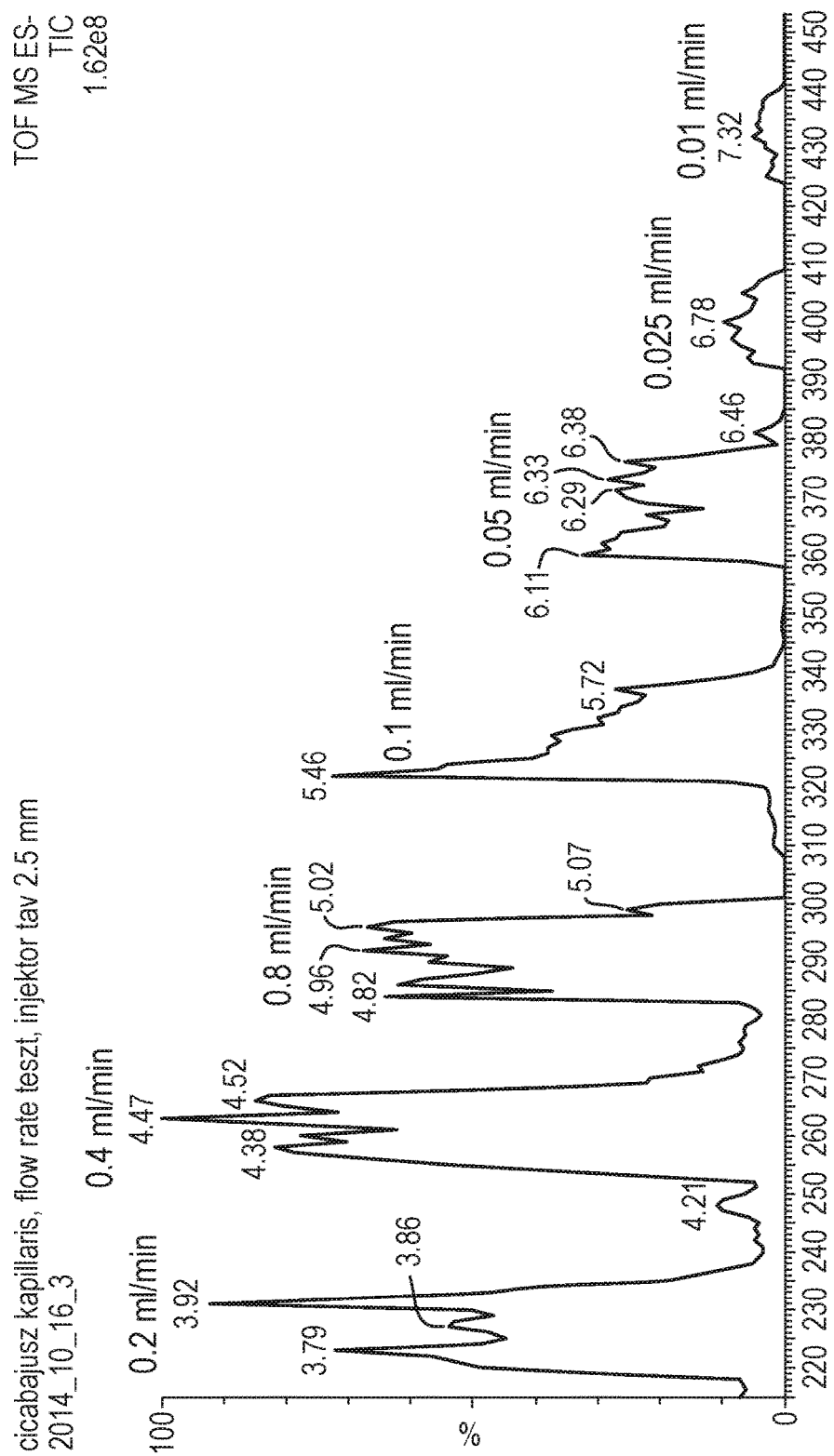
FIG. 7 shows how the ion signal detected using the embodiment of FIG. 5 varies depending on flow rate of the matrix.
Figure 8A:
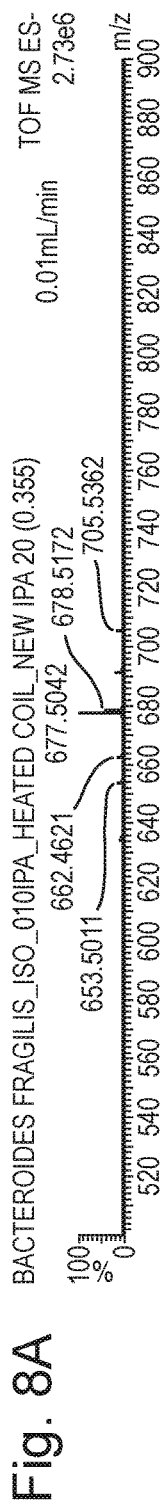
FIGS. 8A-8I show mass spectra obtained using different isopropanol matrix flow rates.
Figure 8B:
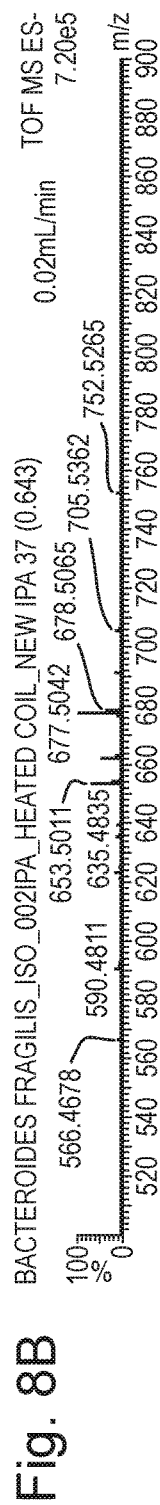
Figure 8C:
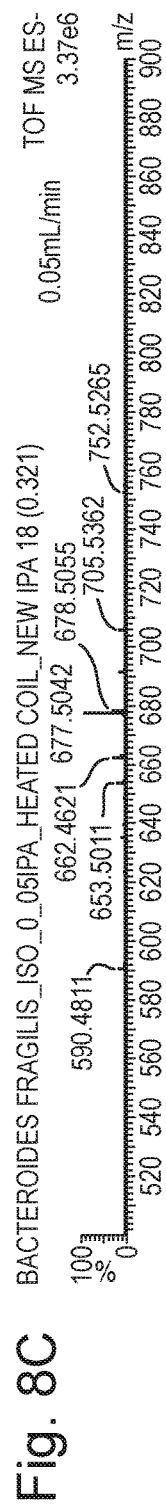
Figure 8D:
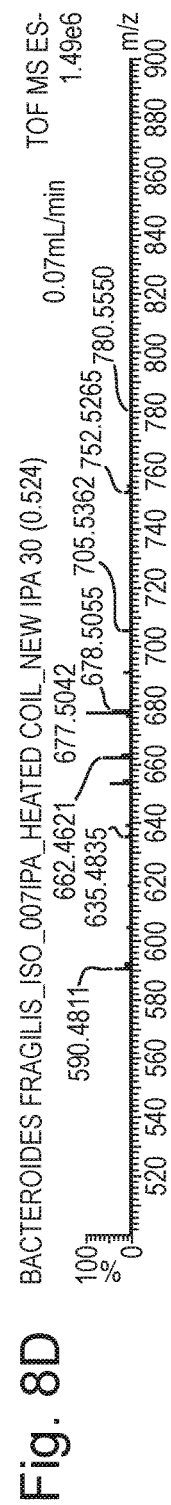
Figure 8E:
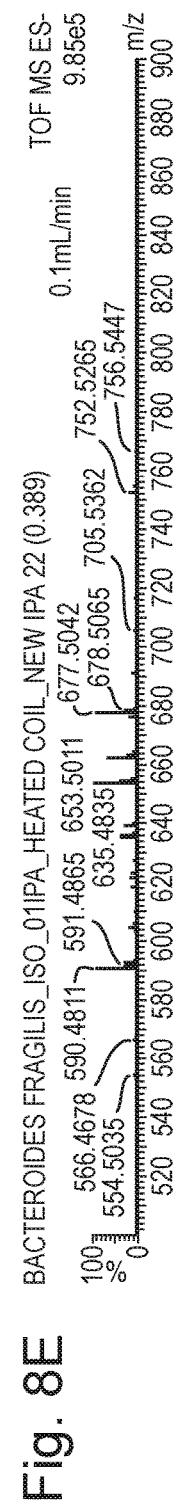
Figures 8F, 8G, 8H, 8I:
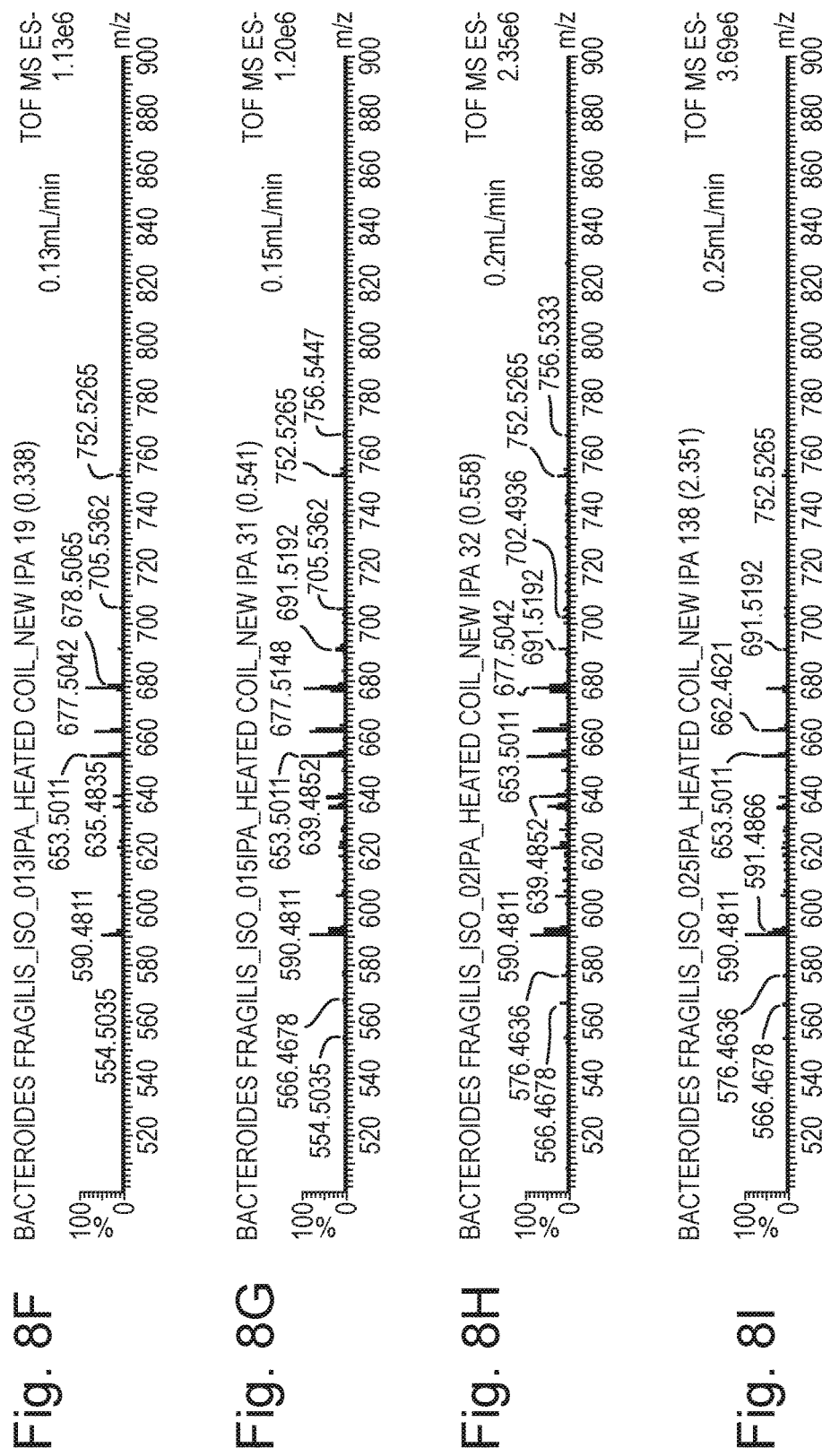

FIG. 5C shows a close-up view of the sampling device 510.

The whistle 512 may be provided in the form of a hollow tube optionally having a first side 522 that may be arranged so as to face the outlet end 506 of the sample transfer tube 504, and a second, opposite side 524 optionally facing away from the outlet end 506 of the sample transfer tube 504.

The whistle 512 may comprise a first end 518 that may be located concentrically around the inlet tube 540 and may be in sealing engagement therewith. The whistle may comprise a second end 520 that may be located concentrically around the matrix introduction conduit 530 and may be in sealing engagement therewith.

A void, aperture or cut-out 514 may be provided on the second side 524 of the whistle 512, and the cut-out 514 may form an inlet such that the sample and gas mixture flowing past the whistle 512 from the outlet end 506 of the sample transfer tube 504 may transfer into the interior of the whistle 512.

The mixture of sample and gas exiting the outlet end 6 of the sample transfer tube 504 may impact on the first side 522 of the whistle 512, and then travel around the outside surface and into the cut-out 514. Once the sample and gas mixture is in the interior of the whistle, it may mix with the nebulised matrix emerging from the matrix introduction conduit 530 before the mixture of sample, gas and matrix is optionally transferred into the inlet tube 540 through the end 542 of the inlet tube 540. The mixture of sample, gas and matrix may then be transferred via the passage 544 to an ion analyser or mass spectrometer.

Positioning the cut-out 514 on the second side 524 of the whistle 512 means that the initial impact of the sample and gas mixture is on a surface that is not directly exposed to the vacuum of the mass spectrometer. In various embodiments, therefore, the sampling device 510 is arranged and adapted such that the initial impact of the sample and gas mixture is on a surface that is not directly exposed to the vacuum of the mass spectrometer.

The cut-out 514 may have a substantially semi-circular profile when the whistle 512 is viewed in cross-section (as shown, for example, in FIGS. 5A and 5B). This will mean that the edge 517 of the cut-out 514 is oval when viewed from a direction facing the second side 524 of the whistle 512 (see FIG. 5C). Alternatively, the cut-out 514 may have a different shape profile when the whistle 512 is viewed in cross-section, for example a square, triangular or irregular shaped profile. The edge 517 of the cut-out 514 may also be square, triangular or irregular when then whistle 512 is viewed from a direction facing the second side 524 of the whistle 12 (see FIG. 5C).

The position and orientation of the whistle 512 can affect the quantity and quality of sample that is transferred into the mass spectrometer. The cut-out 514 may comprise a centre point 516 which may be in line with a longitudinal centreline 508 of the sample transfer tube 504. FIG. 5C shows a view of the second side 524 of the whistle 512 (the whistle 512 is shown in isolation in FIG. 5C), and the centre point 516 can be seen as the centre point of the oval.

The whistle 512 may be oriented such that longitudinal axis 526 of the whistle lies coincident with an axis of symmetry of the cut-out 514. The centre point 516 may lie on the longitudinal axis 526 of the whistle 512 and/or an axis of symmetry of the cut-out. The axis of symmetry of the cut-out may comprise the longitudinal axis of symmetry, wherein the longitudinal direction may be defined as the direction along the longitudinal axis 526.

The position of the various parts of the sampling device 510 can also affect the quantity and quality of sample that is transferred into the mass spectrometer.

Now referring to FIG. 5B, a distance x is defined as the distance (e.g., the shortest distance) between the end 534 of the matrix introduction conduit 530 and the end 542 of the inlet tube 540.

A distance y is defined as the distance (e.g., the shortest distance) between the centre point 516 of the cut-out 514 and the end 542 of the inlet tube 540.

A distance z is defined as the distance (e.g., the shortest distance) between the outlet end 506 of the sample transfer tube 504 and the whistle 512 (e.g., the first side 522 of the whistle 512).

The diameter a of the matrix introduction conduit 530 can also affect the quantity and quality of sample that is transferred into the mass spectrometer, and can also affect the nebulisation of the matrix as it leaves the end of the matrix introduction conduit 530.

The diameter b of the inlet tube 540, and the diameter c of the sample transfer tube 504 can also affect the quantity and quality of sample that is transferred into the mass spectrometer.

The diameters a, b and c may correspond to the diameters at the end 532 of the matrix introduction conduit 530, the end 542 of the inlet tube and the outlet end 506 of the sample transfer tube 504, respectively.

Any or all of the diameters a, b and c may be greater than, less than or substantially equal to 0.2 mm, 0.4 mm, 0.6 mm, 0.8 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm or 5 mm.

Any or all of the diameters/distances a, b, c, x, y and z may be changed to optimise the quantity and quality of sample that is transferred into the mass spectrometer.

Aspects of the disclosure may extend to methods of optimising the sampling device 510, comprising identifying one or more parameters associated with the sampling device, for example ion abundance or ion signal intensity and changing one or more of the distances a, b, c, x, y and z until the one or more parameters are optimised or at a maximum or minimum value.

The Venturi pump 501 may be for introducing aerosol particles into the sample transfer tube 504. The sampling device 510 may be provided for sampling the aerosol. The matrix introduction conduit 530 may be arranged to introduce a matrix (such as isopropanol) into the sampling device 510 and the inlet tube 540 may be arranged to direct a mixture of aerosol particles and matrix onwards to an ion analyser or mass spectrometer.

The Venturi pump 501 may facilitate the aspiration of aerosol or other gaseous sample containing the analyte and may be driven by nitrogen or standard medical air. Aerosol sampling may be arranged to occur orthogonally to the outlet end 506 of the Venturi pump 501 as shown from FIGS. 1A and 1B. The outlet 532 of the matrix introduction conduit 530 may be spaced apart from the inlet tube 540 to the ion analyser or mass spectrometer by the distance x. The distance x can be modified as required to achieve an optimum ion signal intensity.

Altering the value of the distance x can change the velocity of the gas being drawn into the inlet tube 540 and can have an effect upon the nebulisation conditions. If the nebulisation conditions are less favourable then the matrix droplets may not be of the correct size for interacting with the analyte aerosol and/or may not fragment efficiently when the aerosol collides with the collision surface.

FIG. 6 shows the intensity of an ion signal obtained by an ion analyser 207 for different distances x between the outlet 532 of the matrix introduction conduit 530 and the inlet 540, when the matrix flow rate was set to about 0.2 ml/min. FIG. 6 shows the ion signals for values of x=0 mm, x=1 mm, x=2 mm, x=4 mm, x=4.5 mm, x=5 mm, and x=5.2 mm. It can be seen that when the distance x is about 0 mm (i.e. the outlet of the matrix conduit 530 is touching the inlet 540) then no ion signal is detected. When the distance x is increased to about 1 mm, an ion signal is detected. When the distance x is increased from about 1 mm to about 2 mm, the relative intensity of the ion signal is increased. When the distance x is increased from about 2 mm to about 4 mm, the relative intensity of the ion signal is increased further. When the distance x is increased from about 4 mm to about 4.5 mm, the relative intensity of the ion signal decreases. When the distance x is further increased from about 4.5 mm to about 5 mm, the relative intensity of the ion signal is decreased significantly. When the distance x is increased from about 5 mm to about 5.2 mm, substantially no ion signal is detected. This shows that the ion signal detected can be optimised by selecting an appropriate value of x.

As the matrix 204 leaves the matrix introduction conduit 530 it may be nebulised by the gas that is being drawn into the ion analyser inlet 240. It is believed that altering the value of the distance x changes the velocity of the gas being drawn into the ion analyser inlet 240 and hence affects the nebulisation conditions. If the nebulisation conditions are not favourable then the matrix droplets may not be of the correct size for interacting with the analyte aerosol 201 and/or may not fragment well when collided with the collision surface 209.

The effect of different matrix 204 (e.g., isopropanol) flow rates on the spectral appearance was tested.

FIG. 7 shows the intensity of the ion signal obtained by the ion analyser 207 for different flow rates of matrix 204 when the spacing x between the outlet 232 of the matrix introduction conduit 230 and the inlet 240 to the ion analyser 207 was set at about 2.5 mm. The ion signal was measured at a flow rate about 0.2 ml/min. The flow rate was then increased to about 0.4 ml/min, resulting in an increased intensity of the ion signal. The flow rate was increased further to about 0.8 ml/min, resulting in a decreased intensity of the ion signal. The flow rate was then decreased to about 0.1 ml/min, resulting in a decreased intensity of the ion signal. The flow rate was then decreased further to about 0.05 ml/min, resulting in a further decreased intensity of the ion signal. The flow rate was then decreased further to about 0.025 ml/min, resulting in a further decreased intensity of the ion signal. The flow rate was then decreased yet further to about 0.01 ml/min, resulting in a further decreased intensity of the ion signal. This shows that the ion signal is not necessarily improved simply by increasing the flow rate of the matrix 204, but that the flow rate may be optimised to produce the optimal ion signal intensity.

FIGS. 8A-8I show the effect of different isopropanol flow rates on REIMS spectral profiles for *Bacteroides fragilis*, using flow rates between 0.01 to 0.25 mL/min. FIGS. 8A-8I show spectra for the mass range of 500-900, covering phospholipid analytes. The effect of the isopropanol being present in the analysis of this sample is detectable at very low rates, e.g., from 0.02 mL/min, and is clearly visible from the appearance of m/z 590 (ceramide species) and m/z 752 (α-Galactosylceramide) in the spectra. These species were found to increase in their relative abundance when further increasing the isopropanol flow rate.

Although the matrix has been described in FIG. 5 as being introduced opposite the inlet 240 to the ion analyser 207 and downstream of the sample transfer tube 504, it may alternatively be introduced into the sample transfer tube 504.

Alternatively, the matrix may be introduced at a location around the circumference of the transfer tube 504 and may be swept towards and into the inlet 240 to the ion analyser 207 by a gas flow.

Calibration/lockmass/lock mobility compounds may be used in the various techniques described herein for calibrating the ion analyser or providing a reference mass to the ion analyser. The calibration, lockmass or lock mobility compound may be introduced via the matrix introduction conduit 203, via the sample transfer tube 202, or in another location.

FIG. 9A and FIG. 9B show two mass spectra obtained by analysing a sample of porcine muscle according to an embodiment. The spectrum of FIG. 9A was obtained whilst introducing a lockmass compound (Leu-enk) into the analyser 207 through the matrix conduit 203. The peaks for the lockmass compound can be observed as the first peaks in the mass spectrum. The mass to charge ratios of the lockmass ions are known in advance and can be used to calibrate the mass analyser 207 such that the mass to charge ratios of the other ions detected can be determined more accurately. The mass spectrum shown in FIG. 9B was obtained using the same method as the spectrum in FIG. 9A, except that no lockmass compound was used in the analysis. It can be seen that the two mass spectra are substantially identical, except for the detection of the lockmass ions in the mass spectrum of FIG. 9A. It is therefore apparent that the introduction of a lockmass compound in the technique does not affect the mass spectra measured by the ion analyser 207.

Figure 10:
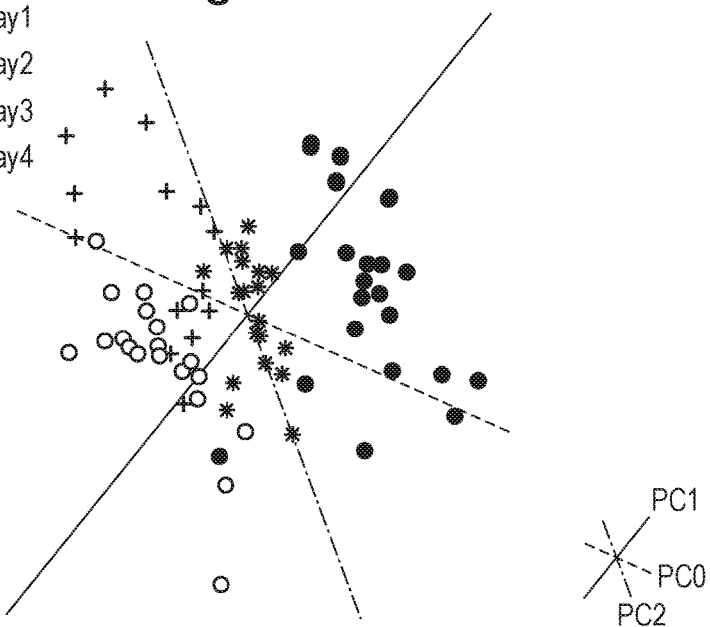
FIG. 10 shows the results of a principle component analysis on data obtained over different days, both with and without the use of lockmass ions.

FIG. 10 shows a plot resulting from a principle component analysis of porcine brain over four days. The data for Day 1 and Day 4 was obtained without the use of a lockmass compound, whereas the data for Day 2 and Day 3 was obtained with the use of a lockmass compound. The analysis was performed over the range of 600-900 mass units and so the lockmass ions are not shown in the plot, as the lockmass ions are outside of this range (see FIG. 9A). The principle component analysis shows that the data obtained with use of the lockmass compound is not separable from the data obtained without use of the lockmass compound, and that the variance due to the data being from different days is significantly greater than any variance due to the inclusion of the lockmass compound.

Figure 11:
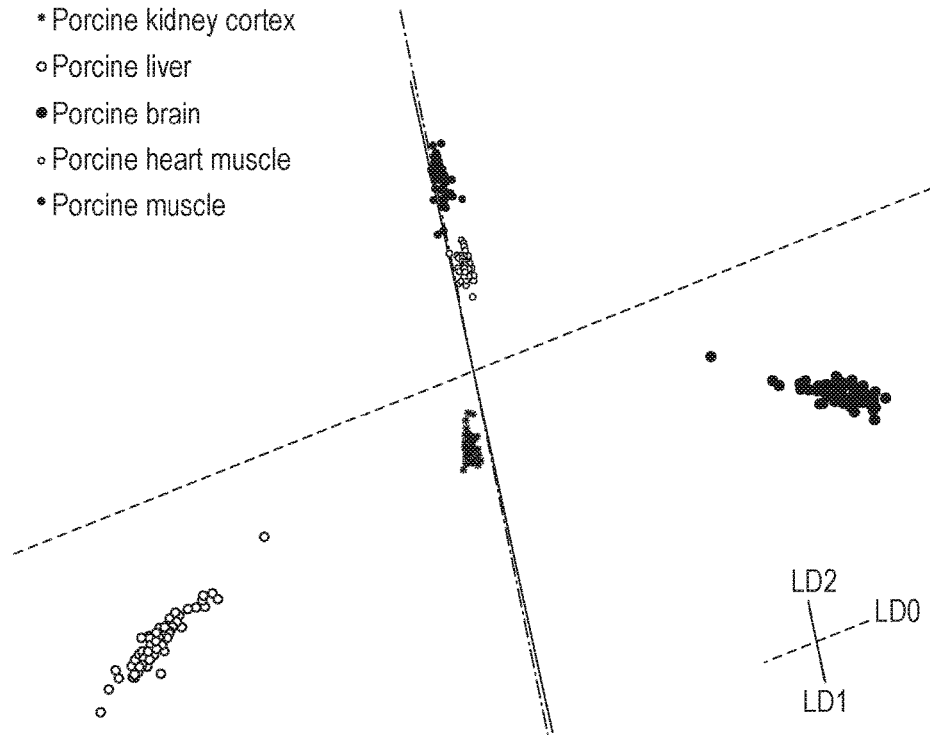
FIG. 11 shows the results of a principle component analysis on data obtained for different tissue types, both with and without the use of lockmass ions.

FIG. 11 shows the results of a principle component analysis for the analysis of data obtained from porcine kidney cortex, porcine liver, porcine brain, porcine heart muscle and other porcine muscle. Some of the data was obtained using a lockmass compound and some of the data was obtained without the use of a lockmass compound. However, the data for each of the types of tissue is well clustered in a particular region of the plot, demonstrating that the use of a lockmass compound does not affect the analysis and tissue classification.

It has been determined that more than one different know lock mass compounds may be used without adversely affecting analysis of the sample. Exact lock mass compound(s) may be used and/or external lock mass compound(s) may be used.

Figure 12A:
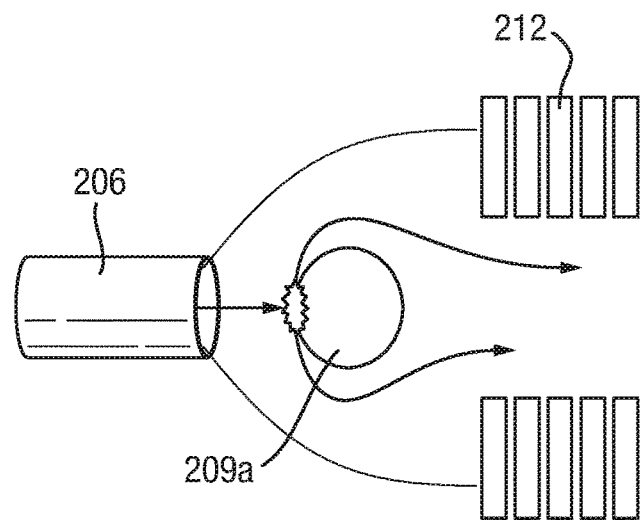
FIG. 12A shows an embodiment wherein the collision surface is spherical and FIG. 12B shows an embodiment wherein the collision surface is coil-shaped.
Figure 12B:
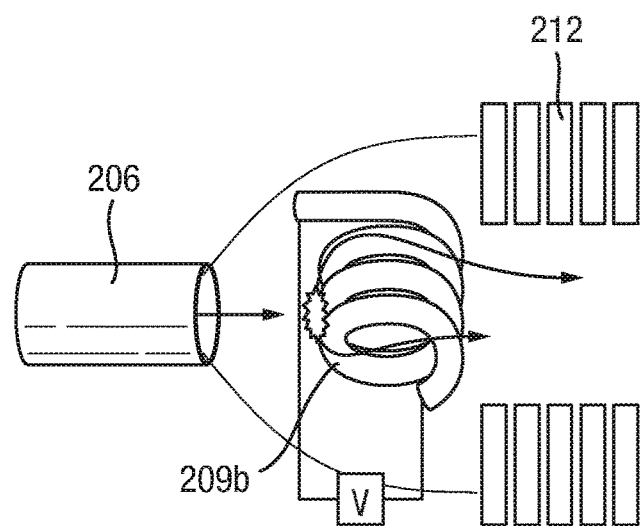
Figure 14A:
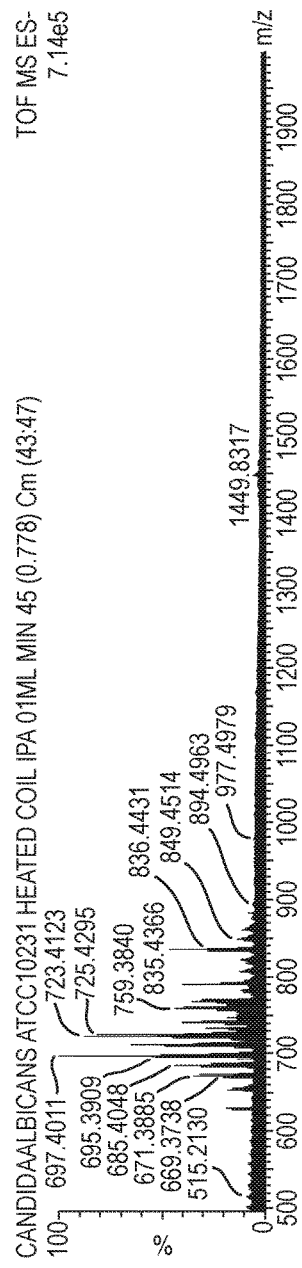
FIG. 14A shows a mass spectrum obtained when analysing a sample wherein an IPA matrix is introduced upstream of a heated collision surface.
Figure 14B:
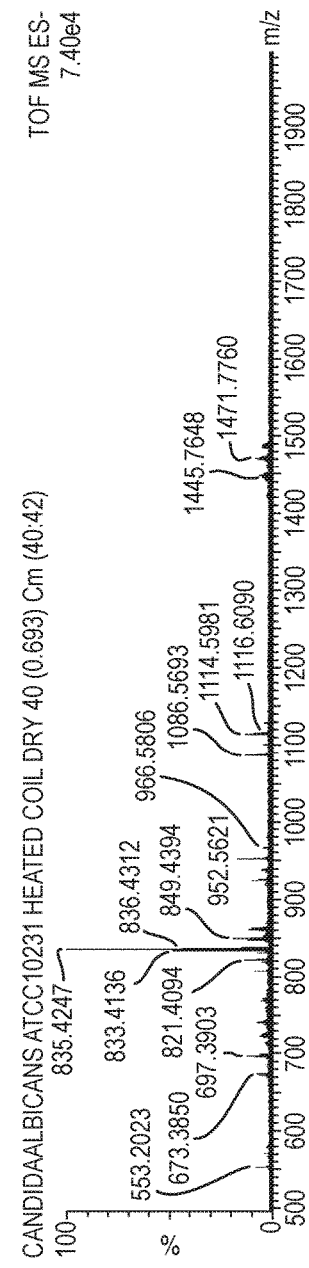
FIG. 14B shows a mass spectrum obtained from the same analysis except when a matrix is not used.
Figure 14C:
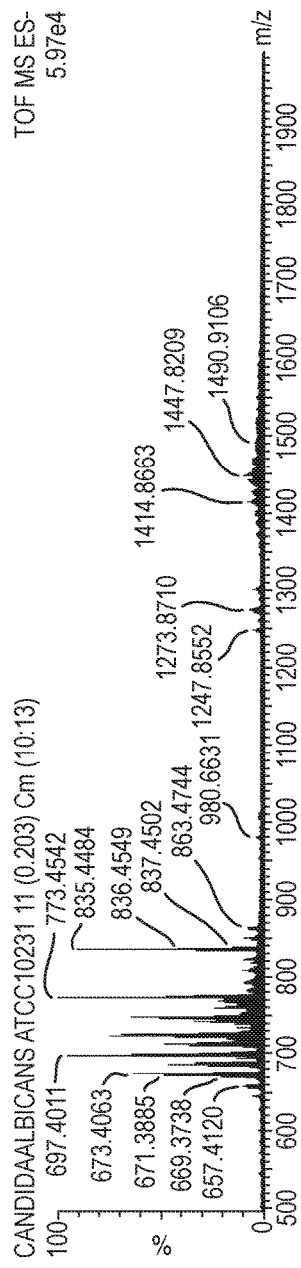
FIG. 14C shows a mass spectrum obtained from the same analysis but when the collision surface is not heated and a matrix is not used.

FIGS. 12A and 11B show schematics of example configurations of the collision surface that may be used in the present invention. FIG. 12A corresponds to the collision surface 209 shown in FIGS. 2 and 3. For example, the collision surface 209 may be a spherical, stainless-steel collision surface 209a and may be mounted approximately 6 mm from the end of the inlet capillary 206 into the analyser 207. FIG. 12B shows an alternative collision surface 209 that may be used, in the form of a coil-shaped collision surface 209b. Ions may be transferred by the ion optics 212 to an analysis region (not shown) of the ion analyser 207. As discussed above, the ion optics 212 may comprise a Step-wave® ion guide.

It is contemplated that the collision surface may be other shapes, such as substantially cylindrical, tubular, rod-shaped, hemispherical, teardrop-shaped, plate-shaped, concave, dish-shaped or conical. It is also contemplated that the collision surface may be formed by the inner surface of a hollow collision assembly having an inlet and an outlet. The aerosol may enter through the inlet and then impact on the inner surface of the collision assembly so as to form or release analyte ions. The analyte ions may then emerge from said collision assembly via said outlet. The inner cross-sectional area of the collision assembly may be either substantially constant or reduce in a direction from the inlet to said outlet, i.e. the collision assembly may be funnel-shaped, tubular or cylindrical. The embodiments relating to a hollow funnel-shaped collision assembly or a hollow cylindrical collision assembly have also been found to result in a high ion yield (or improved ionisation efficiency) coupled with a significant improvement in signal to noise ratio. Furthermore, these embodiments have also been found to result in less contamination of the collision assembly and downstream ion optics by background clusters which are not of analytical interest.

It has been recognised that the REIMS mechanism may lead to substantially equal generation of positively and negatively charged ions, which may subsequently form relatively large molecular clusters of neutral electrical charge. These neutral clusters are not manipulated well by electric fields within the analyser or spectrometer and hence may be eliminated, e.g., by the instrument ion optics 212. The collision surface 209 described herein serves to break up the molecular clusters 205, releasing the ions so that they may be guided by the electrical fields within the analyser or spectrometer. However, it has also been recognised that the provision of the collision surface 209 may induce cross-contamination between measurements of different samples. For example, certain bacterial metabolites were found to induce relatively strong memory effects after only a small number of repetitive measurements, e.g., certain sphingolipids produced by *Bacteroides* spp. or lipopolypeptides such as surfactin and lichenysin produced by certain *Bacillus* spp. This cross-contamination could be mitigated by cleaning the atmospheric pressure interface before each analysis. However, this is undesirable, particularly in automated instruments. In order to avoid contamination of the collision surface 209, the surface may be heated, e.g., to several hundred degrees Celsius. For example, heating the collision surface 209 may cause carbonaceous deposits on the collision surface 209 to react with oxygen introduced through the inlet capillary 206. The carbonaceous deposits will then be converted to $CO_2$ gas, which can leave the collision surface 209 and hence not contaminate the instrument during subsequent analyses. The coil-shaped collision surface 209b of FIG. 12B provides a particularly reproducible heat distribution.

The collision element or surface 209 may be constructed from a material that may be heated by passing an electric current through it, e.g., by applying voltage V in FIG. 12B, enabling it to be easily heated during analysis. For example, the collision surface 209 may be manufactured out of a heat-resistant iron-chromium-aluminium (FeCrAl) alloy such as kanthal. Using such a heated collision surface 209 significantly reduces memory effects and thus the frequency of instrument cleaning may be greatly reduced. For example, thousands of database entries are able to be recorded without any memory effects and even prolonged exposure to lipopolypeptides did not result in any observed carry-over.

The spectral profile obtained using the heated collision surface 209 may, in some cases, be different to the spectral profile obtained using the collision surface 209 unheated, for example, as shown in FIGS. 13A and 13B.

FIGS. 13A and 13B show the spectral profiles resulting from the analysis of *Bacteroides fagilis* using a non-heated collision surface and a heated collision surface, respectively. This indicates that not all spectral constituents are thermally stable enough to be analysed using this type of heated surface technique. For example, the effect of the heated surface seems to be especially strong on phosphatidic acid (which is common in, e.g., fungi such as *C. albicans*) and sphingolipid species (which is common in e.g., *Bacteroidetes phylum*), while it has generally little effect on the spectral appearance observed for phosphatidylglycerol and phosphatidylethanolamines (which are, e.g., the main phospholipid species in *Proteus mirabilis*).

As described above, the introduction of a matrix compound 204, such as isopropyl alcohol (IPA), upstream of the collision surface 209 has been found to improve analyte ionisation and sensitivity of the instrument. It has also been found that the introduction of the matrix compound 204 may restore spectral features that would otherwise be missing by using a heated collision surface rather than a non-heated collision surface. For example, FIGS. 13A and 13B demonstrate that the use of a heated collision surface was found to eliminate spectral features such as ceramides in *Bacteroides fragilis*. The introduction of isopropanol into the sampled aerosol 201 before introduction into the mass analyser 207 or spectrometer was found to restore these spectral features and generate a mass spectral fingerprint similar to that of an atmospheric pressure interface with a non-heated collision surface. Furthermore, the addition of the matrix 204 (e.g., isopropanol) to the sample aerosol 201 led to similar or higher signal intensities as compared to direct aerosol introduction, and thus enables the use of a Venturi pump 213 for aerosol transport.

FIGS. 14A-14C show three mass spectra obtained by analysing a sample of *Candida albicans* (yeast). The mass spectrum of FIG. 14A was obtained whilst introducing an isopropyl alcohol (IPA) matrix upstream of a heated collision surface according to an embodiment. The mass spectrum of FIG. 14B was obtained using the same method as the spectrum of FIG. 14A, except that no isopropyl alcohol (IPA) matrix was introduced. The mass spectrum of FIG. 14C was obtained using the same method as the spectrum of FIG. 14B, except that the collision surface was not heated. FIGS. 14A-14C show the effects of using a heated surface and an isopropanol matrix on the spectral appearance for *Candida albicans* (yeast). These examples show that using a heated collision surface instead of a non-heated collision surface results in significant changes of the spectral appearance, with many spectral features in *Candida albicans* being significantly reduced in relative intensity or disappearing altogether. The introduction of isopropanol into the system having the heated collision surface helps to circumvent this problem and creates a spectrum that is more similar to that obtained using a non-heated collision surface.

As described previously, lockmass compounds (such as Leu Enk) may be used. It is contemplated herein that the intensities of the lockmass compound peaks may be monitored and used to determine if the matrix 204 is flowing at the desired rate, e.g., by introducing the lockmass compound along with the matrix 204. This may be used to determine that the matrix compound 204 is flowing consistently and is not a variable flow.

In order to calibrate the instruments described herein a calibrant may be introduced into the instrument and analysed. For example, the instrument may be calibrated before analysis of the sample (e.g., tissue) and afterwards, to determine if there is any mass shift. The calibrant (e.g., sodium formate) may be injected into the instrument using the matrix (e.g., isopropanol) injection tube 203. However, it was discovered that the optimum distance between the outlet 232 of the matrix injection tube 230 and the inlet 240 of the mass analyser 207 or spectrometer for calibration may be shorter than the optimum distance x for sample analysis, e.g., tissue analysis. In order to address this, different IPA capillary lengths may be used during calibration and tissue analysis. For calibration, a relatively long capillary may be used, whereas for tissue analysis a shorter capillary may be used.

As described above, the matrix introduction conduit may be arranged in various different configurations. For example, the matrix introduction conduit may be coaxial with and arranged inside of the inlet tube to the mass spectrometer. The distance from the exit of the matrix introduction conduit to the downstream exit of the inlet tube to the mass spectrometer (i.e. to the entrance to the vacuum chamber) was found to be important. It is believed that larger distances allow better interaction between the analyte and the matrix.

FIG. 15A shows the total ion current detected as a function of time for several different distances between the exit of the matrix introduction conduit and the entrance to the mass spectrometer vacuum chamber. Positive distances represent a distance in the direction downstream of the entrance to the mass spectrometer vacuum chamber, whereas negative distances represent the distance upstream of the entrance to the mass spectrometer vacuum chamber. The sample analysed was porcine liver and the matrix was isopropyl alcohol. The matrix capillary was made from quartz glass, had an outer diameter of 360 μm and an inner diameter of 250 μm. A relatively strong background noise and strong IPA signal was observed when the exit of the matrix introduction conduit was arranged upstream of the entrance to the mass spectrometer vacuum chamber (i.e. at negative distances).

FIGS. 15B-15F show the mass spectra obtained at the different distances of FIG. 15A. FIGS. 15B-15F show mass spectra obtained at distances of −10 mm, −20 mm, −24 mm, 0 mm and +2 mm respectively. It can be seen that when the exit of the matrix introduction tube was arranged at or downstream of the entrance to the vacuum chamber (i.e. distances of 0 mm and +2 mm), the effect of the matrix was relatively low. In contrast, the further the exit of the matrix introduction tube was arranged upstream of the entrance to the vacuum chamber (i.e. more negative distances), the more influence the matrix had. It was confirmed that at a distance of 0 mm, increasing the matrix flow rate did not improve the total ion current observed.

FIG. 16A shows data corresponding to that of FIG. 15A, except wherein the data was obtained using a matrix introduction conduit having an inner diameter of 100 μm and wherein different distances to FIG. 15A were used. As with FIG. 15A, the ion signal observed increased the more that the exit of the matrix introduction tube was arranged upstream of the entrance to the vacuum chamber (i.e. the more negative the distance was).

FIG. 16B shows the mass spectra obtained at the different distances of FIG. 16A. FIGS. 16B-16F show mass spectra obtained at distances of 0 mm, +2 mm, −1 mm, −10 mm, −20 mm, −30 mm, −40 mm and −50 mm respectively. It can be seen that when the exit of the matrix introduction tube was arranged at or downstream of the entrance to the vacuum chamber (i.e. distances of 0 mm and 2 mm), there the effect of the matrix was relatively low. In contrast, the further the exit of the matrix introduction tube was arranged upstream of the entrance to the vacuum chamber (i.e. more negative distances), the more influence the matrix had. The spectra are also less noisy than the spectra of FIGS. 15B-15F and the matrix had a stronger effect. It was confirmed that at a distance of 0 mm, increasing the matrix flow rate did not improve the spectra.

Figure 15A:
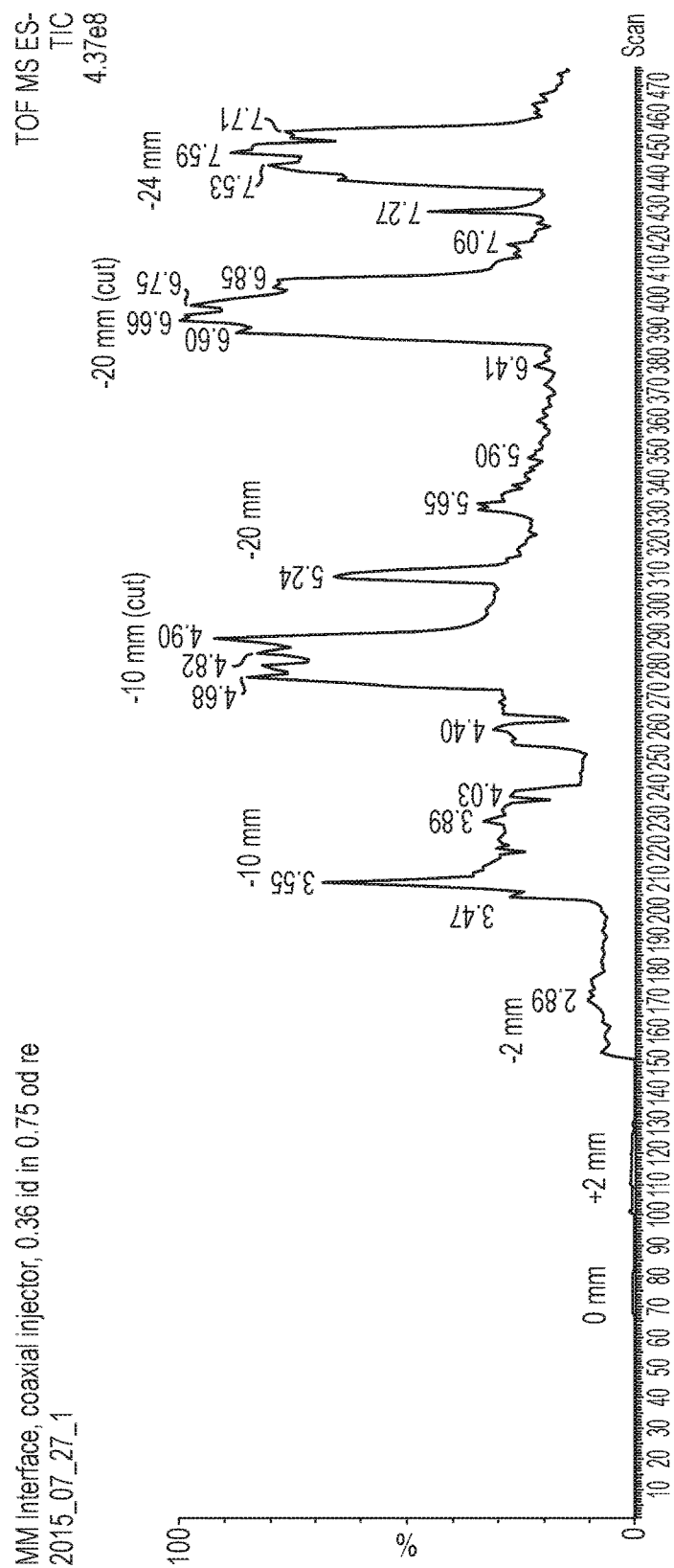
FIG. 15A shows the total ion current detected for several different distances between the exit of a matrix introduction conduit having an inner diameter of 250 μm and the entrance to the mass spectrometer vacuum chamber.
Figure 15B:
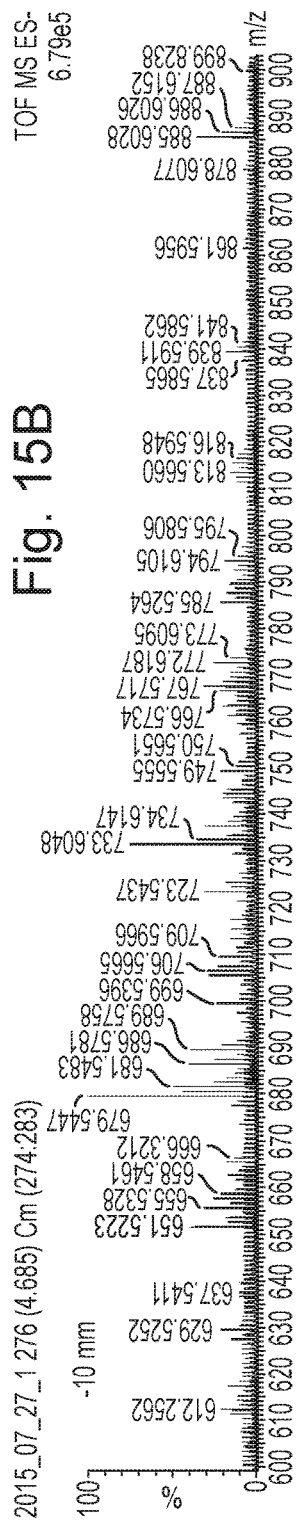
FIGS. 15B-15F show the mass spectra obtained at the different distances of FIG. 15A.
Figure 15C:
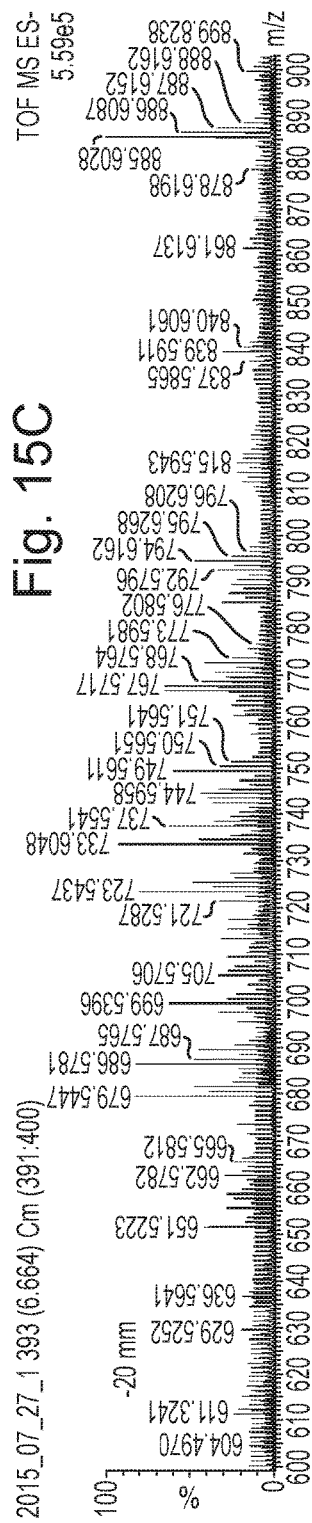
Figure 15D:
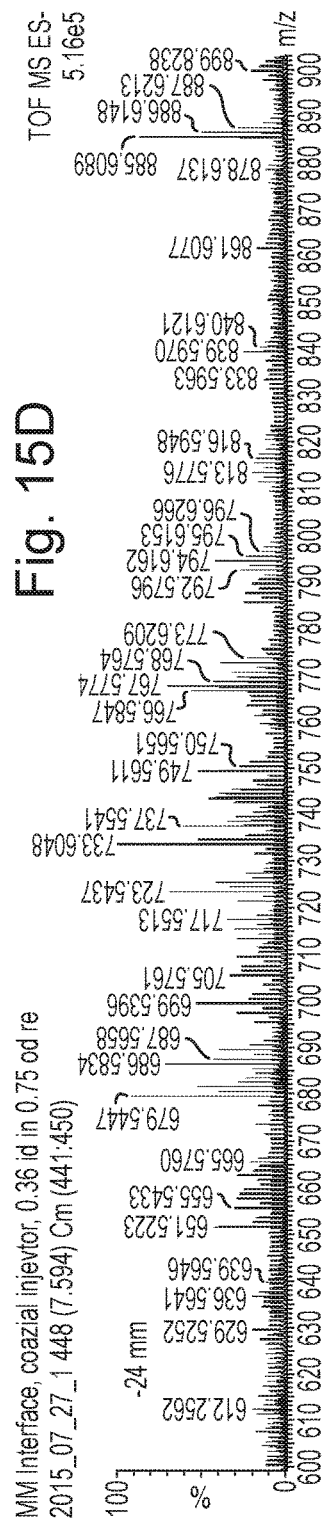
Figure 15E:
Figure 15F:
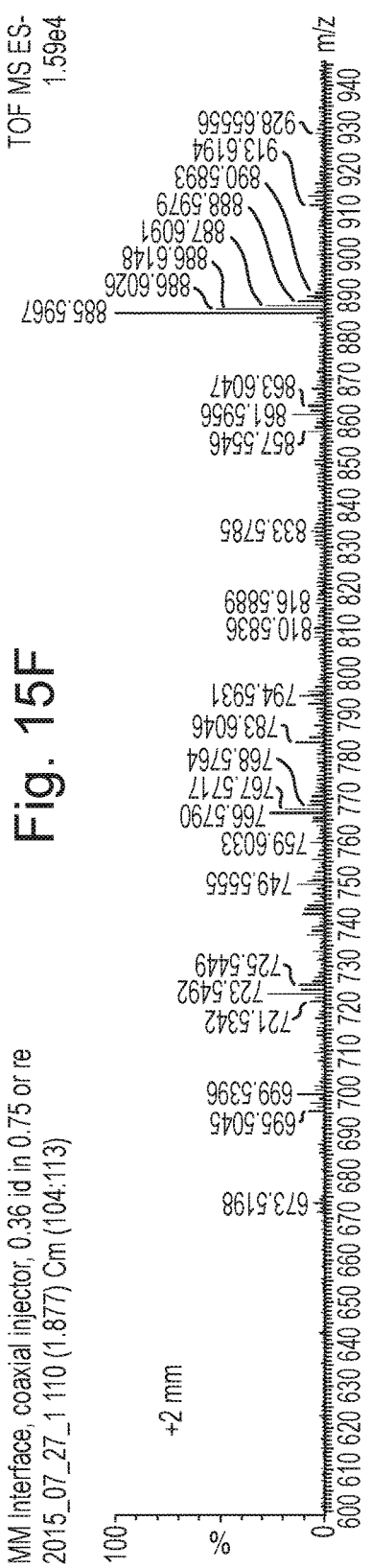
Figure 16A:
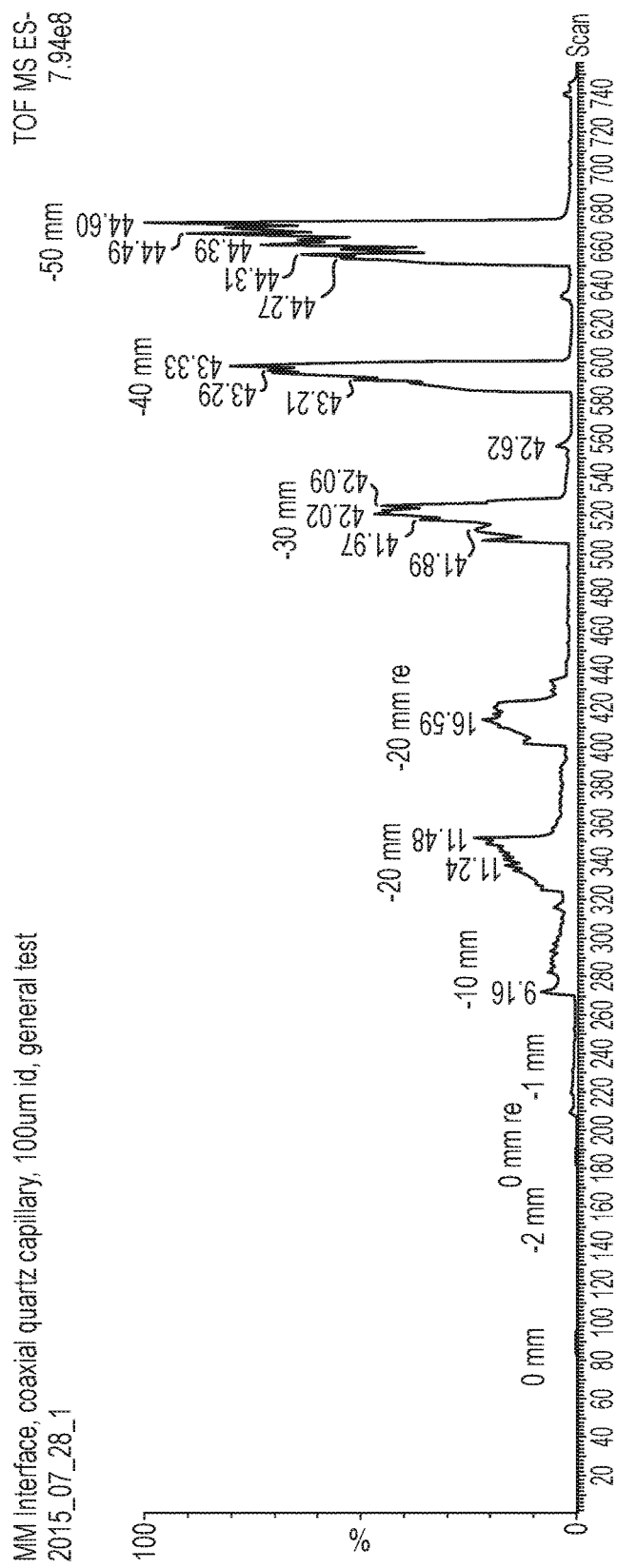
FIG. 16A shows the total ion current detected for several different distances between the exit of a matrix introduction conduit having an inner diameter of 100 μm and the entrance to the mass spectrometer vacuum chamber.
Figure 16E:
Figure 16F:
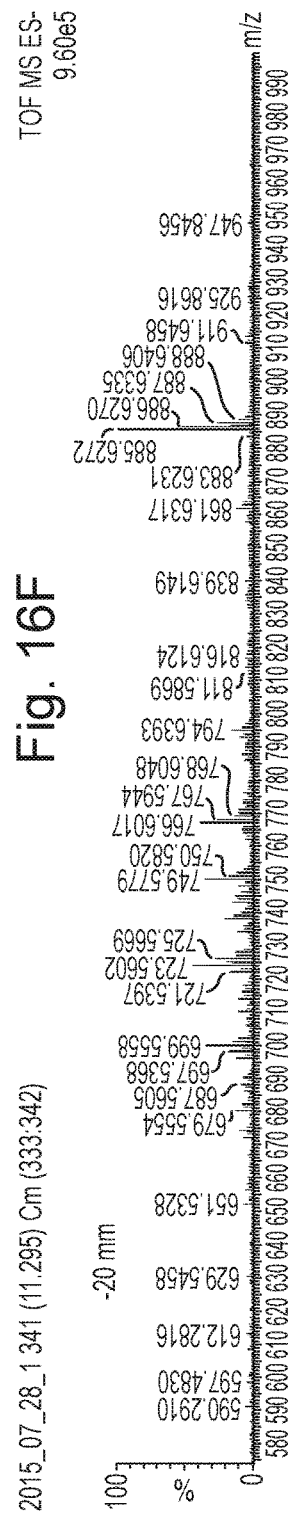
Figure 16G:
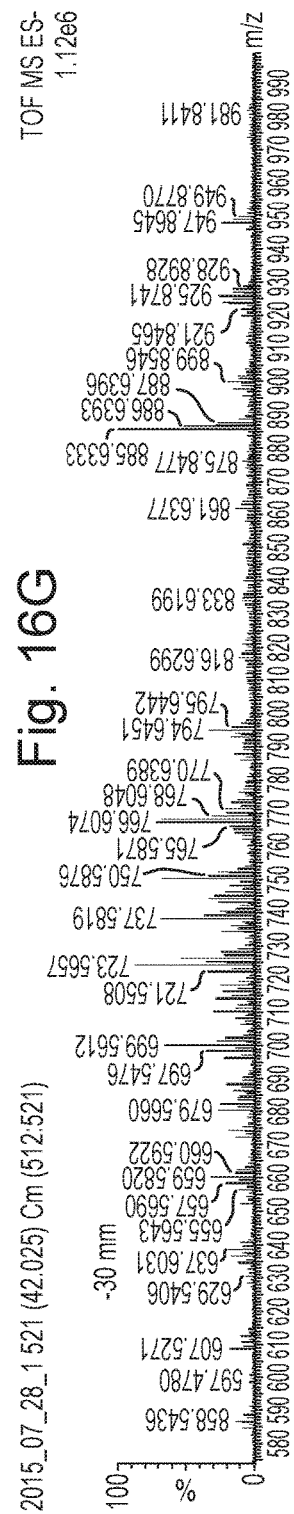
Figure 16H:
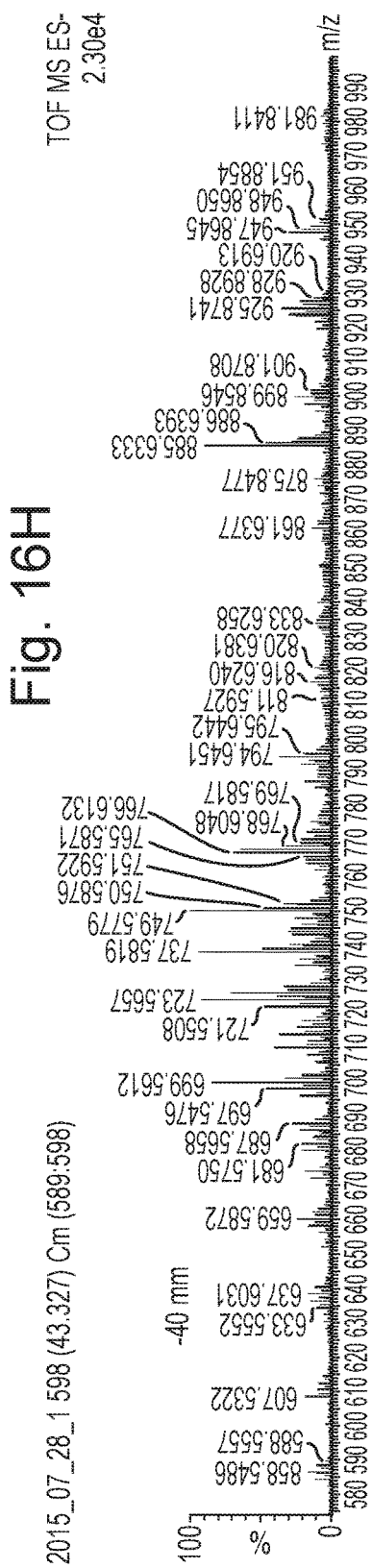
Figure 16I:
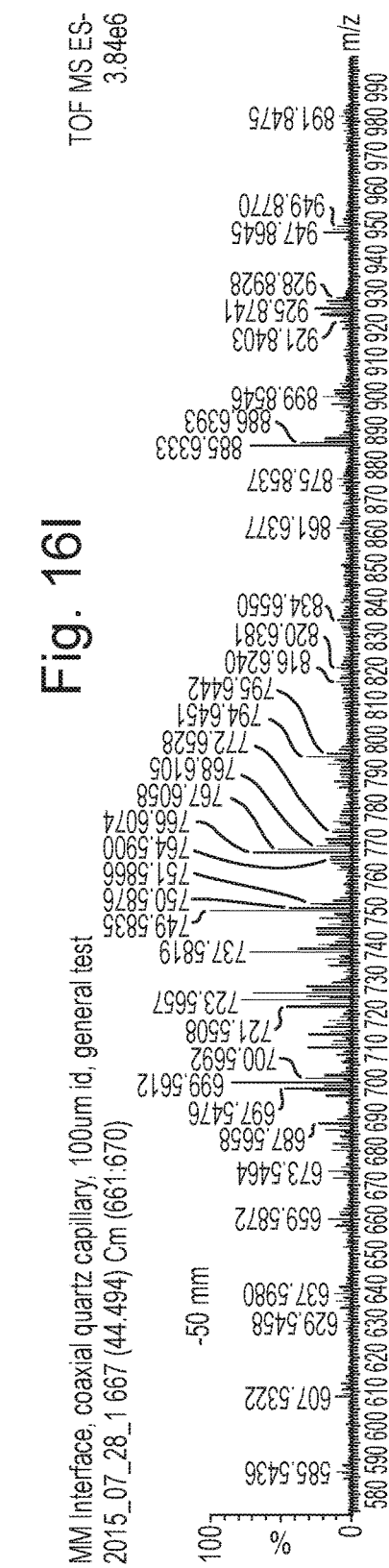
Figure 17A:
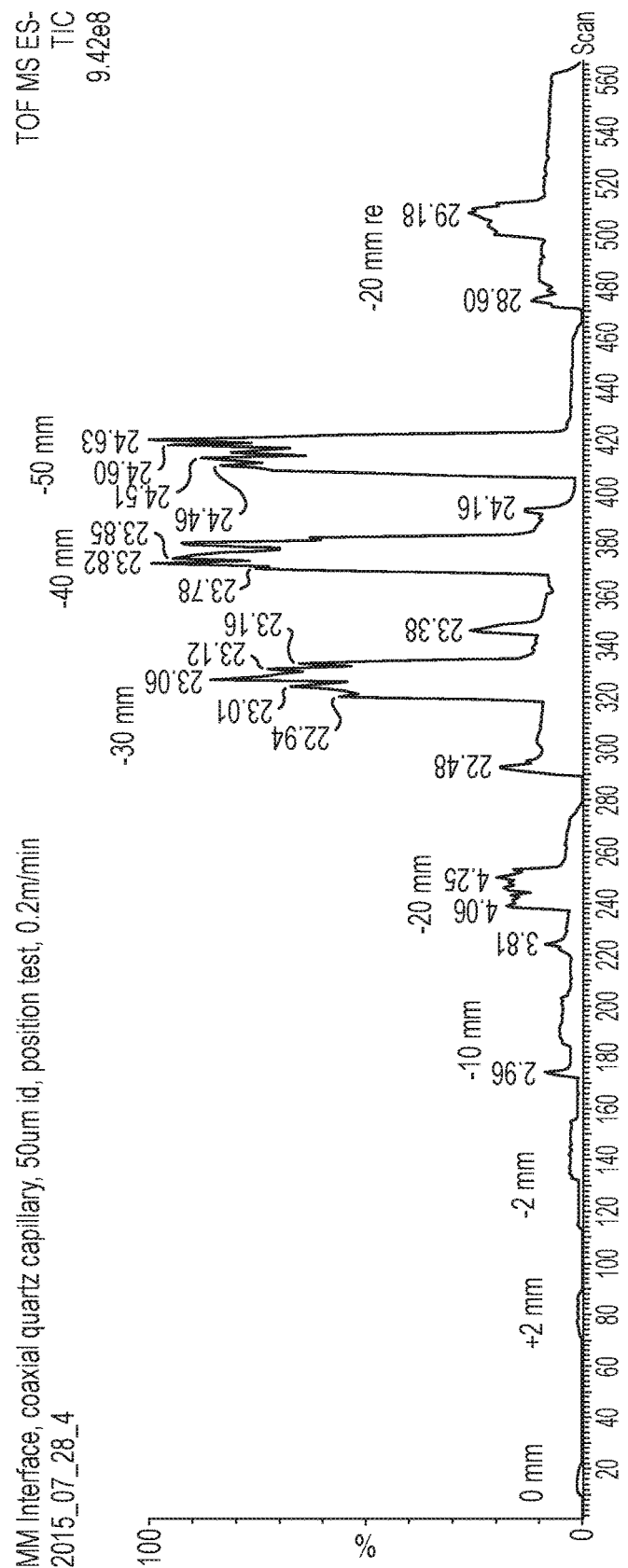
FIG. 17A shows the total ion current detected for several different distances between the exit of a matrix introduction conduit having an inner diameter of 50 μm and the entrance to the mass spectrometer vacuum chamber.
Figure 17E:
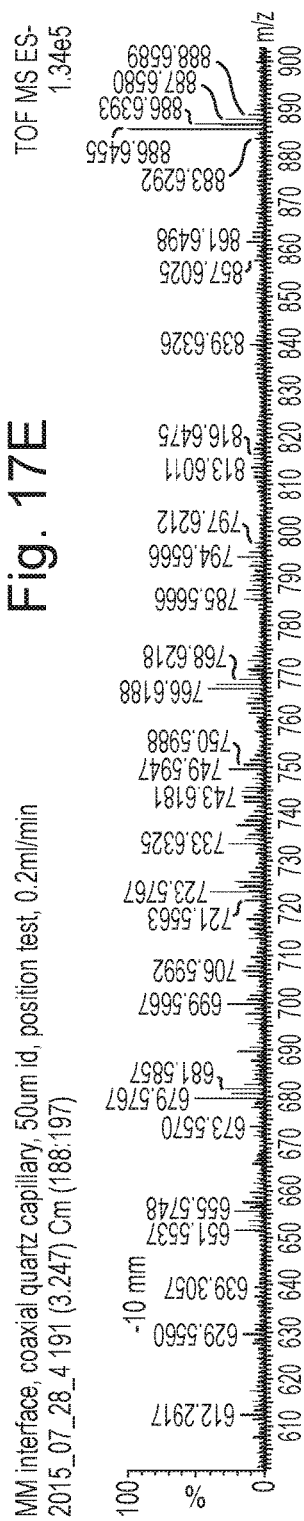
Figure 17F:
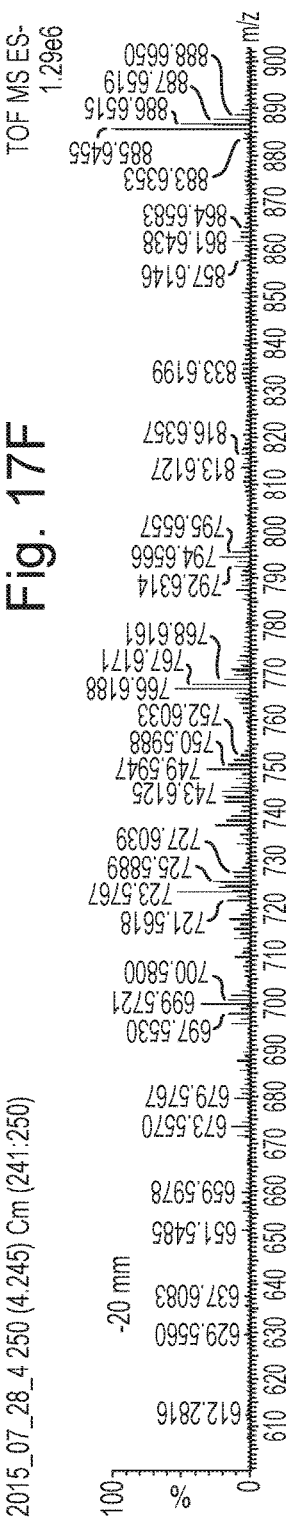
Figure 17G:
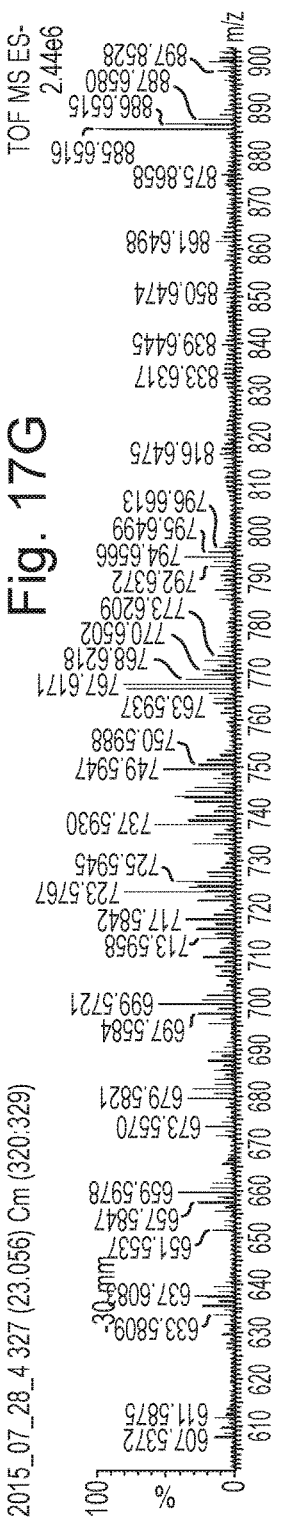
Figure 17H:
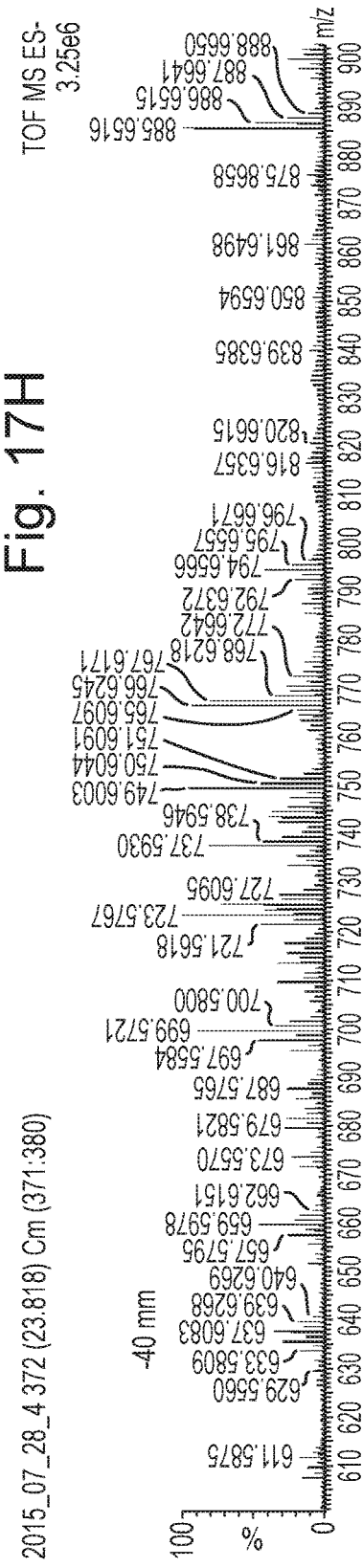
Figure 17I:
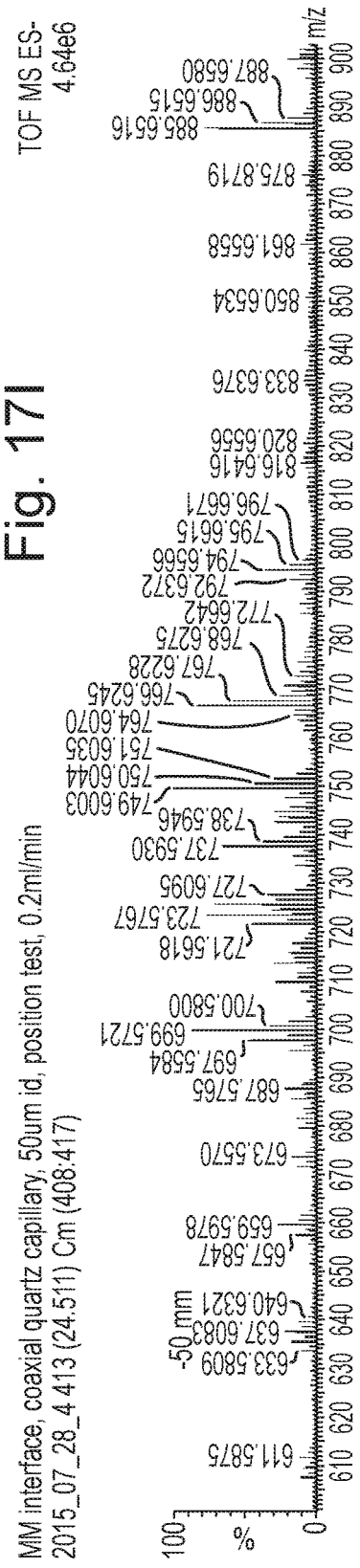

FIG. 17A shows data corresponding to that of FIG. 15A, except wherein the data was obtained using a matrix introduction conduit having an inner diameter of 50 µm and wherein different distances to FIG. 15A were used. As with FIG. 15A, the ion signal observed in FIG. 17A increased the more that the exit of the matrix introduction tube was arranged upstream of the entrance to the vacuum chamber (i.e. the more negative the distance was).

FIGS. 17B-17I B show the mass spectra obtained at the different distances of FIG. 17A. FIGS. 17B-17F show mass spectra obtained at distances of 0 mm, +2 mm, −2 mm, −10 mm, −20 mm, −30 mm, −40 mm and −50 mm respectively. It can be seen that when the exit of the matrix introduction tube was arranged at or downstream of the entrance to the vacuum chamber (i.e. distances of 0 mm and 2 mm), the effect of the matrix was minimal. In contrast, the further the exit of the matrix introduction tube was arranged upstream of the entrance to the vacuum chamber (i.e. more negative distances), the more influence the matrix had.

It has been found that the position of the matrix conduit affects the ion signal more than the flow rate of the matrix.

Figure 18A:
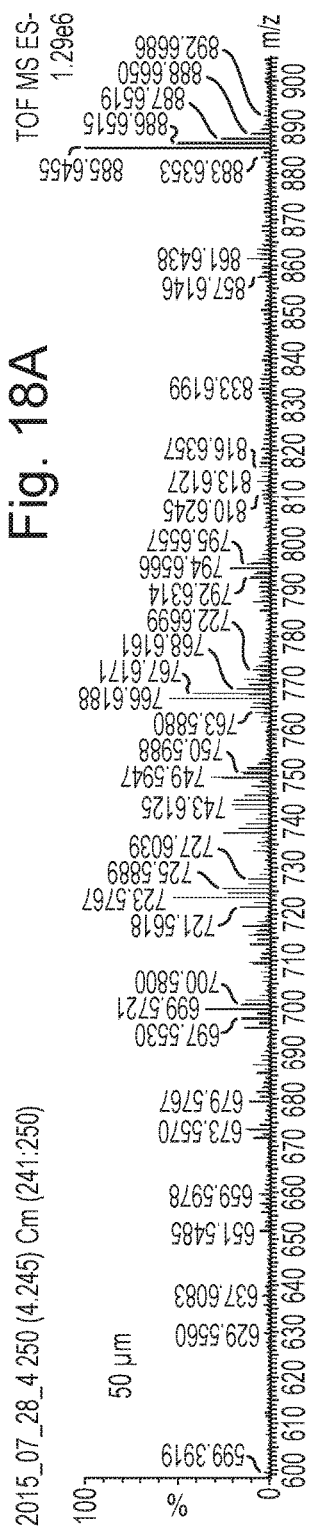
FIGS. 18A-18C show three spectra obtained for matrix introduction conduits having internal diameters of 50 μm, 100 μm and 250 μm, respectively.
Figure 18B:
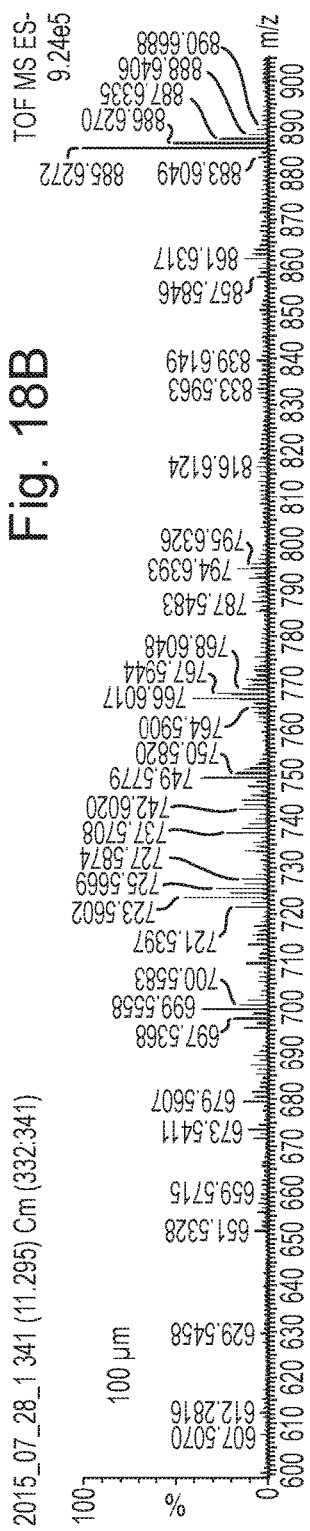
Figure 18C:
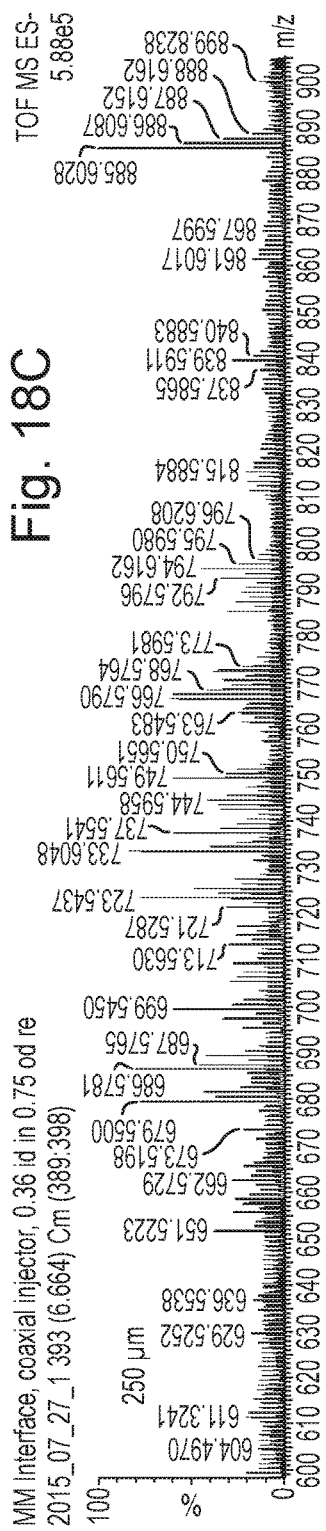

FIGS. 18A-18C show three spectra obtained for matrix introduction conduits having internal diameters of 50 µm, 100 µm and 250 µm, respectively, when the exit of each conduit was arranged 20 mm upstream of the entrance to the vacuum chamber and using a matrix flow rate of 0.2 ml/min. The spectra show that the smaller the inner diameter of the matrix introduction conduit, the better and less noisy the spectra are.

It has also been found that tapering the exit end of the matrix introduction conduit improves the ion signal intensity detected.

As described above, e.g., in relation to FIG. 5B, a whistle arrangement may be used for sampling. In this arrangement the matrix introduction conduit may be coaxial with the inlet tube to the mass spectrometer. As described above, the distance x from the exit of the matrix introduction conduit to the entrance of the inlet tube to the mass spectrometer was found to be important.

Figure 19A:
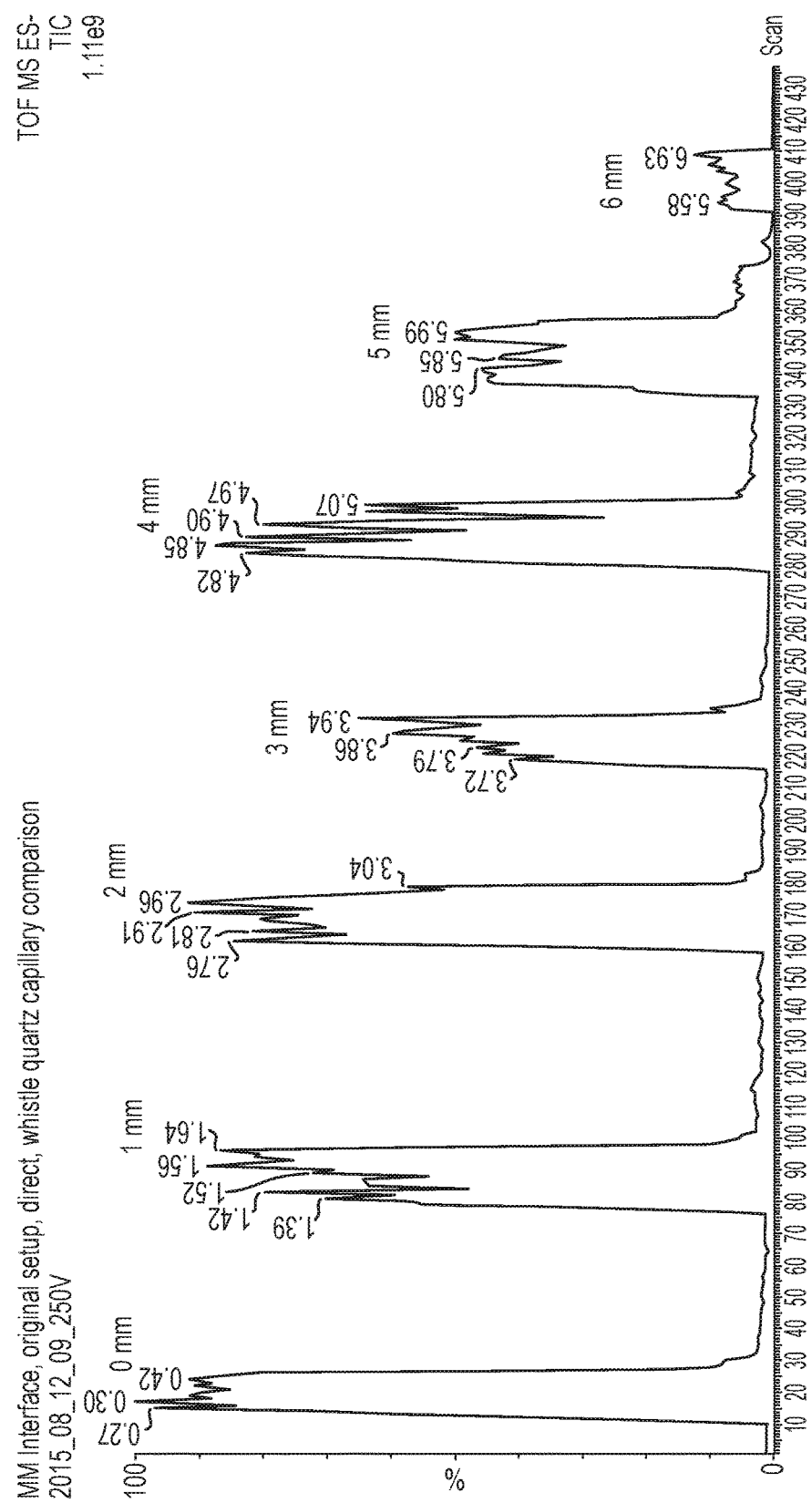
FIG. 19A shows the total ion current detected for several different distances between the exit of a matrix introduction conduit having an inner diameter of 250 μm and the coaxial entrance to the mass spectrometer inlet tube.
Figure 19B:
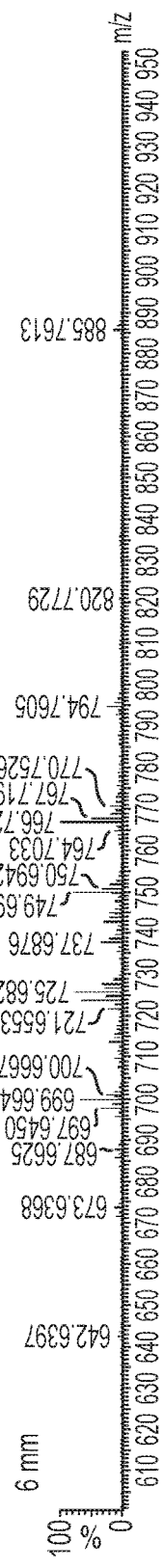
FIGS. 19B-19H show the mass spectra obtained at the different distances of FIG. 19A.
Figure 19C:
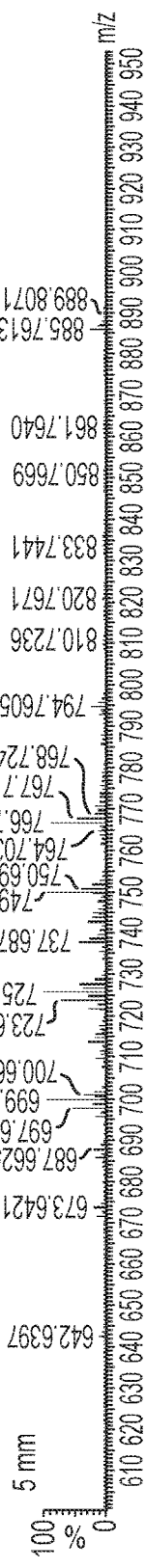
Figure 19D:
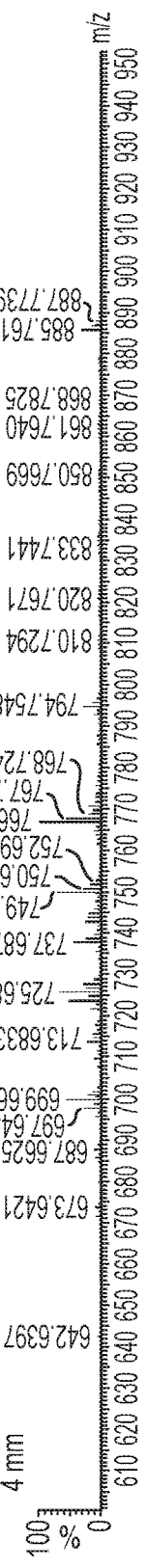
Figure 19E:
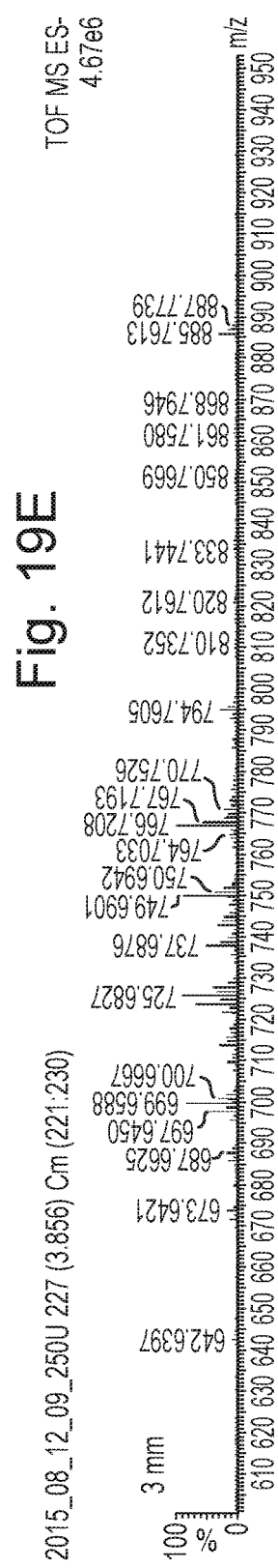
Figure 19F:
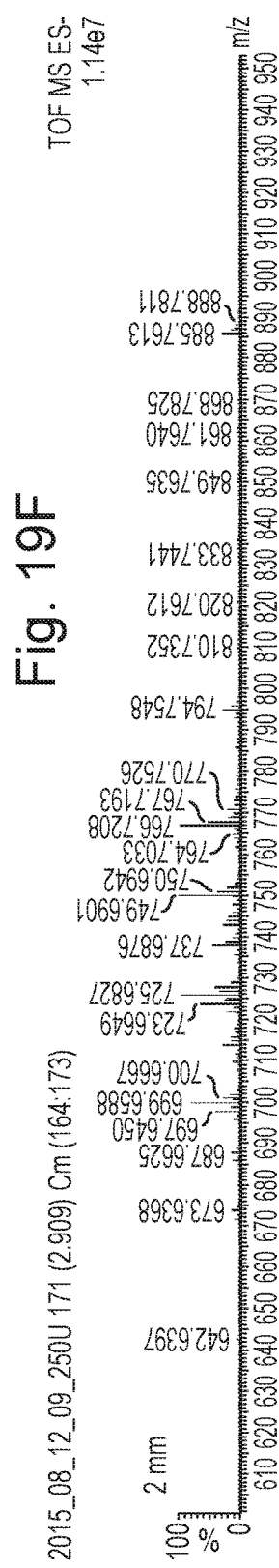
Figure 19G:
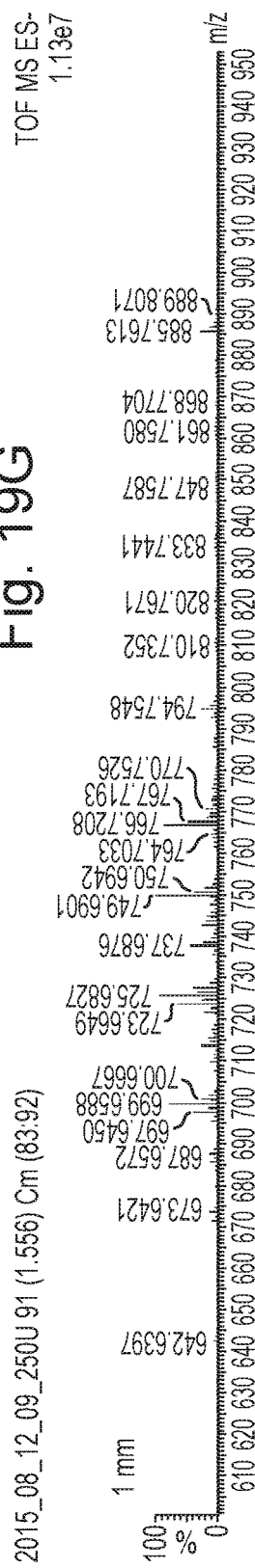
Figure 19H:
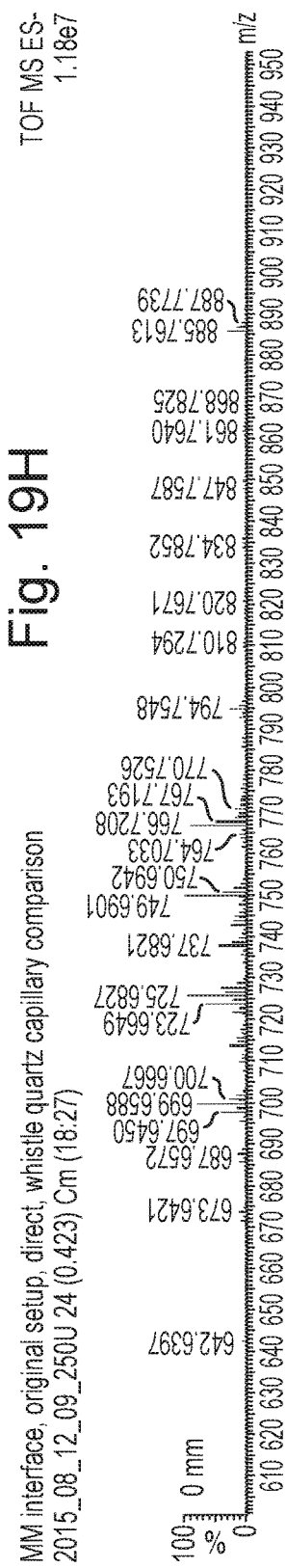

FIG. 19A shows the total ion current detected as a function of time for several different distances between the exit of the matrix introduction conduit and the entrance to the mass spectrometer inlet tube, in the whistle arrangement. The sample analysed was porcine liver and the matrix was isopropyl alcohol. The matrix capillary was made from quartz glass, had an outer diameter of 360 µm and an inner diameter of 250 µm. It can be seen that the ion signal intensity was approximately the same for different distances between the matrix conduit outlet and the mass spectrometer tube inlet, until a distance of around 3-4 mm.

FIGS. 19B to 19H show the mass spectra obtained at the different distances of FIG. 19A. FIGS. 19B-19F show mass spectra obtained at distances of 6 mm, 5 mm, 4 mm, 3 mm, 2 mm, 1 mm and 0 mm respectively. It can be seen that the spectra are very similar at distances up to around 3 mm.

Figure 20A:
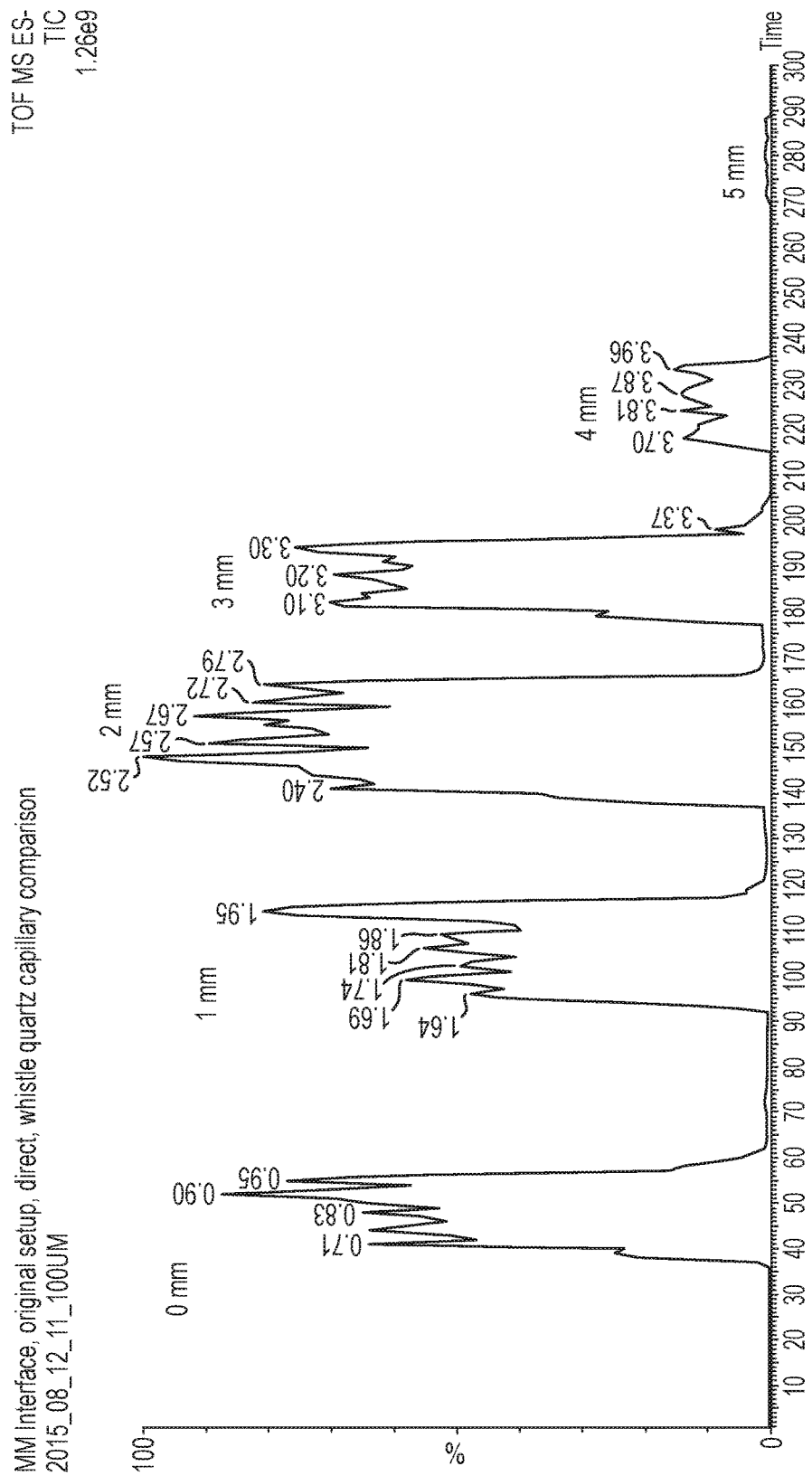
FIG. 20A shows the total ion current detected for several different distances between the exit of a matrix introduction conduit having an inner diameter of 100 μm and the coaxial entrance to the mass spectrometer inlet tube.
Figure 20E:
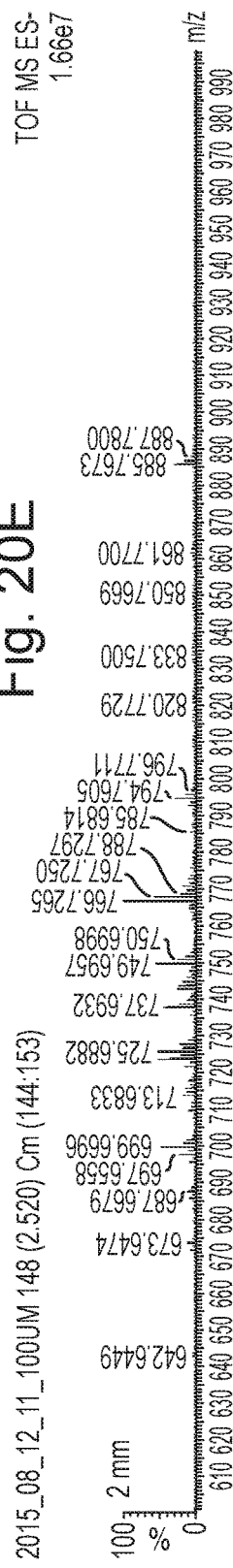
Figure 20F:
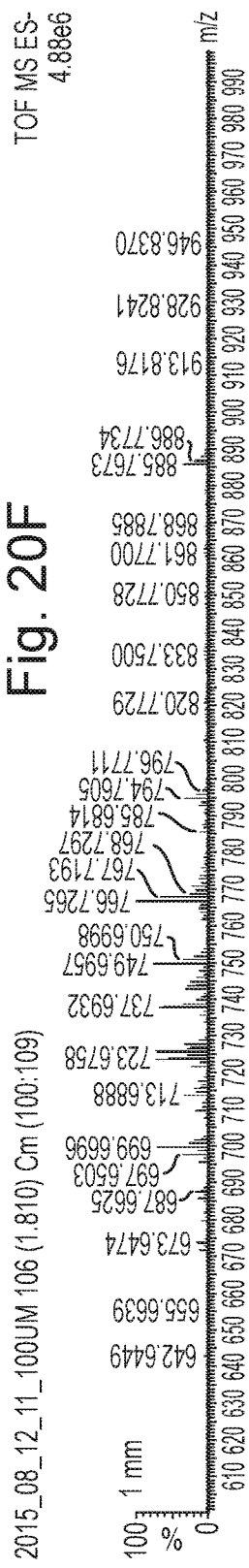
Figure 20G:
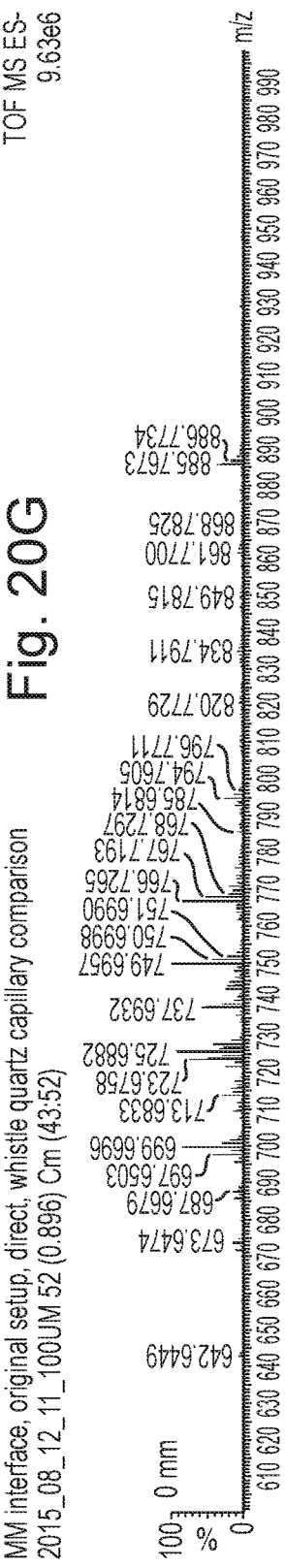

FIG. 20A shows data corresponding to that of FIG. 19A, except wherein the data was obtained using a matrix introduction conduit having an inner diameter of 100 µm. It can be seen that the ion signal intensity is approximately the same for different distances between the matrix conduit outlet and the mass spectrometer tube inlet, until a distance of around 3 mm (although most intense at a distance of around 2 mm). At distances greater than 3 mm the ion signal intensity dropped.

FIGS. 20B to 20G show the mass spectra obtained at the different distances of FIG. 20A. FIGS. 20B-20G show mass spectra obtained at distances of 5 mm, 4 mm, 3 mm, 2 mm, 1 mm and 0 mm respectively.

Figure 21A:
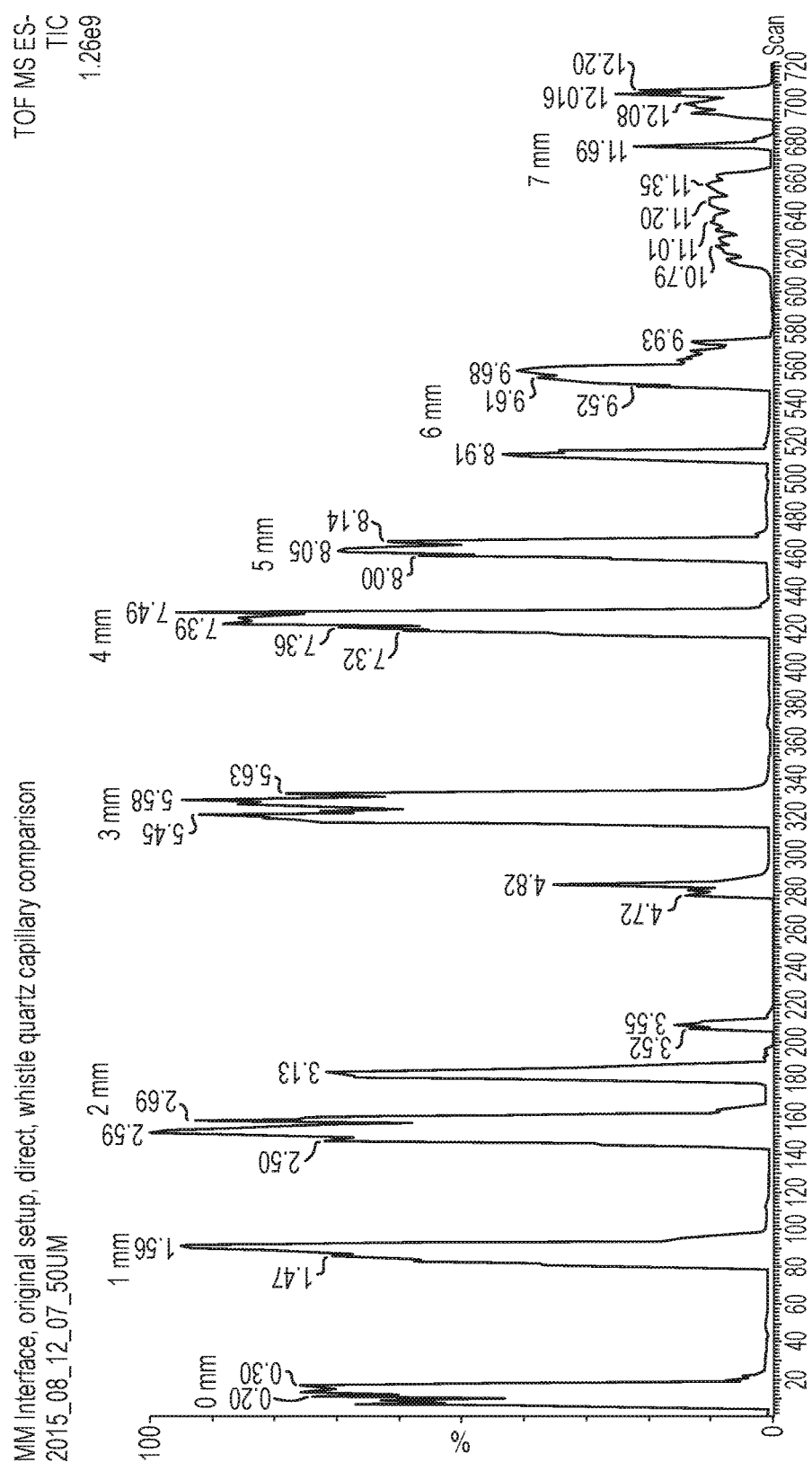
FIG. 21 shows the total ion current detected for several different distances between the exit of a matrix introduction conduit having an inner diameter of 50 μm and the coaxial entrance to the mass spectrometer inlet tube.
FIGS. 21B-21I show the mass spectra obtained at the different distances of FIG. 21A.
Figure 21B:
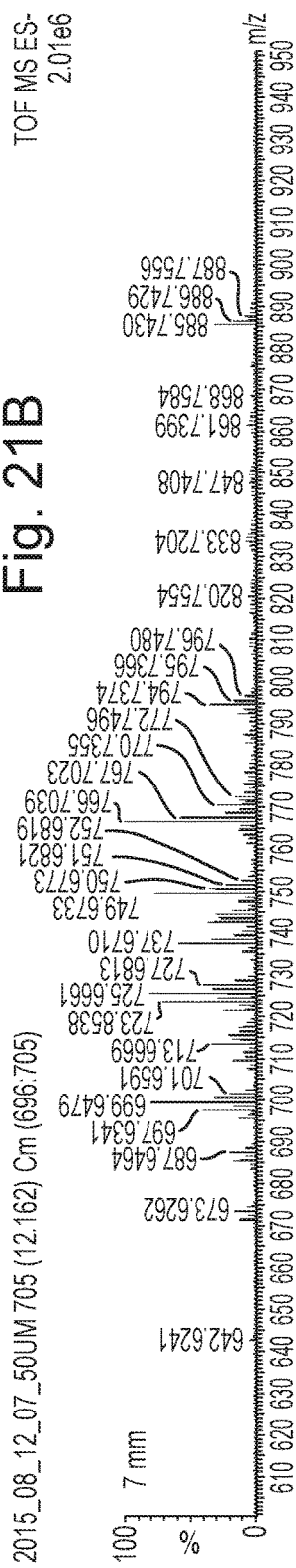
Figure 21C:
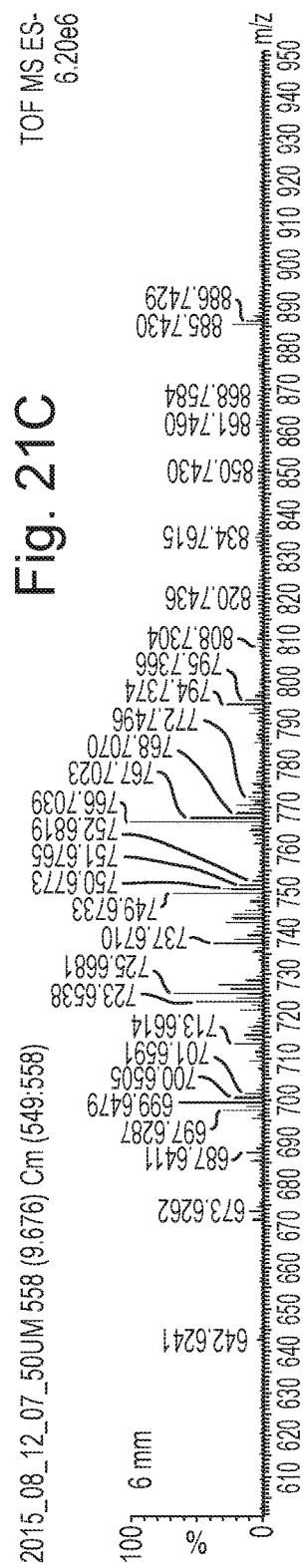
Figure 21D:
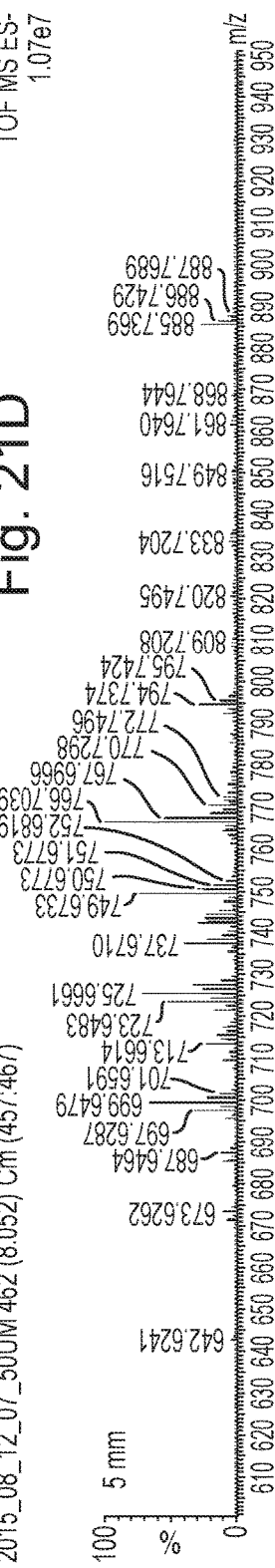
Figure 21E:
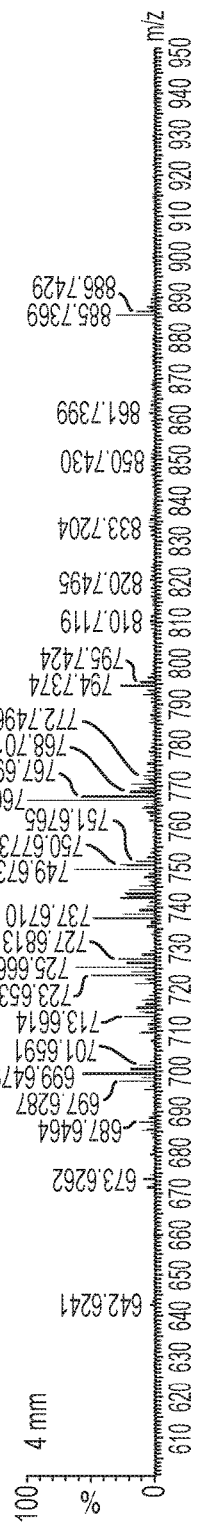
Figure 21F:
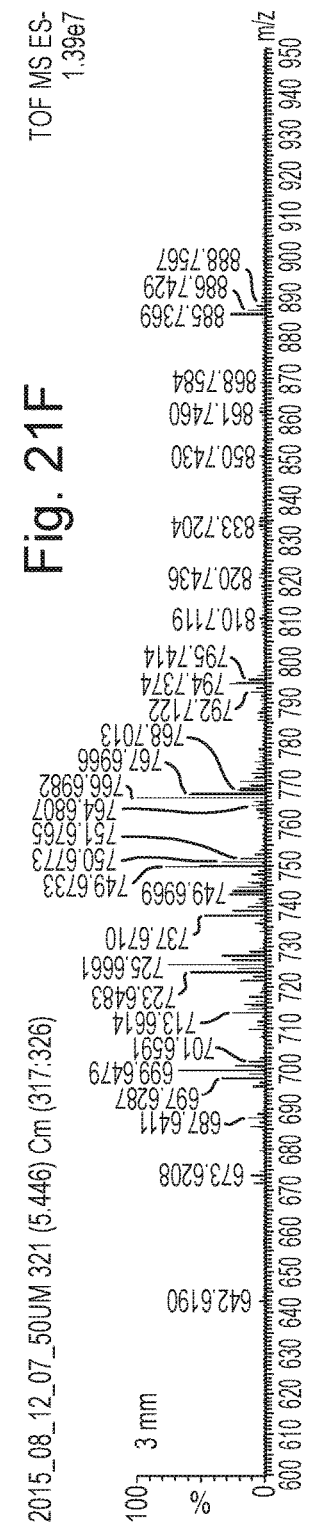
Figure 21G:
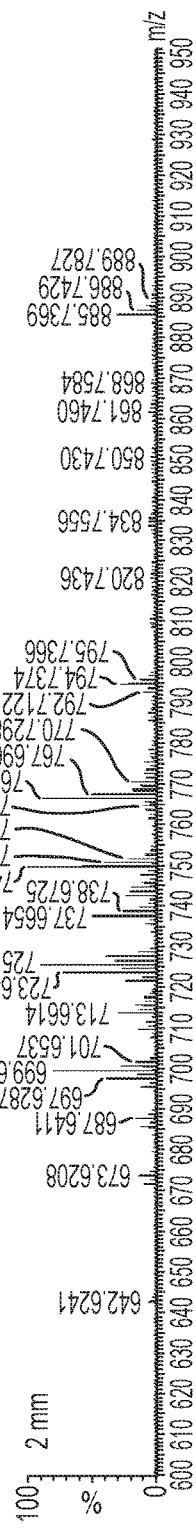
Figure 21H:
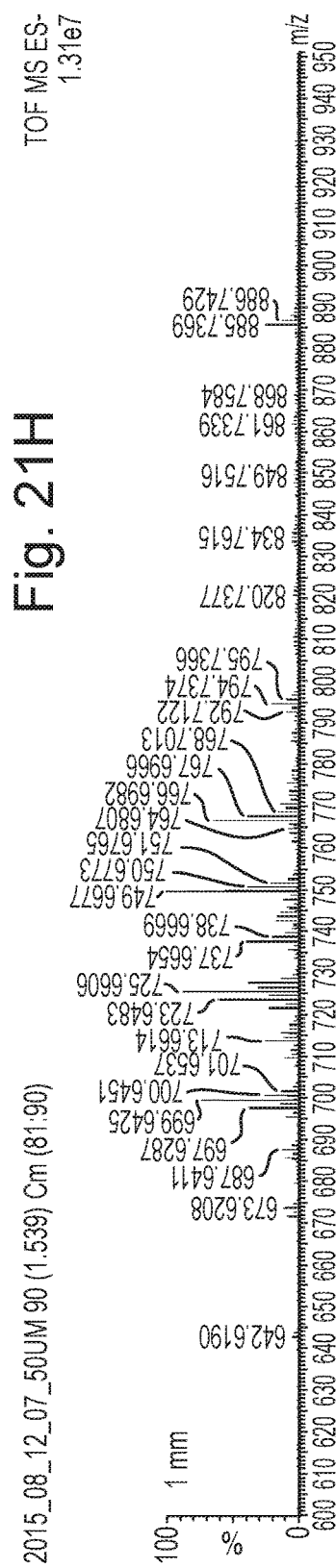
Figure 21I:
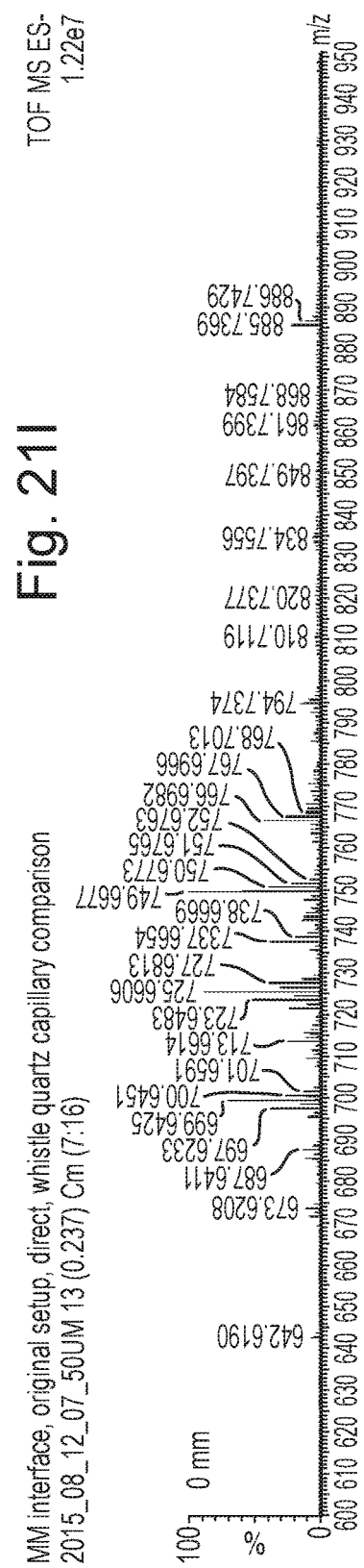

FIG. 21A shows data corresponding to that of FIG. 19A, except wherein the data was obtained using a matrix introduction conduit having an inner diameter of 50 µm and wherein data for additional distances are shown. It can be seen that the ion signal intensity is approximately the same for different distances between the matrix conduit outlet and the mass spectrometer tube inlet, until a distance of around 4 mm. At distances greater than 4 mm the ion signal intensity dropped.

FIGS. 21B to 21I show the mass spectra obtained at the different distances of FIG. 21A. FIGS. 21B-21I show mass spectra obtained at distances of 7 mm, 6 mm, 5 mm, 4 mm, 3 mm, 2 mm, 1 mm and 0 mm respectively.

Various biological samples were analysed using the methods and techniques according to the various embodiments of the present invention. These analyses demonstrated that the use of a collision surface and/or matrix improved the ion signal obtained from the analyte.

FIGS. 22A-22C each show a mass spectrum obtained using a REIMS technique in negative ion mode for the analysis of lamb liver. Each spectrum represents data obtained from five samples. The spectrum of FIG. 22A was obtained without the introduction of a matrix into the analyte stream and without the use of a collision surface. The spectrum of FIG. 22B was obtained with the introduction of a matrix (isopropyl alcohol at a rate of 0.2 mL/min) into the analyte stream and without the use of a collision surface. The spectrum of FIG. 22C was obtained with the introduction of a matrix (isopropyl alcohol at a rate of 0.2 mL/min) into the analyte stream and with the use of a collision surface. It can be seen by comparing these spectra that the use of a matrix increases analyte ion signal intensities, even without the use of a collision surface, and that the combined use of a matrix and collision surface significantly increases the intensity of analyte ion signals.

Figure 23A:
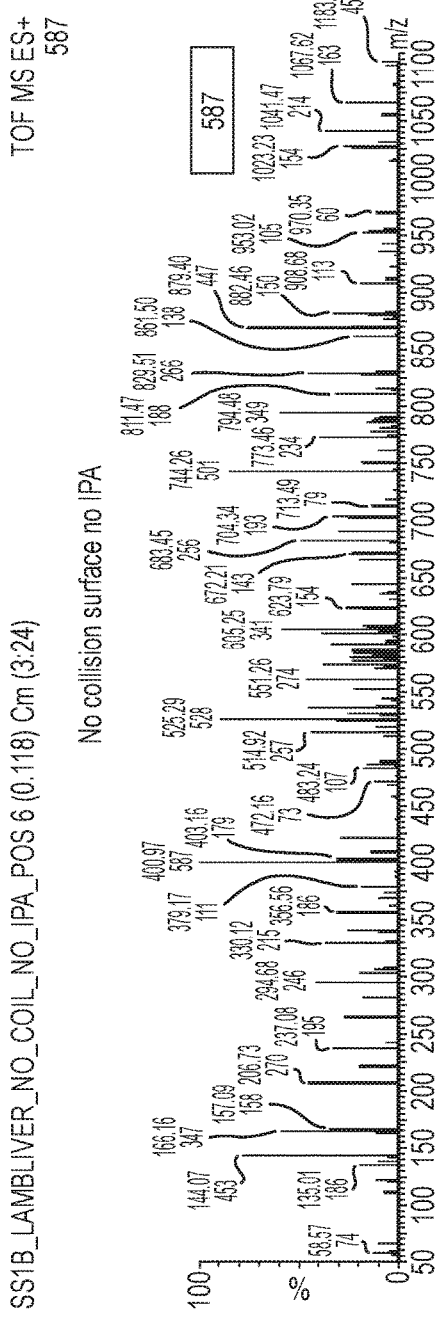
FIG. 23A shows a mass spectrum obtained in positive ion mode without the introduction of a matrix into the analyte stream and without the use of a collision surface.
Figure 23B:
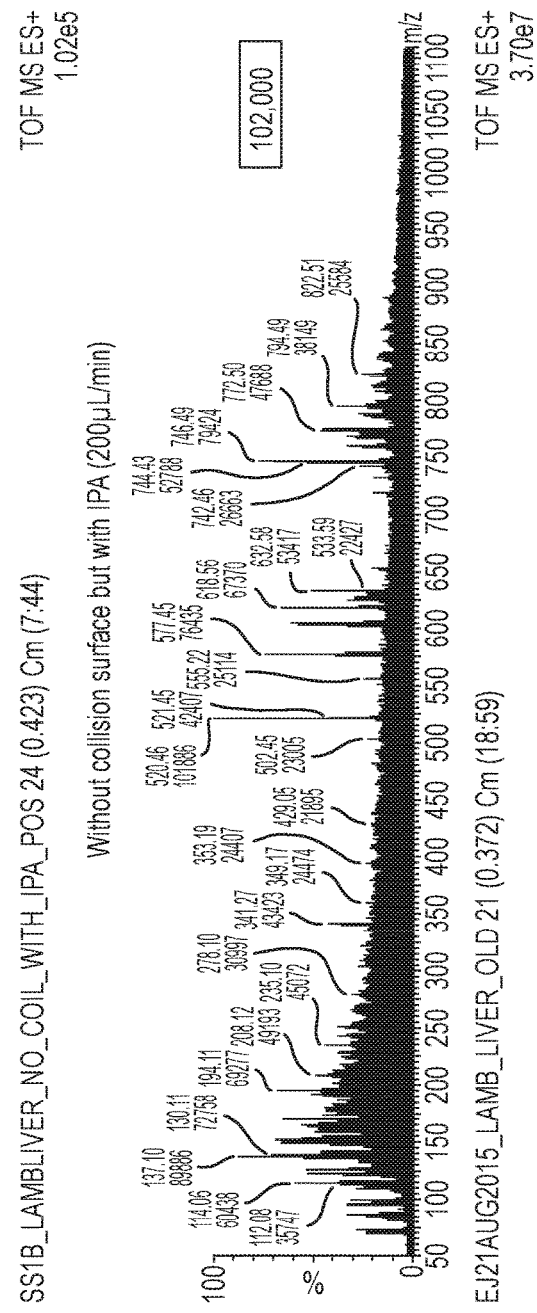
Figure 23C:
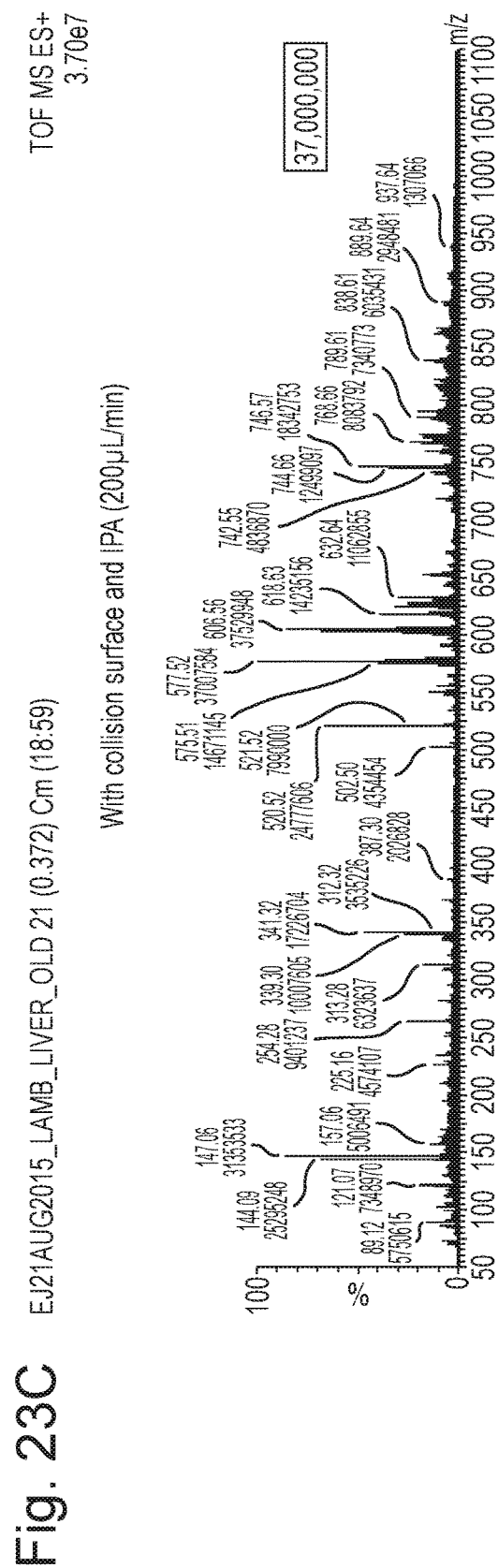

FIGS. 23A-23C each show a mass spectrum obtained using a REIMS technique in positive ion mode for the analysis of lamb liver. Each spectrum represents data obtained from five samples. The spectrum of FIG. 23A was obtained without the introduction of a matrix into the analyte stream and without the use of a collision surface. The spectrum of FIG. 23B was obtained with the introduction of a matrix (isopropyl alcohol at a rate of 0.2 mL/min) into the analyte stream and without the use of a collision surface. The spectrum of FIG. 23C was obtained with the introduction of a matrix (isopropyl alcohol at a rate of 0.2 mL/min) into the analyte stream and with the use of a collision surface. As with the negative ion mode shown in FIGS. 22A-22C, it can be seen by comparing the positive ion mode spectra of FIGS. 23A-23C that the use of a matrix increases analyte ion signal intensities, even without the use of a collision surface, and that the combined use of a matrix and collision surface significantly increases the intensity of analyte ion signals.

It was also discovered that the analysis of highly adipose tissues, such as normal breast tissue, may generate little of no ion signal without the use of a matrix.

Figures 24A, 24B:
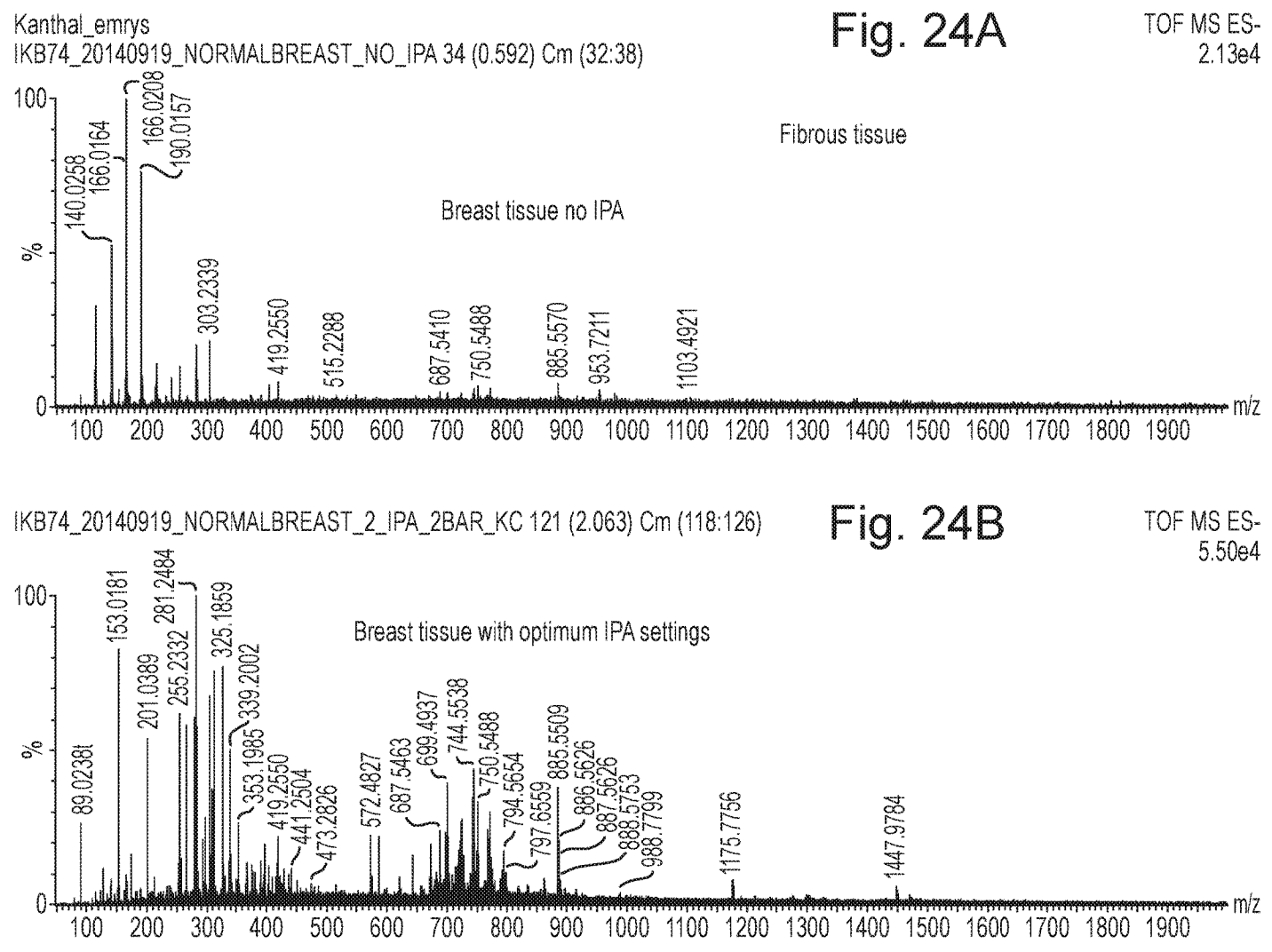

FIG. 24A shows a mass spectrum obtained from the analysis of normal breast tissue without the use of a matrix. FIG. 24B shows a mass spectrum obtained from the analysis of normal breast tissue with the use of isopropyl alcohol as a matrix. It can be seen by comparing these spectra that the use of a matrix significantly improves the signal intensity for analyte ions.

Analysing Sample Spectra

A list of analysis techniques which are intended to fall within the scope of the present invention are given in the following table:

| Analysis Techniques |
|---|
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matrix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 25:
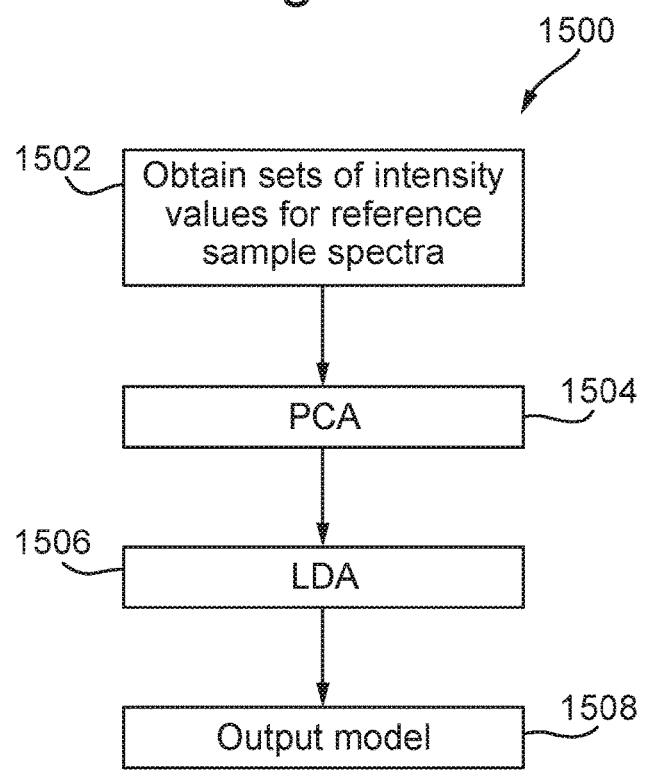
FIG. 25 shows a method of analysis that comprises building a classification model according to various embodiments.

FIG. 25 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 26:
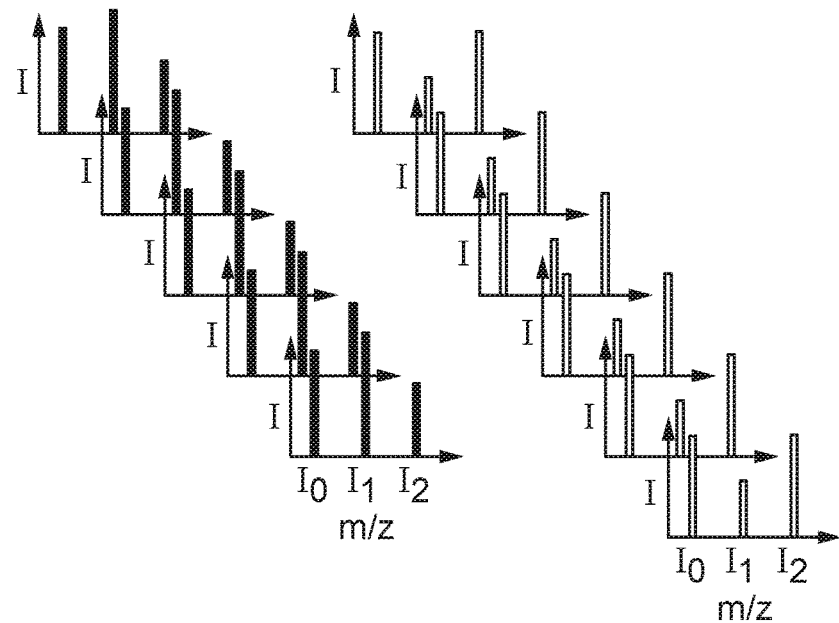
FIG. 26 shows a set of reference sample mass spectra obtained from two classes of known reference samples.

FIG. 26 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been preprocessed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 27:
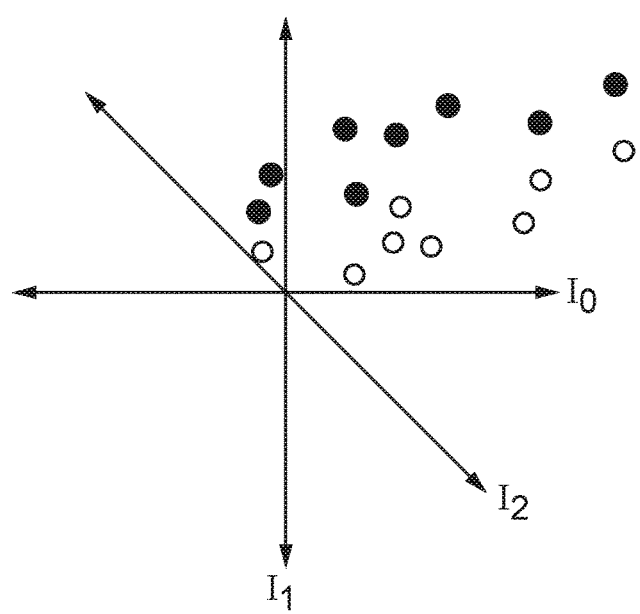
FIG. 27 shows a multivariate space having three dimensions defined by intensity axes, wherein the multivariate space comprises plural reference points, each reference point corresponding to a set of three peak intensity values derived from a reference sample mass spectrum.

FIG. 27 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 28:
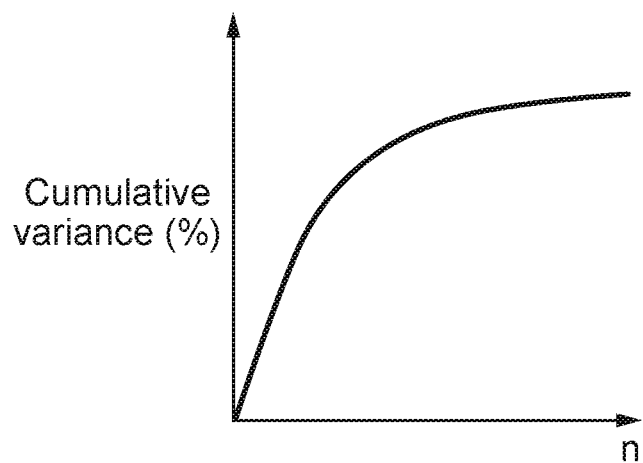
FIG. 28 shows a general relationship between cumulative variance and number of components of a PCA model.

FIG. 28 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \quad (1)$$

Figure 29:
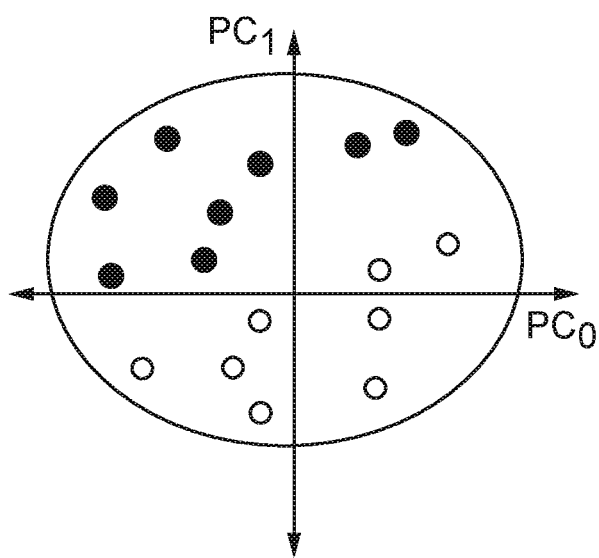
FIG. 29 shows a PCA space having two dimensions defined by principal component axes, wherein the PCA space comprises plural transformed reference points or scores, each transformed reference point corresponding to a reference point of FIG. 27.

FIG. 29 shows the resultant PCA space for the reference sample spectra of FIGS. 26 and 27. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 26 and therefore to a reference point of FIG. 27.

As is shown in FIG. 29, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \quad (2)$$

where the matrix Z contains the scores transformed into the LDA space.

Figure 30:
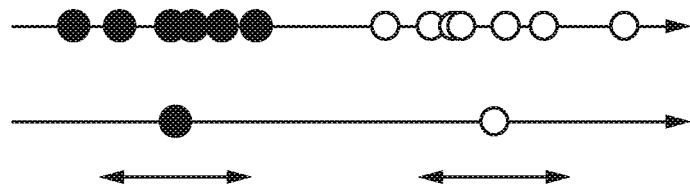
FIG. 30 shows a PCA-LDA space having a single dimension or axis, wherein the LDA is performed based on the PCA space of FIG. 29, the PCA-LDA space comprising plural further transformed reference points or class scores, each further transformed reference point corresponding to a transformed reference point or score of FIG. 29.

FIG. 30 shows a PCA-LDA space having a single dimension or axis, wherein the LDA is performed in the PCA space of FIG. 29. As is shown in FIG. 30, the LDA space comprises plural further transformed reference points or PCA-LDA scores, with each further transformed reference point corresponding to a transformed reference point or PCA score of FIG. 29.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \quad (3)$$

where $V_g$ are the class covariance matrices in the PCA space.

The transformed class average position $z_g$ for class g may be given by $$s_g U = z_g \quad (4)$$

where $s_g$ is the class average position in the PCA space.

Multivariate Analysis—Using a Model for Classification

By way of example, a method of using a classification model to classify an aerosol, smoke or vapour sample will now be described.

Figure 31:
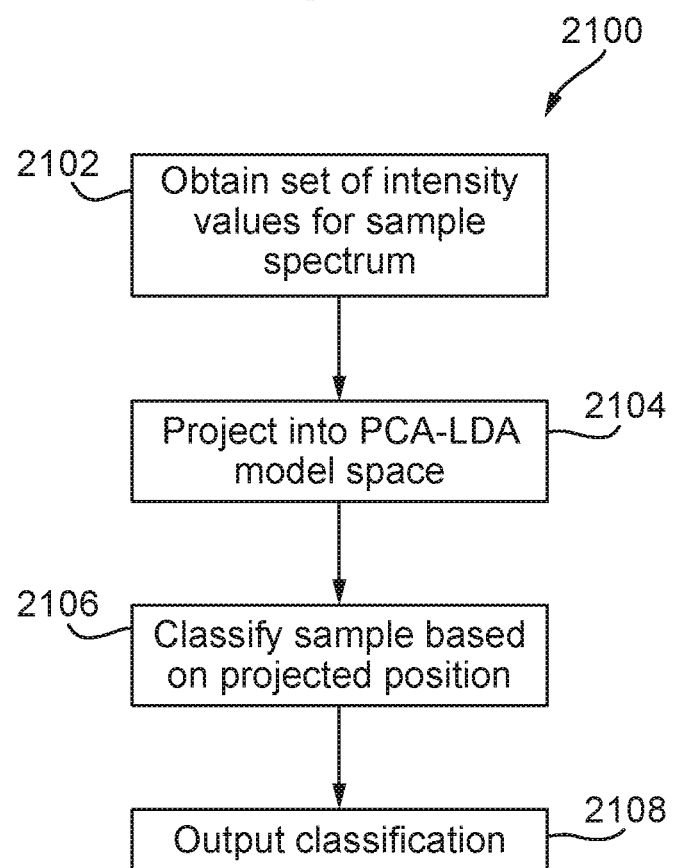
FIG. 31 shows a method of analysis that comprises using a classification model according to various embodiments.

FIG. 31 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 32:
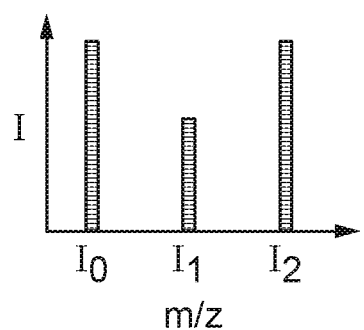
FIG. 32 shows a sample mass spectrum obtained from an unknown sample.

FIG. 32 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

Figure 33:
FIG. 33 shows the PCA-LDA space of FIG. 30, wherein the PCA-LDA space further comprises a PCA-LDA projected sample point derived from the peak intensity values of the sample mass spectrum of FIG. 32.

FIG. 33 again shows the PCA-LDA space of FIG. 30. However, the PCA-LDA space of FIG. 33 further comprises the projected sample point, corresponding to the transformed PCA-LDA vector $z_x$, derived from the peak intensity values of the sample spectrum of FIG. 32.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \quad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 34:
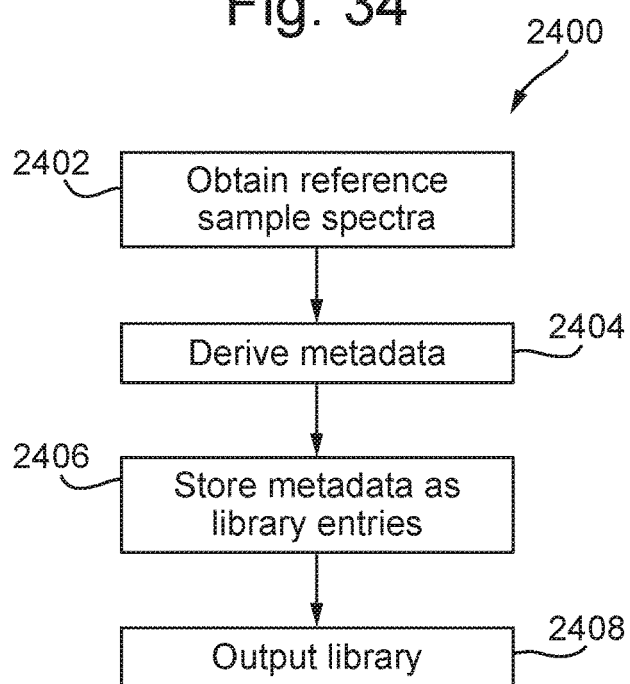
FIG. 34 shows a method of analysis that comprises building a classification library according to various embodiments.

FIG. 34 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \middle/ \log \frac{M_{max}}{M_{min}} \right\rfloor$$

where $N_{chan}$ is a selected value and denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \Gamma(C - 1/2)} \frac{1}{\left(C + \frac{(y_i - \mu_i)^2}{D_i^2}\right)^C}$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as C→∞. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

Figure 35:
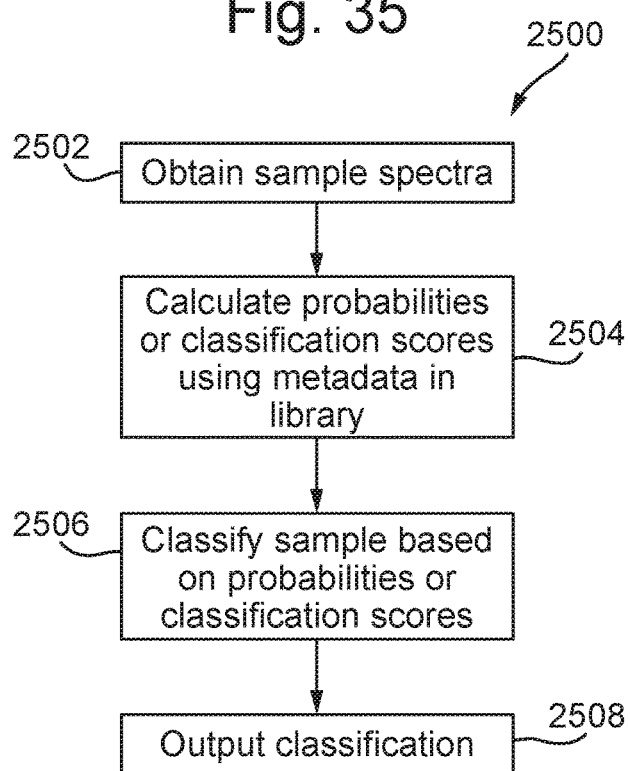
FIG. 35 shows a method of analysis that comprises using a classification library according to various embodiments.

FIG. 35 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class "$\tilde{s}$" is given by:

$$Pr(\tilde{s} | y) = \frac{L_{\tilde{s}}^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue.

Various surgical, therapeutic, medical treatment and diagnostic methods are contemplated.

However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

The various embodiments described herein provide an apparatus and associated method for the chemical analysis of aerosols and gaseous samples containing analytes using mass spectrometry or other gas-phase ion analysis modalities. The method starts with the introduction of an aerosol or other gaseous sample 201 containing the analyte into an enclosed space, where the sample 201 is mixed with a low molecular weight matrix compound 204. This homogeneous or heterogeneous mixture is then introduced into the atmospheric interface of a mass spectrometer 102 or ion mobility spectrometer via inlet 206. On the introduction of the mixture into the low pressure regime of the analytical instrument, aerosol particles containing molecular constituents of the sample and the matrix compound are formed, which are accelerated by the free jet expansion. The mixed composition aerosol particles 205 are subsequently dissociated via collisions with solid collision surfaces 209. The dissociation events produce neutral and charged species, including the molecular ions 210 of the chemical constituents of the sample. The ions 210 may be separated from the neutral species by using electric fields, e.g., by using an ion guide 212, such as a Stepwave® ion guide so as to guide ions 210 on a different path to the neutral species. The molecular ions 210 are then subjected to mass or mobility analysis. This provides a simple solution for the analysis of molecular constituents of aerosols in an on-line fashion without the application of high voltages or lasers.

The method and device provides a solution for the on-line mass spectrometric and ion mobility spectrometric analysis of gas phase or aerosol-type samples.

According to various embodiments the matrix compound 204 may be mixed into the sample aerosol 201 as a vapour or as a liquid at any point prior to introduction of the sample into the ion analyser device 207.

Although the embodiments described above relate to a particular solid collision surface geometry for performing the surface induced dissociation of the clusters, it will be appreciated that other geometries can be implemented (provided that the clusters impact the collision surface 209 at sufficiently high velocity to induce dissociation).

Although the embodiments described above result in the generation of gas phase analyte ions due to the impact with the collision surface, it is contemplated that additional ionisation techniques may be used downstream of the collision surface in order to generate the analyte ions.

Although the embodiments described above impact the mixture of matrix and analyte on a collision surface in order to atomise the mixture, it is contemplated that alternative atomisation techniques may be used.

Although the present invention has been described with reference to various embodiments, it will be understood by those skilled in the art that various changes in form and detail may be made without departing from the scope of the invention as set forth in the accompanying claims.

The invention claimed is:

1. A method of mass spectrometry and/or ion mobility spectrometry comprising:

providing an analyte by using a first device to generate aerosol, smoke or vapour from a target to be analysed;

supplying a matrix compound to said aerosol, smoke or vapour such that said analyte is diluted by, dissolved in, or forms first clusters with said matrix; and colliding said first clusters or first droplets of said diluted or dissolved analyte with a collision surface located within a vacuum chamber of a mass and/or ion mobility spectrometer so as to generate a plurality of analyte ions;

wherein supplying said matrix compound to said aerosol, smoke or vapour comprises introducing said matrix compound to said aerosol, smoke or vapour within a tube connected to an inlet of said vacuum chamber.

2. The method of mass spectrometry and/or ion mobility spectrometry as claimed in claim 1, wherein said matrix is supplied to said aerosol, smoke or vapour at a flow rate selected from the group consisting of: (i) 50-100 μl/min; (ii) 100-150 μl/min; (iii) 150-200 μl/min; (iv) 200-250 μl/min; (v) 250-300 μl/min; (vi) 300-350 μl/min; (vii) 350-400 μl/min; (viii) 400-450 μl/min; (ix) 450-500 μl/min; (x) 500-550 μl/min; (xi) 550-600 μl/min; (xii) 600-650 μl/min; (xiii) 650-700 μl/min; (xiv) 700-750 μl/min; (xv) 750-800 μl/min; (xvi) 800-850 μl/min; (xvii) 850-900 μl/min; (xviii) 900-950 μl/min; (xix) 950-1000 μl/min; (xx) 50 μl/min to 1 ml/min; (xxi) 100-800 μl/min; (xxii) 150-600 μl/min; and (xxiii) 200-400 μl/min.

3. The method of mass spectrometry and/or ion mobility spectrometry as claimed in claim 1, further comprising heating said collision surface to a temperature selected from the group consisting of: (i) 200-300 ° C.; (ii) 300-400 ° C.; (iii) 400-500 ° C.; (iv) 500-600 ° C.; (v) 600-700 ° C.; (vi) 700-800 ° C.; (vii) 800-900 ° C.; (viii) 900- 1000 ° C.; (ix) 1000-1100 ° C.; and (x) >1100 ° C.

4. The method of mass spectrometry and/or ion mobility spectrometry as claimed in claim 1, wherein said step of using said first device to generate aerosol, smoke or vapour from said target comprises irradiating said target with a laser.

5. The method of mass spectrometry and/or ion mobility spectrometry as claimed in claim 1, wherein said first device comprises or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

6. The method of mass spectrometry and/or ion mobility spectrometry as claimed in claim 1, wherein said matrix compound comprises a protic matrix solvent.

7. The method of mass spectrometry and/or ion mobility spectrometry as claimed in claim 1, wherein said matrix is selected from the group consisting of: (i) a solvent for said analyte; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; and (xxiii) propanol.

8. The method of mass spectrometry and/or ion mobility spectrometry as claimed in claim 1, further comprising using a pressure differential to accelerate said first clusters or first droplets onto said collision surface.

9. A mass spectrometer and/or ion mobility spectrometer comprising:
a first device for generating aerosol, smoke or vapour from a target to be analysed so as to provide an analyte;
a device for supplying a matrix compound to said aerosol, smoke or vapour such that said analyte is diluted by, dissolved in, or forms first clusters with said matrix; and
a collision surface located within a vacuum chamber of the spectrometer, wherein in use said first clusters or first droplets of said diluted or dissolved analyte collide with said collision surface so as to generate a plurality of analyte ions;
wherein the spectrometer is configured to introduce said matrix compound to said aerosol, smoke or vapour within a tube connected to an inlet of said vacuum chamber.

10. The mass spectrometer and/or ion mobility spectrometer as claimed in claim 9, wherein said matrix is supplied to said aerosol, smoke or vapour at a flow rate selected from the group consisting of: (i) 50-100 µl/min; (ii) 100-150 µl/min; (iii) 150-200 µl/min; (iv) 200-250 µl/min; (v) 250-300 µl/min; (vi) 300-350 µl/min; (vii) 350-400 µl/min; (viii) 400-450 µl/min; (ix) 450-500 µl/min; (x) 500-550 µl/min; (xi) 550-600 µl/min; (xii) 600-650 µl/min; (xiii) 650-700 µl/min; (xiv) 700-750 µl/min; (xv) 750-800 µl/min; (xvi) 800-850 µl/min; (xvii) 850-900 µl/min; (xviii) 900- 950 µl/min; (xix) 950-1000 µl/min; (xx) 50 µl/min to 1 ml/min; (xxi) 100-800 µl/min; (xxii) 150-600 µl/min; and (xxiii) 200-400 µl/min.

11. The mass spectrometer and/or ion mobility spectrometer as claimed in claim 9, wherein said first device comprises a laser.

12. The mass spectrometer and/or ion mobility spectrometer as claimed in claim 9, wherein said first device comprises or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic- spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

13. The mass spectrometer and/or ion mobility spectrometer as claimed in claim 9, wherein said matrix is selected from the group consisting of: (i) a solvent for said analyte; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; (xvii) an aldehyde; (xviii) a ketone; (xiv) non-polar molecules; (xx) hexane; (xxi) chloroform; (xxii) butanol; (xxiii) propanol; and (xxiv) a protic matrix solvent.

14. The mass spectrometer and/or ion mobility spectrometer as claimed in claim 9, wherein said mass spectrometer and/or ion mobility spectrometer is configured to create a pressure differential between a first region and a second region for accelerating said first clusters or first droplets between the two regions and onto said collision surface.

15. A method of mass spectrometry and/or ion mobility spectrometry comprising:
providing an analyte by using a first device to generate aerosol, smoke or vapour from a target to be analysed;
supplying a matrix compound to said aerosol, smoke or vapour such that said analyte is diluted by, dissolved in, or forms first clusters with said matrix; and
colliding said first clusters or first droplets of said diluted or dissolved analyte with a collision surface located within a vacuum chamber of a mass and/or ion mobility spectrometer so as to generate a plurality of analyte ions;

wherein supplying said matrix compound to said aerosol, smoke or vapour comprises supplying matrix molecules to said analyte and intermixing said matrix molecules with said analyte whilst said matrix compound is in a gas phase or is in the form of a vapour.

16. The method of mass spectrometry and/or ion mobility spectrometry as claimed in claim 1, wherein supplying said matrix compound to said aerosol, smoke or vapour comprises supplying matrix molecules to said analyte and intermixing said matrix molecules with said analyte whilst said matrix compound is in a gas phase or is in the form of an aerosol, vapour or solid.

17. The mass spectrometer and/or ion mobility spectrometer as claimed in claim 9, comprising a heater for heating said collision surface.

18. The method of mass spectrometry and/or ion mobility spectrometry as claimed in claim 1, wherein said tube comprises a junction and said matrix is intermixed with said aerosol, smoke or vapour at the junction.

19. The method of mass spectrometry and/or ion mobility spectrometry as claimed in claim 1, wherein said matrix or said aerosol, smoke or vapour is introduced to said tube at an opening in the circumference of the tube.

20. A mass spectrometer and/or ion mobility spectrometer, comprising:
- a first device for generating aerosol, smoke or vapour from a target to be analysed so as to provide an analyte;
- a device for supplying a gas phase or vapourised matrix compound to said aerosol, smoke or vapour such that said analyte is diluted by, dissolved in, or forms first clusters with said matrix; and
- a collision surface located within a vacuum chamber of the spectrometer, wherein in use said first clusters or first droplets of said diluted or dissolved analyte collide with said collision surface so as to generate a plurality of analyte ions.

* * * * *